US012760138B2

(12) United States Patent
Conde-Gonzalez et al.

(10) Patent No.: US 12,760,138 B2
(45) Date of Patent: Oct. 13, 2026

(54) BARRIERS INCLUDING CROSS-LINKED AMPHIPHILIC MOLECULES, AND METHODS OF MAKING THE SAME

(71) Applicant: ILLUMINA, INC., San Diego, CA (US)

(72) Inventors: Antonio Conde-Gonzalez, Cambridge (GB); Charlotte Vacogne, Cambridge (GB); Istvan Kocsis, Cambridge (GB); Alexandre Richez, Cambridge (GB); Oliver Uttley, Cambridge (GB); Miguel Angel Aleman Garcia, Cambridge (GB); Yuliia Vyborna, Sawston (GB)

(73) Assignee: ILLUMINA, INC., San Diego, CA (US)

( * ) Notice: Subject to any disclaimer, the term of this patent is extended or adjusted under 35 U.S.C. 154(b) by 620 days.

(21) Appl. No.: 18/193,522

(22) Filed: Mar. 30, 2023

(65) Prior Publication Data

US 2024/0076322 A1 Mar. 7, 2024

Related U.S. Application Data

(60) Provisional application No. 63/325,741, filed on Mar. 31, 2022.

(51) Int. Cl.
*C08F 293/00* (2006.01)
*B01D 69/14* (2006.01)
(Continued)

(52) U.S. Cl.
CPC ........ *C08F 293/005* (2013.01); *B01D 69/144* (2013.01); *B01D 71/80* (2013.01);
(Continued)

(58) Field of Classification Search
CPC ... C08F 293/005; B01D 69/144; B01D 71/80; C08L 23/06; C08L 23/26; G01N 33/48721; C12Q 2563/113; C12Q 2563/157
See application file for complete search history.

(56) References Cited

U.S. PATENT DOCUMENTS

| | | | |
|---|---|---|---|
| 5,234,566 A | 8/1993 | Osman et al. | |
| 5,795,782 A | 8/1998 | Church et al. | |

(Continued)

FOREIGN PATENT DOCUMENTS

| | | | | |
|---|---|---|---|---|
| CN | 112831395 A * | 5/2021 | ........... C12Q 1/6869 |
| EP | 2393481 B1 | 4/2019 | |

(Continued)

OTHER PUBLICATIONS

English translation CN112831395A (Year: 2025).*

(Continued)

*Primary Examiner* — Alicia Bland
(74) *Attorney, Agent, or Firm* — Sheppard, Mullin, Richter & Hampton LLP; Jaime D. Choi

(57) ABSTRACT

Barriers including crosslinked amphiphilic molecules, and methods of making the same, are provided herein. In some examples, a barrier between first and second fluids includes at least one layer comprising a plurality of amphiphilic molecules. Amphiphilic molecules of the plurality of amphiphilic molecules are crosslinked to one another.

16 Claims, 29 Drawing Sheets

(51) Int. Cl.

| | |
|---|---|
| ***B01D 71/80*** | (2006.01) |
| ***C08L 23/06*** | (2006.01) |
| ***C08L 23/26*** | (2006.01) |
| ***G01N 33/487*** | (2006.01) |

(52) U.S. Cl.

CPC ............... *C08L 23/06* (2013.01); *C08L 23/26* (2013.01); *G01N 33/48721* (2013.01); *C12Q 2563/113* (2013.01); *C12Q 2563/157* (2013.01)

(56) References Cited

U.S. PATENT DOCUMENTS

| | | | | |
|---|---|---|---|---|
| 6,015,714 | A | 1/2000 | Baldarelli et al. | |
| 6,670,403 | B2 | 12/2003 | Fisher | |
| 6,723,814 | B2 | 4/2004 | Meier et al. | |
| 6,916,488 | B1 | 7/2005 | Meier et al. | |
| 7,678,838 | B2 | 3/2010 | Pinkhassik et al. | |
| 7,939,249 | B2 | 5/2011 | Parthasarathy et al. | |
| 8,038,885 | B2 | 10/2011 | Schmidt et al. | |
| 8,324,360 | B2 | 12/2012 | Kokoris et al. | |
| 8,349,565 | B2 | 1/2013 | Kokoris et al. | |
| 8,586,301 | B2 | 11/2013 | Kokoris et al. | |
| 8,592,182 | B2 | 11/2013 | Kokoris et al. | |
| 8,993,068 | B2 | 3/2015 | Koberstein et al. | |
| 9,254,466 | B2 | 2/2016 | Xiao et al. | |
| 9,321,047 | B2 | 4/2016 | Jikihara et al. | |
| 9,670,526 | B2 | 6/2017 | Kokoris et al. | |
| 9,708,655 | B2 | 7/2017 | Mandell et al. | |
| 9,771,614 | B2 | 9/2017 | Kokoris et al. | |
| 9,823,235 | B2 | 11/2017 | Heron et al. | |
| 9,920,386 | B2 | 3/2018 | Kokoris et al. | |
| 10,301,345 | B2 | 5/2019 | Kokoris et al. | |
| 10,457,979 | B2 | 10/2019 | McRuer et al. | |
| 10,676,782 | B2 | 6/2020 | McRuer et al. | |
| 10,745,685 | B2 | 8/2020 | Kokoris et al. | |
| 10,774,105 | B2 | 9/2020 | Kokoris et al. | |
| 10,851,405 | B2 | 12/2020 | Kokoris et al. | |
| 10,947,590 | B2 | 3/2021 | Barrall et al. | |
| 11,008,627 | B2 | 5/2021 | Andeshmand et al. | |
| 2007/0026282 | A1 | 2/2007 | Kumagal et al. | |
| 2012/0116024 | A1 | 5/2012 | Iyoda et al. | |
| 2016/0279577 | A1 | 9/2016 | Fritsch | |
| 2020/0246791 | A1 | 8/2020 | Barrall et al. | |
| 2021/0197129 | A1 | 7/2021 | Rangou et al. | |
| 2021/0302409 | A1 | 9/2021 | Barrall et al. | |
| 2023/0041418 | A1* | 2/2023 | Brown | C12Q 1/6806 |
| 2023/0090867 | A1 | 3/2023 | Mandell et al. | |

FOREIGN PATENT DOCUMENTS

| | | | | |
|---|---|---|---|---|
| EP | 3122444 | B1 | 6/2021 | |
| WO | 2002071944 | A1 | 9/2002 | |
| WO | 2004011600 | A2 | 2/2004 | |
| WO | 2008021067 | A1 | 2/2008 | |
| WO | 2012164270 | A1 | 12/2012 | |
| WO | 2013153359 | A1 | 10/2013 | |
| WO | 2014064443 | A2 | 5/2014 | |
| WO | 2014064444 | A1 | 5/2014 | |
| WO | 2016004029 | A1 | 1/2016 | |
| WO | 2019028361 | A1 | 2/2019 | |
| WO | 2019213571 | A1 | 11/2019 | |
| WO | 2020216885 | A1 | 10/2020 | |
| WO | 2021086623 | A1 | 5/2021 | |
| WO | WO-2021111139 | A1 * | 6/2021 | G01N 33/54353 |
| WO | 2021168287 | A1 | 8/2021 | |

OTHER PUBLICATIONS

Aikawa et al., "Comparison of Carboxybetaine with Sulfobetaine as Lipid Headgroup Involved in Intermolecular Interaction between Lipids in the Membrane," ACS Omega, 2(9): pp. 5803-5812 (2017) https://doi.org/10.1021/acsomega.7600574.

Askes et al., "Dynamics of dual-fluorescent polymersomes with durable integrity in living cancer cells and zebrafish embryos," Biomaterials, 168: pp. 54-63 (2018) doi: 10.1016/j.biomaterials.2018.03.037. Epub Mar. 22, 2018.

Butler et al., "Single-molecule DNA detection with an engineered MspA protein nanopore," Proc. Natl. Acad. Sci., 105(52): pp. 20647-20652 (2008).

Dergunov et al., "Bilayer-Templated Two-Dimensional RAFT Polymerization for Directed Assembly of Polymer Nanostructures," Angew. Chem. Int. Ed. 59(42): pp. 18405-18411 (2020).

Dergunov et al., "Bilayer-Templated Two-Dimensional RAFT Polymerization for Directed Assembly of Polymer Nanostructures," Angew. Chem. Int. Ed. Supplemental Information: pp. 1-44 (2020).

Derrington et al., "Nanopore DNA sequencing with MspA," PNAS 107(37): pp. 16060-16065 (2010).

Dreier et al., "Unraveling the Origin of the Apparent Charge of Zwitterionic Lipid Layers," J. Phys. Chem. Lett., 10(20): pp. 6355-6359 (2019) https://doi.org/10.1021/acs.jpclett.9b02587.

Fan et al., "Linear-dendritic block copolymer for drug and gene delivery," Materials Science and Engineering C 62: pp. 943-959 (2016) http://dx.doi.org/10.1016/j.msec2016.01.044.

Farquignon et al., "Large and Giant Unilamellar Vesicle(s) Obtained by Self-Assembly of Poly(dimethylsiloxane)-b-poly(ethyleneoxide) Diblock Copolymers, Membrane Properties and Preliminary Investigation of their Ability to Form Hybrid Polymer/Lipid Vesicles," Polymers, MDPI. 11(12):2013, 27 pages (2019) 10.3390/polym11122013.hal-02396483.

Fernandez-Megia et al., ""Clickable"" PEG-Dendritic Block Copolymers. Biomacromolecules, 7: pp. 3104-3111 (2006).

Galin et al., "Structural and Thermodynamic Study of Dimethylsiloxane-Ethylene Oxide PDMS-PEO-PDMS Triblock Copolymers," Macromolecules, 14: pp. 677-683 (1981).

Gaspard et al., "Mechanical characterization of hybrid vesicles based on linear poly(dimethylsiloxane-b-ethylene oxide) and poly(butadiene-b-ethylene oxide) block copolymers," Sensors, 16(3): pp. 1-12 (2016) doi: 10.3390/s16030390.

Goda et al., "Thiolated 2-Methacryloyloxyethyl Phosphorylcholine For an Antifouling Biosensor Platform," Chem. Commun. 49(77): pp. 8683-8685 (2013) https://doi.org/10.1039/C3cc44357d.

HAWKINS Dissertation, "Antifouling Silicone Coatings Prepared With PEO-Silane Amphiphiles," 168 pages (2014).

He et al., "A Mechanistic Study on Amphiphilic Block Co-polymer Poly(butadiene-b-(ethylene oxide)) Vesicles Reveals Water Permeation Mechanism through Polymeric Bilayer," RSC Adv., 4: pp. 15304-15313 (2014).

Jeon et al., "Hydrogel-Encapsulated Lipid Membranes," Journal of the American Chemical Society 128, 42-43 (2006).

Kuang et al., ""Frozen"" block copolymer nanomembranes with light-driven proton pumping performance, ACS Nano, 8(1): pp. 537-545 (2014) DOI: 10.1021/nn4059852.

Maingi et al., "Stability and Dynamics of Membrane-Spanning DNA Nanopores," Nat. Commun, 8:14784: pp. 1-12 (2017) https://doi.org/10.1038/ncomms14784.

Morton et al., "Tailored polymeric membranes for *Mycobacterium smegmatis* porin A (MspA) based biosensors," Journal of Materials Chemistry B, 3(25): pp. 5080-5086 (2015).

Muhammad et al., "Engineering of the *E. coli* Outer Membrane Protein FhuA to overcome the Hydrophobic Mismatch in Thick Polymeric Membranes," Journal of nanobiotechnology, 9(8): pp. 1-9 (2011) doi: 10.1186/1477-3155-9-8.

Nardin et al., "Amphiphilic Block Copolymer Nanocontainers as Bioreactors," Eur. Phys. J. E., 4: pp. 403-410 (2001).

Neugebauer et al., "PDMS-PEO Densely Grafted Copolymers," Macromolecules, 38(21): pp. 8687-8693 (2005).

Percec et al., "Self-Assembly of Janus Dendrimers Into Uniform Dendrimersomes and Other Complex Architectures," Science (New York, N.Y.). 328: pp. 1009-1014 (2010) 10.1126/science.1185547.

Rahimi et al., "Amphiphilic zwitterionic-PDMS-based surface-modifying additives to tune fouling-release of siloxane-polyurethane marine coatings," Progress in Organic Coatings, Elsevier Science Direct, 149, 105931: pp. 1-14 (2020).

Risangud et al., "Hydrosilylation as an Efficient Tool for Polymer Synthesis and Modification with Methacrylates," RSC Adv. 5(8): pp. 5879-5885 (2015) https://doi.org/10.1039/C4RA14956D.

(56) References Cited

OTHER PUBLICATIONS

Risangud et al., "Hydrosilylation as an Efficient Tool for Polymer Synthesis and Modification with Methacrylates," RSC Adv. Supplemental Information: pp. 1-20 (2015).
Rofeh et al., "Microfluidic block copolymer membrane arrays for nanopore DNA sequencing," Appl. Phys. Lett., 114: pp. 213701-1 to 213701-5 (2019).
Rofeh et al., "Microfluidic block copolymer membrane arrays for nanopore DNA sequencing," Appl. Phys. Lett. Supplemental Information: pp. 1-14 (2019).
Sarkar et al., "De-symmetrizing periodically grafted amphiphilic copolymers: design, synthesis and generation of Janus folded chains," Polym. Chem., 10: pp. 1730-1740 (2019).
Sarkar et al., "De-symmetrizing periodically grafted amphiphilic copolymers: design, synthesis and generation of Janus folded chains," Supplemental Information (ESI) for Polym. Chem.: pp. S1-S28 (2019).
Shen et al., "Interfacial Water Structure at Zwitterionic Membrane/Water Interface: The Importance of Interactions between Water and Lipid Carbonyl Groups," ACS Omega, 5(29): pp. 18080-18090 (2020) https://doi.org/10.1021/acsomega.0c01633.
Wang et al., "Single-molecule DNA detection using a novel SPI protein nanopore," Chem. Commun., 49: pp. 1741-1743 (2013).
Wilson et al., "A generalized method for Magnetite Nanoparticle Steric Stabilization Utilizing Block Copolymers Containing Carboxylic Acids," European Cells and Materials, 3(2): pp. 206-209 (2002).
Yang et al., "Bilayered membranes of Janus dendrimers with hybrid hydrogenated and fluorinated dendrons: microstructures and coassembly with lipids," Phys Chem Chem Phys., 21(28): pp. 15400-15407 (2019) doi: 10.1039/c9cp01635j. PMID: 31271395.
Yang et al., "Bilayered membranes of Janus dendrimers with hybrid hydrogenated and fluorinated dendrons: microstructures and coassembly with lipids," Phys. Chem. Chem. Phys., Supplemental Information (2019).
Yu et al., "Stable polymer bilayers for protein channel recordings at high guanidinium chloride concentrations," Biophysical Journal, 120(9): pp. 1537-1541 (2021).
Zhang et al., "Natural channel protein inserts and functions in a completely artificial, solid-supported bilayer membrane," Sci Rep., 3:2196: pp. 1-7 (2013) doi: 10.1038/srep02196. PMID: 23846807; PMCID: PMC3709162.
Zhang et al., "Self-assembly of amphiphilic Janus dendrimers into uniform onion-like dendrimersomes with predictable size and number of bilayers," PNAS, 111(25): pp. 9058-9063 (2014) https://www.pnas.org/doi/full/10.1073/pnas.1402858111.
Zhang et al., "Synthesis and properties of pH-cleavable toothbrush-like copolymers comprising multi-reactive Y junctions and a linear or cyclic backbone," Polym. Chem., 11: pp. 2098-2109 (2020).
Zhang et al., "Synthesis and properties of pH-cleavable toothbrush-like copolymers comprising multi-reactive Y junctions and a linear or cyclic backbone," Polym. Chem. Supplemental Information: pp. 1-10 (2020).
Garni et al., "Biopores/membrane proteins in synthetic polymer membranes," Biochimica Et Biophysica Acta, Elsevier, Amsterdam, Nl, 1859(4): pp. 619-638 (2016) XP029914706 DOI: 10.1016/J.BBAMEM.2016.10.015.
Bell et al., "DNA Origami Nanopores," Nano Letters, 12(1): pp. 512-517 (2011) URL:https://pubs.acs.org/doi/pdf/10.1021/n1204098n XP093056474 DOI: 10.1021/n1204098n ISSN: 1530-6984.
International Search Report and Written Opinion for PCT/EP2023/058387 dated Jul. 3, 2023; 14 pages.
Tang et al., "Fabrications, Applications and Challenges of Solid-State Nanopores: A Mini Review," Nanosystems, Nanomaterials, Nanotechnologies, 6: pp. 35 (2016) URL:http://journals.sagepub.com/doi/pdf/10.5772/64015 XP093056438 DOI: 10.5772/64015 ISSN: 1847-9804.
Yoshida et al., "Slowing the translocation of single-stranded DNA by using nano-cylindrical passage self-assembled by amphiphilic block copolymers," United Kingdom 8(43): pp. 18270-18276 (2016) URL:https://pubs.rscorg/en/content/articlepdf/2016/nr/c6nr06575a XP093056439 DOI: 10.1039/C6NR06575A ISSN:2040-3364.
Zhishan et al., "Solid-State Nanopore," Nanoscale Research Letters, Springer, 13(1): pp. 1-10 (2018) XP021253638 DOI: 10.1186/S11671-018-2463-Z ISSN:1931-7573.

* cited by examiner

BARRIERS INCLUDING CROSS-LINKED AMPHIPHILIC MOLECULES, AND METHODS OF MAKING THE SAME

CROSS-REFERENCE TO RELATED APPLICATIONS

This application claims the benefit of U.S. Provisional Patent Application No. 63/325,741, filed Mar. 31, 2022 and entitled "BARRIERS INCLUDING CROSS-LINKED AMPHIPHILIC MOLECULES, AND METHODS OF MAKING THE SAME", the entire contents of which are incorporated by reference herein.

FIELD

This application relates to barriers that include amphiphilic molecules.

BACKGROUND

A significant amount of academic and corporate time and energy has been invested into using nanopores to sequence polynucleotides. For example, the dwell time has been measured for complexes of DNA with the Klenow fragment (KF) of DNA polymerase I atop a nanopore in an applied electric field. Or, for example, a current or flux-measuring sensor has been used in experiments involving DNA captured in an α-hemolysin nanopore. Or, for example, KF-DNA complexes have been distinguished on the basis of their properties when captured in an electric field atop an α-hemolysin nanopore. In still another example, polynucleotide sequencing is performed using a single polymerase enzyme complex including a polymerase enzyme and a template nucleic acid attached proximal to a nanopore, and nucleotide analogs in solution. The nucleotide analogs include charge blockade labels that are attached to the polyphosphate portion of the nucleotide analog such that the charge blockade labels are cleaved when the nucleotide analog is incorporated into a polynucleotide that is being synthesized. The charge blockade label is detected by the nanopore to determine the presence and identity of the incorporated nucleotide and thereby determine the sequence of a template polynucleotide. In still other examples, constructs include a transmembrane protein nanopore subunit and a nucleic acid handling enzyme.

However, such previously known devices, systems, and methods may not necessarily be sufficiently robust, reproducible, or sensitive and may not have sufficiently high throughput for practical implementation, e.g., demanding commercial applications such as genome sequencing in clinical and other settings that demand cost effective and highly accurate operation. Accordingly, what is needed are improved devices, systems, and methods for sequencing polynucleotides, which may include using membranes having nanopores disposed therein.

SUMMARY

Barriers including crosslinked amphiphilic molecules, and methods of making the same, are provided herein.

Some examples herein provide a barrier between first and second fluids. The barrier may include at least one layer including a plurality of amphiphilic molecules. Amphiphilic molecules of the plurality of amphiphilic molecules are cross-linked to one another.

In some examples, the at least one layer includes a first layer including a first plurality of the amphiphilic molecules; and a second layer including a second plurality of amphiphilic molecules contacting the first plurality of amphiphilic molecules. Amphiphilic molecules of the first layer may be crosslinked to one another, and amphiphilic molecules of the second layer may be crosslinked to one another.

In some examples, the amphiphilic molecules include at least one hydrophobic block coupled to at least one hydrophilic block at an interface. In some examples, the amphiphilic molecules are crosslinked to one another at the hydrophilic blocks. In some examples, the amphiphilic molecules are crosslinked to one another at the hydrophobic blocks. In some examples, the amphiphilic molecules are crosslinked to one another at the interface.

In some examples, the amphiphilic molecules include molecules of a diblock copolymer, molecules of the diblock copolymer include a hydrophobic block coupled to a hydrophilic block.

In some examples, the amphiphilic molecules include molecules of a triblock copolymer. In some examples, each molecule of the triblock copolymer includes first and second hydrophobic blocks and a hydrophilic block coupled to and between the first and second hydrophobic blocks. In some examples, each molecule of the triblock copolymer includes first and second hydrophilic blocks and a hydrophobic block coupled to and between the first and second hydrophilic blocks.

In some examples, the amphiphilic molecules are cross-linked by a product of a polymerization reaction. In some examples, the product of the polymerization reaction includes a reacted itaconic moiety, a reacted N-carboxyanhydride moiety, a reacted disulfyl pyridyl moiety, a reacted N-hydroxy succinimide (NHS) ester, a reacted acrylate moiety, a reacted methacrylate moiety, a reacted acrylamide moiety, a reacted methacrylamide moiety, a reacted styrenic moiety, a reacted maleic moiety, a reacted carboxylic acid moiety, a reacted thiol moiety, a reacted allyl moiety, a reacted vinyl moiety, a reacted propargyl moiety, or a reacted maleimide moiety.

In some examples, the amphiphilic molecules are cross-linked by a product of a coupling reaction. In some examples, the coupling reaction includes a thiol-ene click reaction, a thiol-yne click reaction, a strain-promoted alkyne-azide cycloaddition, an amide coupling, a thiol/aza-Michael reaction, a [2+2] cycloaddition, a thio-Michael click reaction, a condensation reaction, a [2+2] photocycloaddition, a protein-ligand interaction, host-guest chemistry, a disulfide formation, an imine formation, or an enamine formation.

In some examples, the barrier further includes a nanopore within the barrier. In some examples, the nanopore includes α-hemolysin or MspA.

In some examples, the barrier is suspended by a barrier support defining an aperture, the one or more layers being suspended across the aperture.

Some examples herein provide a barrier between first and second fluids. The barrier may include at least one layer including a plurality of amphiphilic molecules. The amphiphilic molecules comprise reactive moieties to perform a crosslinking reaction with one another.

In some examples, the at least one layer includes a first layer including a first plurality of amphiphilic molecules; and a second layer including a second plurality of the amphiphilic molecules contacting the first plurality of amphiphilic molecules.

In some examples, the reactive moieties are selected from the group consisting of an itaconic moiety, an N-carboxyanhydride moiety, a disulfyl pyridyl moiety, an N-hydroxy succinimide (NHS) ester, acrylate moiety, a methacrylate moiety, an acrylamide moiety, a methacrylamide moiety, a styrenic moiety, a maleic moiety, a carboxylic acid moiety, a thiol moiety, an allyl moiety, a vinyl moiety, a propargyl moiety, and a maleimide moiety.

In some examples, the reactive moieties include a mixture of moieties that are reactive with one another via a thiol-ene click reaction, a thiol-yne click reaction, a strain-promoted alkyne-azide cycloaddition, an amide coupling, a thiol/aza-Michael reaction, a [2+2] cycloaddition, a thio-Michael click reaction, a condensation reaction, a [2+2] photocycloaddition, a protein-ligand interaction, host-guest chemistry, a disulfide formation, an imine formation, or an enamine formation.

In some examples, the amphiphilic molecules include at least one hydrophobic block coupled to at least one hydrophilic block at an interface. In some examples, the reactive moieties are located at the hydrophilic blocks of respective amphiphilic molecules. In some examples, the reactive moieties are located at the hydrophobic blocks of respective amphiphilic molecules. In some examples, the reactive moieties are located at the interfaces of respective amphiphilic molecules.

In some examples, the amphiphilic molecules include molecules of a diblock copolymer, molecules of the diblock copolymer including a hydrophobic block coupled to a hydrophilic block.

In some examples, the amphiphilic molecules include molecules of a triblock copolymer. In some examples, each molecule of the triblock copolymer includes first and second hydrophobic blocks and a hydrophilic block coupled to and between the first and second hydrophobic blocks. In some examples, each molecule of the triblock copolymer includes first and second hydrophilic blocks and a hydrophobic block coupled to and between the first and second hydrophilic blocks.

In some examples, the barrier further includes a nanopore within the barrier. In some examples, the nanopore includes α-hemolysin or MspA.

In some examples, the barrier is suspended by a barrier support defining an aperture, the one or more layers being suspended across the aperture.

Some examples herein provide a method of forming a barrier between first and second fluids. The method may include forming at least one layer including a plurality of amphiphilic molecules, wherein the amphiphilic molecules include reactive moieties. The method may include using crosslinking reactions of the reactive moieties to crosslink amphiphilic molecules of the plurality to one another.

In some examples, forming the at least one layer comprises forming a first layer comprising a first plurality of the amphiphilic molecules, and forming a second layer comprising a second plurality of the amphiphilic molecules.

In some examples, the crosslinking reaction includes a polymerization reaction. In some examples, the reactive moieties are selected from the group consisting of an itaconic moiety, an N-carboxyanhydride moiety, a disulfyl pyridyl moiety, an N-hydroxy succinimide (NHS) ester, an acrylate moiety, a methacrylate moiety, an acrylamide moiety, a methacrylamide moiety, a styrenic moiety, a maleic moiety, a carboxylic acid moiety, a thiol moiety, an allyl moiety, a vinyl moiety, a propargyl moiety, and a maleimide moiety. In some examples, the polymerization reaction includes a ring-opening polymerization or a step-growth polymerization. In some examples, the method further includes initiating the polymerization reaction using an initiator. In some examples, the initiator includes a photoinitiator, a redox system, or photons. In some examples, the photoinitiator is selected from the group consisting of: 2,2-dimethoxy-2-phenylacetophenone, 2,2'-azobis(2-methylpropionamidine) dihydrochloride, 2-hydroxy-4'-(2-hydroxyethoxy)-2-methylpropiophenone, and lithium phenyl-2,4,6-trimethylbenzoylphosphinate. In some examples, the redox system includes potassium persulfate or ammonium persulfate and N,N,N',N'-tetramethylethylenediamine.

In some examples, the crosslinking reaction includes a coupling reaction. In some examples, the coupling reaction includes a thiol-ene click reaction, a thiol-yne click reaction, a strain-promoted alkyne-azide cycloaddition, an amide coupling, a thiol/aza-Michael reaction, a [2+2] photocycloaddition, a protein-ligand interaction, host-guest chemistry, a disulfide formation, an imine formation, or an enamine formation. In some examples, the coupling reaction is initiated using an initiator. In some examples, the initiator includes a free-radical initiator, a redox system, a reducing agent, or photons. In some examples, the free-radical initiator includes 2-hydroxy-4'-(2-hydroxyethoxy)-2-methylpropiophenone, or 2,2'-azobis(2-methylpropionamidine) dihydrochloride. In some examples, the redox system includes potassium persulfate or ammonium persulfate and N,N,N',N'-tetramethylethylenediamine. In some examples, the reducing agent includes tris(2-carboxyethyl)phosphine, dithiothreitol, sodium ascorbate, or a phosphine. In some examples, the reactive moieties include a disulfide pyridyl moiety, a lipoamido moiety, a propargyl moiety, an azide moiety, a DBCO moiety, a BCN moiety, an amine moiety, an activated carboxylic moiety, a dimethylmaleimide moiety, or a maleimide moiety.

In some examples, the reactive moieties are located at hydrophilic blocks of the amphiphilic molecules. In some examples, the reactive moieties are located at interfaces between hydrophilic blocks and hydrophobic blocks of the amphiphilic molecules. In some examples, the reactive moieties are located at hydrophilic blocks of the amphiphilic molecules.

In some examples, the amphiphilic molecules have an AB architecture. In some examples, the amphiphilic molecules have an ABA architecture. In some examples, the amphiphilic molecules have a BAB architecture.

In some examples, the amphiphilic molecules include poly(dimethyl siloxane) (PDMS). In some examples, the amphiphilic molecules include poly(ethylene oxide) (PEO).

It is to be understood that any respective features/examples of each of the aspects of the disclosure as described herein may be implemented together in any appropriate combination, and that any features/examples from any one or more of these aspects may be implemented together with any of the features of the other aspect(s) as described herein in any appropriate combination to achieve the benefits as described herein.

DETAILED DESCRIPTION

Figure 1:
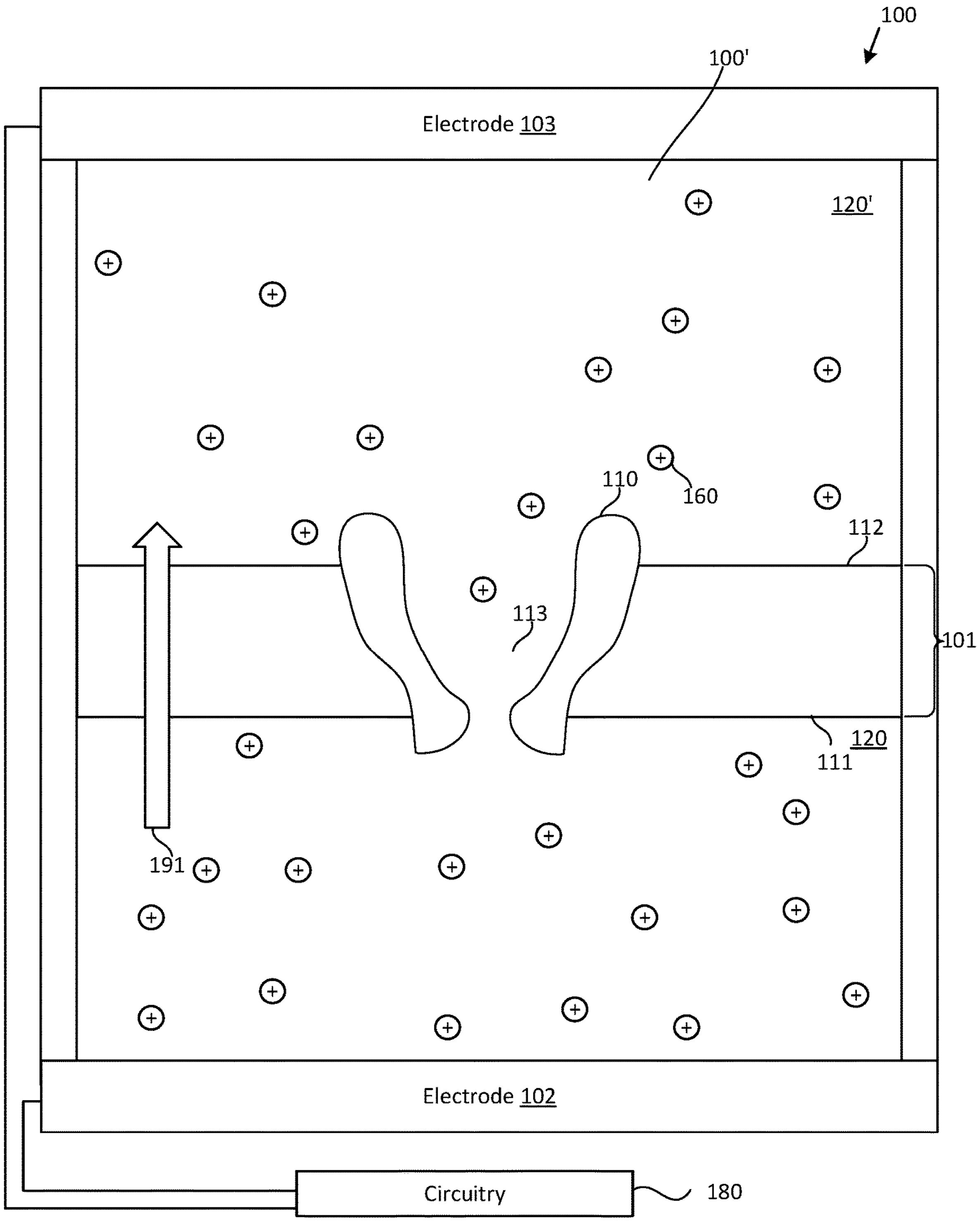
FIG. 1 schematically illustrates a cross-sectional view of an example nanopore composition and device including a barrier.

Barriers including cross-linked amphiphilic molecules, and methods of making the same, are provided herein.

For example, nanopore sequencing may utilize a nanopore that is inserted into a barrier such as a polymeric membrane, and that includes an aperture through which ions and/or other molecules may flow from one side of the membrane to the other. Circuitry may be used to detect a sequence of nucleotides. For example, during sequencing-by-synthesis (SBS), on a first side of the barrier, a polymerase adds the nucleotides to a growing polynucleotide in an order that is based on the sequence of a template polynucleotide to which the growing polynucleotide is hybridized. The sensitivity of the circuitry may be improved by using fluids with different compositions on respective sides of the membrane, for example to provide suitable ion transport for detection on one side of the membrane, while suitably promoting activity of the polymerase on the other side of the barrier. Accordingly, barrier stability is beneficial.

As provided herein, a barrier including amphiphilic molecules may be stabilized by cross-linking the amphiphilic molecules. Illustratively, the amphiphilic molecules may be or include polymer chains that include functional groups at their respective hydrophilic (A) ends, at their respective hydrophobic (B) ends, or at the hydrophilic-hydrophobic (A-B) interface, or at combinations of such locations (e.g., at the hydrophilic ends and/or at the hydrophobic ends and/or at the hydrophilic-hydrophobic interface). The functional groups may be reacted in such a manner as to cross-link the amphiphilic molecules and thus enhance membrane stability. In examples in which a nanopore is inserted into the membrane, the crosslinking is expected not to detrimentally affect nanopore functionality. For example, the nanopore may retain its ability to relax, and its mobility within the membrane. As such, the present cross-linking may not completely rigidify the membrane. Accordingly, the membrane may be expected to be sufficiently strong and stable for prolonged use under forces such as may be applied during use of a device including such a membrane, illustratively genomic sequencing. Additionally, as described in greater detail below, a wide variety of different cross-linking chemistries suitably may be used, such as polymerization reactions or covalent coupling reactions.

First, some terms used herein will be briefly explained. Then, some example methods for forming barriers including cross-linked amphiphilic molecules, and intermediate structures formed using such methods, will be described.

Terms

Unless defined otherwise, all technical and scientific terms used herein have the same meaning as is commonly understood by one of ordinary skill in the art. The use of the term "including" as well as other forms, such as "include," "includes," and "included," is not limiting. The use of the term "having" as well as other forms, such as "have," "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps, but may include additional steps. When used in the context of a compound, composition, or system, the term "comprising" means that the compound, composition, or system includes at least the recited features or components, but may also include additional features or components.

As used herein, the singular forms "a", "an" and "the" include plural referents unless the content clearly dictates otherwise.

The terms "substantially," "approximately," and "about" used throughout this specification are used to describe and account for small fluctuations, such as due to variations in processing. For example, they may refer to less than or equal to ±10%, such as less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

As used herein, the term "nucleotide" is intended to mean a molecule that includes a sugar and at least one phosphate group, and in some examples also includes a nucleobase. A nucleotide that lacks a nucleobase may be referred to as "abasic." Nucleotides include deoxyribonucleotides, modified deoxyribonucleotides, ribonucleotides, modified ribonucleotides, peptide nucleotides, modified peptide nucleotides, modified phosphate sugar backbone nucleotides, and mixtures thereof. Examples of nucleotides include adenosine monophosphate (AMP), adenosine diphosphate (ADP), adenosine triphosphate (ATP), thymidine monophosphate (TMP), thymidine diphosphate (TDP), thymidine triphosphate (TTP), cytidine monophosphate (CMP), cytidine diphosphate (CDP), cytidine triphosphate (CTP), guanosine monophosphate (GMP), guanosine diphosphate (GDP), guanosine triphosphate (GTP), uridine monophosphate (UMP), uridine diphosphate (UDP), uridine triphosphate (UTP), deoxyadenosine monophosphate (dAMP), deoxyadenosine diphosphate (dADP), deoxyadenosine triphosphate (dATP), deoxythymidine monophosphate (dTMP), deoxythymidine diphosphate (dTDP), deoxythymidine triphosphate (dTTP), deoxycytidine diphosphate (dCDP), deoxycytidine triphosphate (dCTP), deoxyguanosine monophosphate (dGMP), deoxyguanosine diphosphate (dGDP), deoxyguanosine triphosphate (dGTP), deoxyuridine monophosphate (dUMP), deoxyuridine diphosphate (dUDP), and deoxyuridine triphosphate (dUTP).

As used herein, the term "nucleotide" also is intended to encompass any nucleotide analogue which is a type of nucleotide that includes a modified nucleobase, sugar, backbone, and/or phosphate moiety compared to naturally occurring nucleotides. Nucleotide analogues also may be referred to as "modified nucleic acids." Example modified nucleobases include inosine, xanthine, hypoxanthine, isocytosine, isoguanine, 2-aminopurine, 5-methylcytosine, 5-hydroxymethyl cytosine, 2-aminoadenine, 6-methyl adenine, 6-methyl guanine, 2-propyl guanine, 2-propyl adenine, 2-thiouracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. As is known in the art, certain nucleotide analogues cannot become incorporated into a polynucleotide, for example, nucleotide analogues such as adenosine 5'-phosphosulfate. Nucleotides may include any suitable number of phosphates, e.g., three, four, five, six, or more than six phosphates. Nucleotide analogues also include locked nucleic acids (LNA), peptide nucleic acids (PNA), and 5-hydroxybutynl-2'-deoxyuridine ("super T").

As used herein, the term "polynucleotide" refers to a molecule that includes a sequence of nucleotides that are bonded to one another. A polynucleotide is one nonlimiting example of a polymer. Examples of polynucleotides include deoxyribonucleic acid (DNA), ribonucleic acid (RNA), and analogues thereof such as locked nucleic acids (LNA) and peptide nucleic acids (PNA). A polynucleotide may be a single stranded sequence of nucleotides, such as RNA or single stranded DNA, a double stranded sequence of nucleotides, such as double stranded DNA, or may include a mixture of a single stranded and double stranded sequences of nucleotides. Double stranded DNA (dsDNA) includes genomic DNA, and PCR and amplification products. Single stranded DNA (ssDNA) can be converted to dsDNA and vice-versa. Polynucleotides may include non-naturally occurring DNA, such as enantiomeric DNA, LNA, or PNA. The precise sequence of nucleotides in a polynucleotide may be known or unknown. The following are examples of polynucleotides: a gene or gene fragment (for example, a probe, primer, expressed sequence tag (EST) or serial analysis of gene expression (SAGE) tag), genomic DNA, genomic DNA fragment, exon, intron, messenger RNA (mRNA), transfer RNA, ribosomal RNA, ribozyme, cDNA, recombinant polynucleotide, synthetic polynucleotide, branched polynucleotide, plasmid, vector, isolated DNA of any sequence, isolated RNA of any sequence, nucleic acid probe, primer or amplified copy of any of the foregoing.

As used herein, a “polymerase” is intended to mean an enzyme having an active site that assembles polynucleotides by polymerizing nucleotides into polynucleotides. A polymerase can bind a primer and a single stranded target polynucleotide, and can sequentially add nucleotides to the growing primer to form a “complementary copy” polynucleotide having a sequence that is complementary to that of the target polynucleotide. DNA polymerases may bind to the target polynucleotide and then move down the target polynucleotide sequentially adding nucleotides to the free hydroxyl group at the 3' end of a growing polynucleotide strand. DNA polymerases may synthesize complementary DNA molecules from DNA templates. RNA polymerases may synthesize RNA molecules from DNA templates (transcription). Other RNA polymerases, such as reverse transcriptases, may synthesize cDNA molecules from RNA templates. Still other RNA polymerases may synthesize RNA molecules from RNA templates, such as RdRP. Polymerases may use a short RNA or DNA strand (primer), to begin strand growth. Some polymerases may displace the strand upstream of the site where they are adding bases to a chain. Such polymerases may be said to be strand displacing, meaning they have an activity that removes a complementary strand from a template strand being read by the polymerase.

Example DNA polymerases include Bst DNA polymerase, 9° Nm DNA polymerase, Phi29 DNA polymerase, DNA polymerase I (*E. coli*), DNA polymerase I (Large), (Klenow) fragment, Klenow fragment (3'-5' exo−), T4 DNA polymerase, T7 DNA polymerase, Deep VentR™ (exo−) DNA polymerase, Deep VentR™ DNA polymerase, DyNAzyme™ EXT DNA, DyNAzyme™ II Hot Start DNA Polymerase, Phusion™ High-Fidelity DNA Polymerase, Therminator™ DNA Polymerase, Therminator™ II DNA Polymerase, VentR® DNA Polymerase, VentR® (exo−) DNA Polymerase, RepliPHI™ Phi29 DNA Polymerase, rBst DNA Polymerase, rBst DNA Polymerase (Large), Fragment (IsoTherm™ DNA Polymerase), MasterAmp™ AmpliTherm™, DNA Polymerase, Taq DNA polymerase, Tth DNA polymerase, Tfl DNA polymerase, Tgo DNA polymerase, SP6 DNA polymerase, Tbr DNA polymerase, DNA polymerase Beta, ThermoPhi DNA polymerase, and Isopol™ SD+ polymerase. In specific, nonlimiting examples, the polymerase is selected from a group consisting of Bst, Bsu, and Phi29. Some polymerases have an activity that degrades the strand behind them (3' exonuclease activity). Some useful polymerases have been modified, either by mutation or otherwise, to reduce or eliminate 3' and/or 5' exonuclease activity.

Example RNA polymerases include RdRps (RNA dependent, RNA polymerases) that catalyze the synthesis of the RNA strand complementary to a given RNA template. Example RdRps include polioviral 3Dpol, vesicular stomatitis virus L, and hepatitis C virus NS5B protein. Example RNA Reverse Transcriptases. A non-limiting example list to include are reverse transcriptases derived from Avian Myelomatosis Virus (AMV), Murine Moloney Leukemia Virus (MMLV) and/or the Human Immunodeficiency Virus (HIV), telomerase reverse transcriptases such as (hTERT), SuperScript™ III, SuperScript™ IV Reverse Transcriptase, ProtoScript® II Reverse Transcriptase.

As used herein, the term “primer” is defined as a polynucleotide to which nucleotides may be added via a free 3' OH group. A primer may include a 3' block inhibiting polymerization until the block is removed. A primer may include a modification at the 5' terminus to allow a coupling reaction or to couple the primer to another moiety. A primer may include one or more moieties, such as 8-oxo-G, which may be cleaved under suitable conditions, such as UV light, chemistry, enzyme, or the like. The primer length may be any suitable number of bases long and may include any suitable combination of natural and non-natural nucleotides. A target polynucleotide may include an “amplification adapter” or, more simply, an “adapter,” that hybridizes to (has a sequence that is complementary to) a primer, and may be amplified so as to generate a complementary copy polynucleotide by adding nucleotides to the free 3' OH group of the primer.

As used herein, the term “plurality” is intended to mean a population of two or more different members. Pluralities may range in size from small, medium, large, to very large. The size of small plurality may range, for example, from a few members to tens of members. Medium sized pluralities may range, for example, from tens of members to about 100 members or hundreds of members. Large pluralities may range, for example, from about hundreds of members to about 1000 members, to thousands of members and up to tens of thousands of members. Very large pluralities may range, for example, from tens of thousands of members to about hundreds of thousands, a million, millions, tens of millions and up to or greater than hundreds of millions of members. Therefore, a plurality may range in size from two to well over one hundred million members as well as all sizes, as measured by the number of members, in between and greater than the above example ranges. Accordingly, the definition of the term is intended to include all integer values greater than two.

As used herein, the term “double-stranded,” when used in reference to a polynucleotide, is intended to mean that all or substantially all of the nucleotides in the polynucleotide are hydrogen bonded to respective nucleotides in a complementary polynucleotide. A double-stranded polynucleotide also may be referred to as a “duplex.”

As used herein, the term “single-stranded,” when used in reference to a polynucleotide, means that essentially none of the nucleotides in the polynucleotide are hydrogen bonded to a respective nucleotide in a complementary polynucleotide.

As used herein, the term “target polynucleotide” is intended to mean a polynucleotide that is the object of an analysis or action, and may also be referred to using terms such as “library polynucleotide,” “template polynucleotide,” or “library template.” The analysis or action includes subjecting the polynucleotide to amplification, sequencing and/or other procedure. A target polynucleotide may include nucleotide sequences additional to a target sequence to be analyzed. For example, a target polynucleotide may include one or more adapters, including an amplification adapter that functions as a primer binding site, that flank(s) a target polynucleotide sequence that is to be analyzed. In particular examples, target polynucleotides may have different sequences than one another but may have first and second adapters that are the same as one another. The two adapters that may flank a particular target polynucleotide sequence may have the same sequence as one another, or complementary sequences to one another, or the two adapters may have different sequences. Thus, species in a plurality of target polynucleotides may include regions of known sequence that flank regions of unknown sequence that are to be evaluated by, for example, sequencing (e.g., SBS). In some examples, target polynucleotides carry an amplification adapter at a single end, and such adapter may be located at either the 3' end or the 5' end the target polynucleotide. Target polynucleotides may be used without any adapter, in which case a primer binding sequence may come directly from a sequence found in the target polynucleotide.

The terms “polynucleotide” and “oligonucleotide” are used interchangeably herein. The different terms are not intended to denote any particular difference in size, sequence, or other property unless specifically indicated otherwise. For clarity of description, the terms may be used to distinguish one species of polynucleotide from another when describing a particular method or composition that includes several polynucleotide species.

As used herein, the term “substrate” refers to a material used as a support for compositions described herein. Example substrate materials may include glass, silica, plastic, quartz, metal, metal oxide, organo-silicate (e.g., polyhedral organic silsesquioxanes (POSS)), polyacrylates, tantalum oxide, complementary metal oxide semiconductor (CMOS), or combinations thereof. An example of POSS can be that described in Kehagias et al., Microelectronic Engineering 86 (2009), pp. 776-778, which is incorporated by reference in its entirety. In some examples, substrates used in the present application include silica-based substrates, such as glass, fused silica, or other silica-containing material. In some examples, silica-based substrates can include silicon, silicon dioxide, silicon nitride, or silicone hydride. In some examples, substrates used in the present application include plastic materials or components such as polyethylene, polystyrene, poly(vinyl chloride), polypropylene, nylons, polyesters, polycarbonates, and poly(methyl methacrylate). Example plastics materials include poly(methyl methacrylate), polystyrene, and cyclic olefin polymer substrates. In some examples, the substrate is or includes a silica-based material or plastic material or a combination thereof. In particular examples, the substrate has at least one surface including glass or a silicon-based polymer. In some examples, the substrates can include a metal. In some such examples, the metal is gold. In some examples, the substrate has at least one surface including a metal oxide. In one example, the surface includes a tantalum oxide or tin oxide. Acrylamides, enones, or acrylates may also be utilized as a substrate material or component. Other substrate materials can include, but are not limited to gallium arsenide, indium phosphide, aluminum, ceramics, polyimide, quartz, resins, polymers and copolymers. In some examples, the substrate and/or the substrate surface can be, or include, quartz. In some other examples, the substrate and/or the substrate surface can be, or include, semiconductor, such as GaAs or ITO. The foregoing lists are intended to be illustrative of, but not limiting to the present application. Substrates can include a single material or a plurality of different materials. Substrates can be composites or laminates. In some examples, the substrate includes an organo-silicate material.

Substrates can be flat, round, spherical, rod-shaped, or any other suitable shape. Substrates may be rigid or flexible. In some examples, a substrate is a bead or a flow cell.

Substrates can be non-patterned, textured, or patterned on one or more surfaces of the substrate. In some examples, the substrate is patterned. Such patterns may include posts, pads, wells, ridges, channels, or other three-dimensional concave or convex structures. Patterns may be regular or irregular across the surface of the substrate. Patterns can be formed, for example, by nanoimprint lithography or by use of metal pads that form features on non-metallic surfaces, for example.

In some examples, a substrate described herein forms at least part of a flow cell or is located in or coupled to a flow cell. Flow cells may include a flow chamber that is divided into a plurality of lanes or a plurality of sectors. Example flow cells and substrates for manufacture of flow cells that can be used in methods and compositions set forth herein include, but are not limited to, those commercially available from Illumina, Inc. (San Diego, CA).

As used herein, the term “electrode” is intended to mean a solid structure that conducts electricity. Electrodes may include any suitable electrically conductive material, such as gold, palladium, silver, or platinum, or combinations thereof. In some examples, an electrode may be disposed on a substrate. In some examples, an electrode may define a substrate.

As used herein, the term “nanopore” is intended to mean a structure that includes an aperture that permits molecules to cross therethrough from a first side of the nanopore to a second side of the nanopore, in which a portion of the aperture of a nanopore has a width of 100 nm or less, e.g., 10 nm or less, or 2 nm or less. The aperture extends through the first and second sides of the nanopore. Molecules that can cross through an aperture of a nanopore can include, for example, ions or water-soluble molecules such as amino acids or nucleotides. The nanopore can be disposed within a membrane, or can be provided through a substrate. Optionally, a portion of the aperture can be narrower than one or both of the first and second sides of the nanopore, in which case that portion of the aperture can be referred to as a “constriction.” Alternatively or additionally, the aperture of a nanopore, or the constriction of a nanopore (if present), or both, can be greater than 0.1 nm, 0.5 nm, 1 nm, 10 nm or more. A nanopore can include multiple constrictions, e.g., at least two, or three, or four, or five, or more than five constrictions. nanopores include biological nanopores, solid-state nanopores, or biological and solid-state hybrid nanopores.

Biological nanopores include, for example, polypeptide nanopores and polynucleotide nanopores. A “polypeptide nanopore” is intended to mean a nanopore that is made from one or more polypeptides. The one or more polypeptides can include a monomer, a homopolymer or a heteropolymer. Structures of polypeptide nanopores include, for example, an α-helix bundle nanopore and a β-barrel nanopore as well as all others well known in the art. Example polypeptide nanopores include aerolysin, α-hemolysin, *Mycobacterium smegmatis* porin A, gramicidin A, maltoporin, OmpF, OmpC, PhoE, Tsx, F-pilus, SP1, mitochondrial porin (VDAC), Tom40, outer membrane phospholipase A, CsgG, and *Neisseria* autotransporter lipoprotein (NalP). *Mycobacterium smegmatis* porin A (MspA) is a membrane porin produced by Mycobacteria, allowing hydrophilic molecules to enter the bacterium. MspA forms a tightly interconnected octamer and transmembrane beta-barrel that resembles a goblet and includes a central constriction. For further details regarding α-hemolysin, see U.S. Pat. No. 6,015,714, the entire contents of which are incorporated by reference herein. For further details regarding SP1, see Wang et al., Chem. Commun., 49:1741-1743 (2013), the entire contents of which are incorporated by reference herein. For further details regarding MspA, see Butler et al., "Single-molecule DNA detection with an engineered MspA protein nanopore," Proc. Natl. Acad. Sci. 105: 20647-20652 (2008) and Derrington et al., "Nanopore DNA sequencing with MspA," Proc. Natl. Acad. Sci. USA, 107:16060-16065 (2010), the entire contents of both of which are incorporated by reference herein. Other nanopores include, for example, the MspA homolog from *Nocardia farcinica*, and lysenin. For further details regarding lysenin, see PCT Publication No. WO 2013/153359, the entire contents of which are incorporated by reference herein.

A "polynucleotide nanopore" is intended to mean a nanopore that is made from one or more nucleic acid polymers. A polynucleotide nanopore can include, for example, a polynucleotide origami.

A "solid-state nanopore" is intended to mean a nanopore that is made from one or more materials that are not of biological origin. A solid-state nanopore can be made of inorganic or organic materials. Solid-state nanopores include, for example, silicon nitride (SiN), silicon dioxide ($SiO_2$), silicon carbide (SiC), hafnium oxide ($HfO_2$), molybdenum disulfide ($MoS_2$), hexagonal boron nitride (h-BN), or graphene. A solid-state nanopore may comprise an aperture formed within a solid-state membrane, e.g., a membrane including any such material(s).

A "biological and solid-state hybrid nanopore" is intended to mean a hybrid nanopore that is made from materials of both biological and non-biological origins. Materials of biological origin are defined above and include, for example, polypeptides and polynucleotides. A biological and solid-state hybrid nanopore includes, for example, a polypeptide-solid-state hybrid nanopore and a polynucleotide-solid-state nanopore.

As used herein, a "barrier" is intended to mean a structure that normally inhibits passage of molecules from one side of the barrier to the other side of the barrier. The molecules for which passage is inhibited can include, for example, ions and water-soluble molecules such as nucleotides or amino acids. However, if a nanopore is disposed within a barrier, then the aperture of the nanopore may permit passage of molecules from one side of the barrier to the other side of the barrier. As one specific example, if a nanopore is disposed within a barrier, the aperture of the nanopore may permit passage of molecules from one side of the barrier to the other side of the barrier. Barriers include membranes of biological origin, such as lipid bilayers, and non-biological barriers such as solid-state membranes or substrates.

As used herein, "of biological origin" refers to material derived from or isolated from a biological environment such as an organism or cell, or a synthetically manufactured version of a biologically available structure.

As used herein, "solid-state" refers to material that is not of biological origin.

As used herein, "synthetic" refers to a membrane material that is not of biological origin (e.g., polymeric materials, synthetic phospholipids, solid-state membranes, or combinations thereof).

As used herein, a "polymeric membrane" or a "polymer membrane" refers to a synthetic barrier that primarily is composed of a polymer that is not of biological origin. In some examples, a polymeric membrane consists essentially of a polymer that is not of biological origin. A block copolymer is an example of a polymer that is not of biological origin and that may be included in the present barriers. A hydrophobic polymer with ionic end groups is another example of a polymer that is not of biological origin and that may be included in the present barriers. Because the present barriers relate to polymers that are not of biological origin, the terms "polymeric membrane," "polymer membrane," "membrane," and "barrier" may be used interchangeably herein when referring to the present barriers, even though the terms "barrier" and "membrane" generally may encompass other types of materials as well.

As used herein, the term "block copolymer" is intended to refer to a polymer having at least a first portion or "block" that includes a first type of monomer, and at least a second portion or "block" that is coupled directly or indirectly to the first portion and includes a second, different type of monomer. The first portion may include a polymer of the first type of monomer, or the second portion may include a polymer of the second type of monomer, or the first portion may include a polymer of the first type of monomer and the second portion may include a polymer of the second type of monomer. The first portion optionally may include an end group with a hydrophilicity that is different than that of the first type of monomer, or the second portion optionally may include an end group with a hydrophilicity that is different than that of the second type of monomer, or the first portion optionally may include an end group with a hydrophilicity that is different than that of the first type of monomer and the second portion optionally may include an end group with a hydrophilicity that is different than that of the second type of monomer. The end groups of any hydrophilic blocks may be located at an outer surface of a barrier formed using such hydrophilic blocks. Depending on the particular configuration, the end groups of any hydrophobic blocks may be located at an inner surface of the barrier or at an outer surface of a barrier formed using such hydrophobic blocks.

Block copolymers include, but are not limited to, diblock copolymers and triblock copolymers.

A "diblock copolymer" is intended to refer to a block copolymer that includes, or consists essentially of, first and second blocks coupled directly or indirectly to one another. The first block may be hydrophilic and the second block may be hydrophobic, in which case the diblock copolymer may be referred to as an "AB" copolymer where "A" refers to the hydrophilic block and "B" refers to the hydrophobic block.

A "triblock copolymer" is intended to refer to a block copolymer that includes, or consists essentially of, first, second, and third blocks coupled directly or indirectly to one another. The first and third blocks may include, or may consist essentially of, the same type of monomer as one another, and the second block may include a different type of monomer. In some examples, the first block may be hydrophobic, the second block may be hydrophilic, and the third block may be hydrophobic and includes the same type of monomer as the first block, in which case the triblock copolymer may be referred to as a "BAB" copolymer where "A" refers to the hydrophilic block and "B" refers to the hydrophobic blocks. In other examples, the first block may be hydrophilic, the second block may be hydrophobic, and the third block may be hydrophilic and includes the same type of monomer as the first block, in which case the triblock copolymer may be referred to as an "ABA" copolymer where "A" refers to the hydrophilic blocks and "B" refers to the hydrophobic block.

The particular arrangement of molecules of polymer chains (e.g., block copolymers) within a polymeric membrane may depend, among other things, on the respective block lengths, the type(s) of monomers used in the different blocks, the relative hydrophilicities and hydrophobicities of the blocks, the composition of the fluid(s) within which the membrane is formed, and/or the density of the polymeric chains within the membrane. During formation of the membrane, these and other factors generate forces between molecules of the polymeric chains which laterally position and reorient the molecules in such a manner as to substantially minimize the free energy of the membrane. The membrane may be considered to be substantially "stable" once the polymeric chains have completed these rearrangements, even though the molecules may retain some fluidity of movement within the membrane.

An "A-B interface" of a block copolymer (such as a diblock or triblock copolymer) refers to the interface at which the hydrophilic block is coupled to the hydrophobic block.

As used herein, the term "hydrophobic" is intended to mean tending to exclude water molecules. Hydrophobicity is a relative concept relating to the polarity difference of molecules relative to their environment. Non-polar (hydrophobic) molecules in a polar environment will tend to associate with one another in such a manner as to reduce contact with polar (hydrophilic) molecules to a minimum to lower the free energy of the system as a whole.

As used herein, the term "hydrophilic" is intended to mean tending to bond to water molecules. Polar (hydrophilic) molecules in a polar environment will tend to associate with one another in such a manner as to reduce contact with non-polar (hydrophobic) molecules to a minimum to lower the free energy of the system as a whole.

As used herein, the term "amphiphilic" is intended to mean having both hydrophilic and hydrophobic properties. For example, a block copolymer that includes a hydrophobic block and a hydrophilic block may be considered to be "amphiphilic." Illustratively, AB copolymers, ABA copolymers, and BAB copolymers all may be considered to be amphiphilic. Additionally, molecules including a hydrophobic polymer coupled to ionic end groups may be considered to be amphiphilic.

As used herein, a "solution" is intended to refer to a homogeneous mixture including two or more substances. In such a mixture, a solute is a substance which is uniformly dissolved in another substance referred to as a solvent. A solution may include a single solute, or may include a plurality of solutes. Additionally, or alternatively, a solution may include a single solvent, or may include a plurality of solvents. An "aqueous solution" refers to a solution in which the solvent is, or includes, water.

A first liquid that forms a homogeneous mixture with a second liquid is referred to herein as being "miscible" or "soluble" with the second liquid.

As used herein, the term "electroporation" means the application of a voltage across a membrane such that a nanopore is inserted into the membrane.

As used herein, terms such as "cross-linked" and "cross-linking" refer to the forming of a bond between molecules. The bond may include a covalent bond or a non-covalent bond, such as an ionic bond, a hydrogen bond, or π-π stacking. The molecules which are cross-linked may include polymers, proteins, or polymers and proteins.

As used herein, the term "initiator" is intended to mean an entity that can initiate a polymerization reaction. Nonlimiting examples of initiators include moieties, molecules, and/or photons that can initiate a polymerization reaction.

As used herein, terms such as "covalently coupled" or "covalently bonded" refer to the forming of a chemical bond that is characterized by the sharing of pairs of electrons between atoms. For example, a covalently coupled molecule refers to a molecule that forms a chemical bond, as opposed to a non-covalent bond such as electrostatic interaction.

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" or "$C_{1-4}$alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means fluorine, chlorine, bromine, or iodine, with fluorine and chlorine being examples.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" or "$C_{1-4}$alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2-dienyl, and buta-1,2-dien-4-yl. Typical alkenyl groups include, but are in no way limited to, ethenyl, propenyl, butenyl, pentenyl, and hexenyl, and the like.

Groups that include an alkenyl group include optionally substituted alkenyl, cycloalkenyl, and heterocycloalkenyl groups.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" or "$C_{2-4}$alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

Groups that include an alkynyl group include optionally substituted alkynyl, cycloalkynyl, and heterocycloalkynyl groups.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some examples, the aryl group has 6 to 10 carbon atoms. The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "heterocycle" refers to a cyclic compound which includes atoms of carbon along with another atom (heteroatom), for example nitrogen, oxygen or sulfur. Heterocycles may be aromatic (heteroaryl) or aliphatic. An aliphatic heterocycle may be completely saturated or may contain one or more or two or more double bonds, for example the heterocycle may be a heterocycloalkyl. The heterocycle may include a single heterocyclic ring or multiple heterocyclic rings that are fused.

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some examples, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinolinyl, benzimidazolyl, benzoxazolyl, benzothiazolyl, indolyl, isoindolyl, and benzothienyl.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" or "cycloalkene" means a carbocyclyl ring or ring system having at least one double bond, wherein no ring in the ring system is aromatic. An example is cyclohexenyl or cyclohexene. Another example is norbornene or norbornenyl.

As used herein, "heterocycloalkenyl" or "heterocycloalkene" means a carbocyclyl ring or ring system with at least one heteroatom in ring backbone, having at least one double bond, wherein no ring in the ring system is aromatic. In some examples, heterocycloalkenyl or heterocycloalkene ring or ring system is 3-membered, 4-membered, 5-membered, 6-membered, 7-membered, 8-membered, 9-membered, or 10-membered.

As used herein, "cycloalkynyl" or "cycloalkyne" means a carbocyclyl ring or ring system having at least one triple bond, wherein no ring in the ring system is aromatic. An example is cyclooctyne. Another example is bicyclononyne. Another example is dibenzocyclooctyne (DBCO).

As used herein, "heterocycloalkynyl" or "heterocycloalkyne" means a carbocyclyl ring or ring system with at least one heteroatom in ring backbone, having at least one triple bond, wherein no ring in the ring system is aromatic. In some examples, heterocycloalkynyl or heterocycloalkyne ring or ring system is 3-membered, 4-membered, 5-membered, 6-membered, 7-membered, 8-membered, 9-membered, or 10-membered.

As used herein, "heterocycloalkyl" means a non-aromatic cyclic ring or ring system containing at least one heteroatom in the ring backbone. Heterocycloalkyls may be joined together in a fused, bridged or spiro-connected fashion. Heterocycloalkyls may have any degree of saturation provided that at least one heterocyclic ring in the ring system is not aromatic. The heterocycloalkyl group may have 3 to 20 ring members (i.e., the number of atoms making up the ring backbone, including carbon atoms and heteroatoms), although the present definition also covers the occurrence of the term "heterocycloalkyl" where no numerical range is designated. The heterocycloalkyl group may also be a medium size heterocycloalkyl having 3 to 10 ring members. The heterocycloalkyl group could also be a heterocycloalkyl having 3 to 6 ring members. The heterocycloalkyl group may be designated as "3-6 membered heterocycloalkyl" or similar designations. In some six membered monocyclic heterocycloalkyls, the heteroatom(s) are selected from one up to three of O, N or S, and in some five membered monocyclic heterocycloalkyls, the heteroatom(s) are selected from one or two heteroatoms selected from O, N, or S. Examples of heterocycloalkyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —$CF_3$), halo($C_1$-$C_6$)alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (═O). Wherever a group is described as "optionally substituted" that group can be substituted with the above substituents.

Where the compounds disclosed herein have at least one stereocenter, they may exist as individual enantiomers or diastereomers, or as mixtures of such isomers, including racemates. Separation of the individual isomers or selective synthesis of the individual isomers is accomplished by application of various methods which are well known to practitioners in the art. Where compounds disclosed herein are understood to exist in tautomeric forms, all tautomeric forms are included in the scope of the structures depicted. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents. Unless otherwise indicated, such solvates are included in the scope of the compounds disclosed herein.

As used herein, the term "adduct" is intended to mean the product of a chemical reaction between two or more molecules, where the product contains all of the atoms of the molecules that were reacted.

As used herein, the term "linker" is intended to mean a molecule or molecules via which one element is attached to another element. For example, a linker may attach a first reactive moiety to a second reactive moiety. Linkers may be covalent, or may be non-covalent. Nonlimiting examples of covalent linkers include alkyl chains, polyethers, amides, esters, aryl groups, polyaryls, and the like. Nonlimiting examples of noncovalent linkers include host-guest complexation, cyclodextrin/norbornene, adamantane inclusion complexation with β-CD, DNA hybridization interactions, streptavidin/biotin, and the like.

As used herein, the term "barrier support" is intended to refer to a structure that can suspend a barrier. In examples in which a barrier support is used to support a polymeric membrane, the barrier support may be referred to as a "membrane support." A barrier support may define an aperture, such that a first portion of the barrier is suspended across the aperture, and a second portion of the barrier is disposed on, and supported by, the barrier. The barrier support may include any suitable arrangement of elements to define an aperture and suspend the barrier across the aperture. In some examples, a barrier support may include a substrate having an aperture defined therethrough, across which aperture the barrier may be suspended. Additionally, or alternatively, the barrier support may include one or more first features (such as one or more lips or ledges of a well within a substrate) that are raised relative to one or more second features (such as a bottom surface of the well), wherein a height difference between (a) the one or more first features and (b) the one or more second features defines an aperture across which a barrier may be suspended. The aperture may have any suitable shape, such as a circle, an oval, a polygon, or an irregular shape. The barrier support may include any suitable material or combination of materials. For example, the barrier support may be of biological origin, or may be solid state. Some examples, the barrier support may include, or may consist essentially of, an organic material, e.g., a curable resin such as SU-8; polytetrafluoroethylene (PTFE), poly(methyl methacrylate) (PMMA), parylene, or the like. Additionally, or alternatively, various examples, the barrier support may include, or may consist essentially of, an inorganic material, e.g., silicon nitride, silicon oxide, or molybdenum disulfide.

As used herein, the term "annulus" is intended to refer to a liquid that is adhered to a barrier support, located within a barrier, and extends partially into an aperture defined by the barrier support. As such, it will be understood that the annulus may follow the shape of the aperture of the barrier, e.g., may have the shape of a circle, an oval, a polygon, or an irregular shape.

Barriers Including Cross-Linked Amphiphilic Molecules, and Methods of Making the Same Barrier including cross-linked amphiphilic molecules, and methods of making the same, now will be described with reference to FIGS. 1-16, 28-31, and 38.

FIG. 1 schematically illustrates a cross-sectional view of an example nanopore composition and device 100 including a polymeric membrane. Device 100 includes fluidic well 100' including barrier 101, such as a polymeric membrane, having first (trans) side 111 and second (cis) side 112, first fluid 120 within fluidic well 100' and in contact with first side 111 of the membrane, and second fluid 120' within the fluidic well and in contact with the second side 112 of the membrane. Barrier 101 may have any suitable structure that normally inhibits passage of molecules from one side of the membrane to the other side of the membrane, e.g., that normally inhibits contact between fluid 120 and fluid 120'. Illustratively, barrier 101 may include a polymeric membrane, which may include a diblock or triblock copolymer and may have a structure such as described in greater detail below with reference to FIGS. 2A-2B, 3A-3D, 4, 5A-5B, 6A-6B, 7A-7B, 8A-8B, 9A-9B, 10A-10B, 11A-11B, 12A-12C, 13, 14A-14B, 15A-15C, and 28-31.

First fluid 120 may have a first composition including a first concentration of a salt 160, which salt may be represented for simplicity as positive ions although it will be appreciated that counterions also may be present. Second fluid 120' may have a second composition including a second concentration of the salt 160 that may be the same as, or different, than the first concentration. Any suitable salt or salts 160 may be used in first and second fluids 120, 120', e.g., ranging from common salts to ionic crystals, metal complexes, ionic liquids, or even water-soluble organic ions. For example, the salt may include any suitable combination of cations (such as, but not limited to, H, Li, Na, K, $NH_4$, Ag, Ca, Ba, and/or Mg) with any suitable combination of anions (such as, but not limited to, OH, Cl, Br, I, $NO_3$, $ClO_4$, F, $SO_4$, and/or $CO_3^{2-}$ . . . ). In one nonlimiting example, the salt includes potassium chloride (KCl). It will also be appreciated that the first and second fluids optionally may include any suitable combination of other solutes. Illustratively, first and second fluids 120, 120' may include an aqueous buffer (such as N-(2-hydroxyethyl)piperazine-N'-2-ethanesulfonic acid (HEPES), commercially available from Fisher BioReagents).

Still referring to FIG. 1 device 100 further may include nanopore disposed within membrane 101 and providing aperture 113 fluidically coupling first side 111 to second side 112. As such, aperture 113 of nanopore 110 may provide a pathway for fluid 120 and/or fluid 120' (e.g., salt 160) to flow through membrane 101. Nanopore 110 may include a solid-state nanopore, a biological nanopore (e.g., MspA such as illustrated in FIG. 1), or a biological and solid-state hybrid nanopore. Nonlimiting examples and properties of membranes and nanopores are described elsewhere herein, as well as in U.S. Pat. No. 9,708,655, the entire contents of which are incorporated by reference herein. In a manner such as illustrated in FIG. 1, device 100 optionally may include first electrode 102 in contact with first fluid 120, second electrode 103 in contact with second fluid 120', and circuitry 180 in operable communication with the first and second electrodes and configured to detect changes in an electrical characteristic of the aperture. Such changes may, for example, be responsive to any suitable stimulus. Indeed, it will be appreciated that the present methods, compositions, and devices may be used in any suitable application or context, including any suitable method or device for sequencing, e.g., polynucleotide sequencing.

Figure 2A:
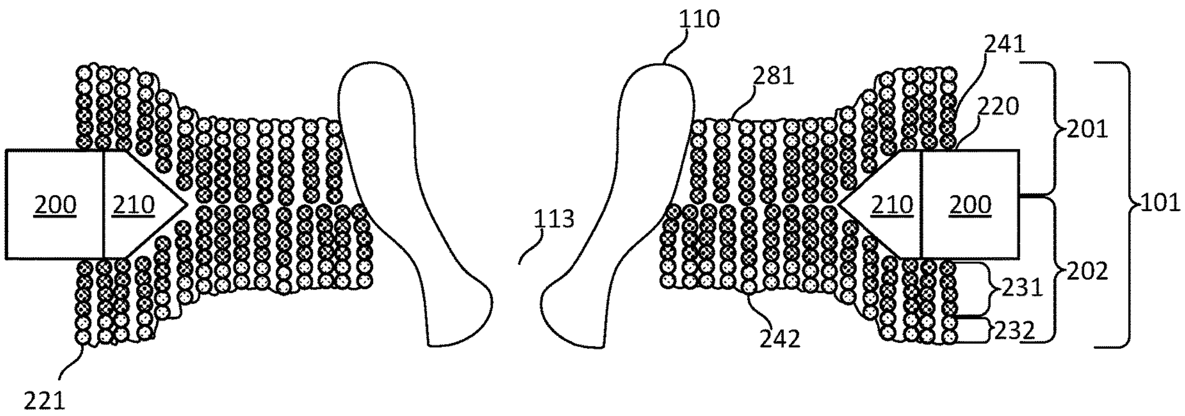
FIGS. 2A-2B schematically illustrate plan and cross-sectional views of further details of the nanopore composition and device of FIG. 1.
Figure 2B:
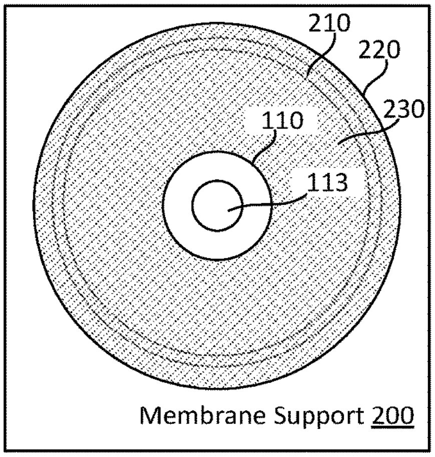

In some examples, polymeric membrane 101 between first and second fluids 120, 120' includes a block copolymer. For example, FIGS. 2A-2B schematically illustrate plan and cross-sectional views of further details of the nanopore composition and device of FIG. 1. As illustrated in FIG. 2A, membrane 101 may include first layer 201 including a first plurality of amphiphilic molecules 221 and second layer 202 including a second plurality of the amphiphilic molecules contacting the first plurality of amphiphilic molecules. In the nonlimiting example illustrated in FIG. 2A, the copolymer is a diblock copolymer (AB), such that each molecule 221 includes a hydrophobic "B" block 231 (within which circles 241 with darker fill represent hydrophobic monomers) and a hydrophilic "A" block 232 (within which circles 242 with lighter fill represent hydrophilic monomers) coupled directly or indirectly thereto. In other examples such as will be described with reference to FIGS. 5A-5B, 8A-8B, and 13, the copolymer instead may include an ABA triblock copolymer. In still other examples such as will be described with reference to FIGS. 6A-6B, 9A-9B, 11A-11B, and 14A-14B, the copolymer instead may include a BAB triblock copolymer.

In the example illustrated in FIG. 2A, the hydrophilic blocks 232 of the first plurality of molecules 221 are cross-linked to one another by bonds 281 at a first outer surface of membrane 101, e.g., the surface of membrane 101 contacting fluid 120 on first side 111. The hydrophilic blocks 232 of the second plurality of molecules 221 optionally also may be cross-linked to one another by bonds 281 at a second outer surface of membrane 101, e.g., the surface of membrane 101 contacting fluid 120' on second side 112. As such, bonds 281 may strengthen and stabilize the membrane, resulting in improved performance and durability. The hydrophobic blocks 231 of the first and second pluralities of molecules 221 may contact one another within the membrane. Although FIG. 2A illustrates an example in which the hydrophilic blocks are cross-linked by bonds 281 which are formed in respective planes at the ends of the hydrophilic blocks, such cross-linking bonds may be formed in any other suitable plane or planes within the membrane. For example, in a manner such as described with reference to FIGS. 10A-10B, 11A-11B, and 14A-14B, hydrophobic blocks 231 may be cross-linked by bonds which are formed in a plane or planes at the ends of the hydrophobic blocks. Or, for example, in a manner such as described with reference to FIGS. 7A-7B, 8A-8B, 9A-9B, and 13, the hydrophilic-hydrophobic (A-B) interfaces within the membrane may be cross-linked by bonds which are formed in respective planes at those interfaces.

In the example illustrated in FIGS. 2A-2B, membrane 101 may be suspended using a barrier support, e.g., membrane support 200 defining aperture 230. For example, membrane support 200 may include a substrate having an aperture 230 defined therethrough, e.g., a substantially circular aperture, or an aperture having another shape. Additionally, or alternatively, the barrier support may include one or more features of a well in which the nanopore device is formed, such as a lip or ledge on either side of the well. Nonlimiting examples of materials which may be included in a barrier support are provided further above. An annulus 210 including hydrophobic (non-polar) solvent, and which also may include polymer chains and/or other compound(s), may adhere to membrane support 200 and may support a portion of membrane 101, e.g., may be located within barrier 101 (here, between layer 201 and layer 202). Additionally, annulus 210 may taper inwards in a manner such as illustrated in FIG. 2A. An outer portion of the molecules 221 of membrane 101 may be disposed on support 200 (e.g., the portion extending between aperture 230 and membrane periphery 220), while an inner portion of the molecules may form a freestanding portion of membrane 101 (e.g., the portion within aperture 210, a part of which is supported by annulus 210). Note that although the overall assembly of molecules which are cross-linked to one another may itself be considered to form a larger molecule (e.g., a molecule which partially or substantially spans the aperture 230 of the membrane support 220 in FIGS. 2A-2B), the components of such larger molecule also may be referred to herein as molecules so as to facilitate discussion of such components.

Membrane 101 may be stabilized, and nanopore 110 may be inserted into the freestanding portion of membrane 101, e.g., using operations such as now will be described with reference to FIGS. 3A-3D, 4, 5A-5B, 6A-6B, 7A-7B, 8A-8B, 9A-9B, 10A-10B, 11A-11B, 12A-12C, 13, 14A-14B, 15A-15C, 16, 28-31, and 38. Although FIGS. 2A-2B illustrate nanopore 110 within barrier 101, it should be understood that the nanopore may be omitted, and that barrier 101 may be used for any suitable purpose. More generally, it should be appreciated that while the barriers described herein are particularly suitable for use with nanopores (e.g., for nanopore sequencing such as described with reference to FIGS. 32-36), the present barriers need not necessarily have nanopores inserted therein.

Figure 3A:
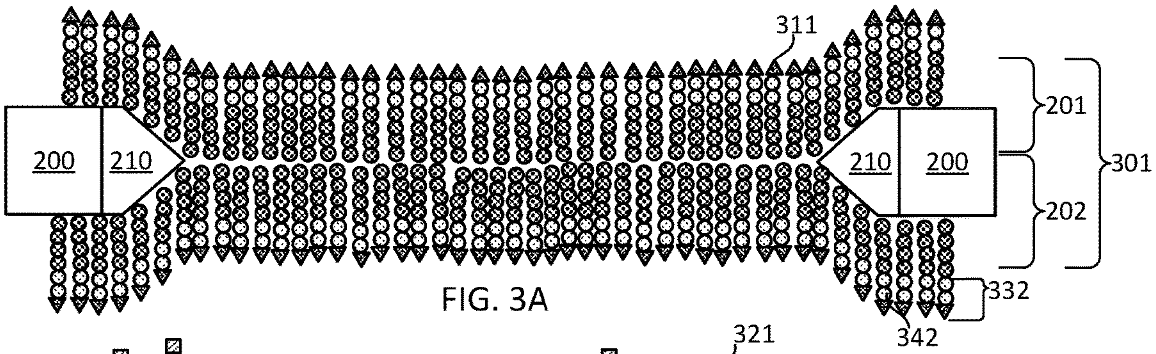
FIGS. 3A-3D schematically illustrate example operations for forming a barrier including crosslinked amphiphilic molecules.

FIGS. 3A-3D schematically illustrate example operations for forming a barrier including cross-linked amphiphilic molecules. FIG. 3A illustrates barrier 301 which may be suspended using membrane support 200 and optional annulus 210 in a manner similar to that described with reference to FIGS. 2A-2B. As illustrated in FIG. 3A, barrier 301 may be configured, in some regards, similarly as membrane 101 described with reference to FIGS. 2A-2B, e.g., may include layer 201 including a first plurality of amphiphilic molecules 221 and layer 202 including a second plurality of amphiphilic molecules 221. However, the amphiphilic molecules in barrier 301 have not yet been crosslinked. Instead, the amphiphilic molecules of layer 201 (and optionally also of layer 202) may include reactive moieties 311. Reactive moieties 311 may be reacted with one another in such a manner as to fully or partially cross-link the amphiphilic molecules 221 with one another. In examples such as illustrated in FIG. 3A, the amphiphilic molecules include molecules of a diblock copolymer which are oriented such that the hydrophobic "B" sections of the AB diblock copolymer are oriented towards each other and disposed within the membrane, while the hydrophilic "A" sections form the outer surfaces of the membrane. In the non-limiting example illustrated in FIG. 3A, hydrophilic "A" sections 332 may include reactive moieties 311, e.g., coupled to the terminal hydrophilic monomer 342. Suitable methods of forming membranes that are suspended by barrier supports are known in the art, such as "painting", e.g., brush painting (manual), mechanical painting (e.g., using stirring bar), and bubble painting (e.g., using flow through the device).

Figure 3B:
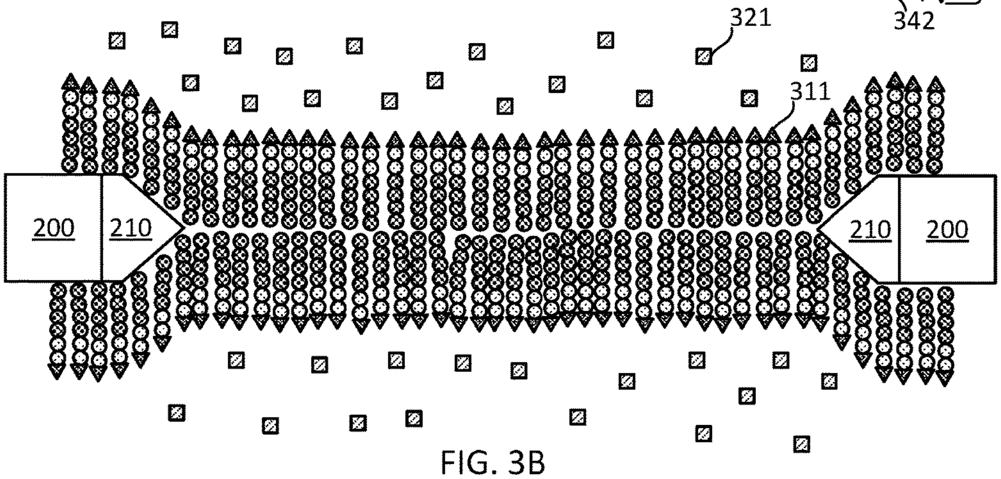

In some examples, as illustrated in FIG. 3B, barrier 301 may be contacted with a fluid in which initiator 321 is dissolved. Initiator 321 may be selected so as to be chemically reactive with reactive moieties 311, e.g., so as to form products in which amphiphilic molecules 221 are cross-linked to one another, such as via polymerization. In other examples, the initiator may be omitted and reactive moieties may react directly with one another without use of an initiator.

Figure 3C:
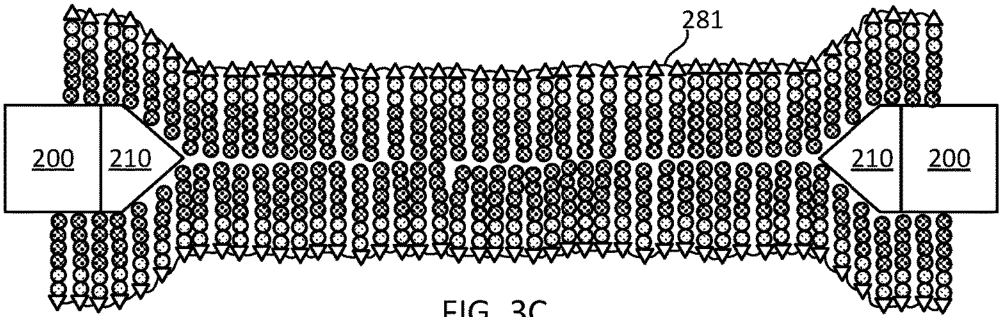

FIG. 3C illustrates the products of polymerization reactions between amphiphilic molecules 221, in which bonds 281 are formed between reactive moieties 311 (the fill of which is changed from crosshatched to white to indicate that such moieties have reacted and are no longer available for reaction). Although FIG. 3C may suggest that each reactive moiety 311 is cross-linked to two other moieties via respective bonds 281, it will be appreciated that each reactive moiety may form bonds with any suitable number of other such reactive moieties, e.g., one, two, three, or more than three other such reactive moieties. The relative proportion of such products may be controlled, e.g., through the type of reactive moieties used, the type of initiator used, reaction time, and the reaction conditions, so as to control the amount of cross-linking provided using reaction between the reactive moieties 311 of molecules 221. Cross-linking also may be controlled through coupling strategies. For example, thiol-ene or thiol-yne reactions may be used that are based on generating radicals and can be controlled with type and concentration of initiator. Cross-linking triggered by a reducing agent alternatively may be used and concentration and type of reducing agent can be used to control the reaction. Alternatively, an initiator free strategy may be used which uses UV light to trigger cross-linking, and the reaction can be controlled by UV dose (irradiance, wavelength and time); in such examples, the barrier may be enclosed within a structure which is at least partially transparent to the UV light. Other strategies may use two amphiphilic polymers with different reactive moiety, in which the ratio between the amphiphilic polymers may be selected to achieve substantially full cross-linking. Depending on the strategy, this substantially full cross-linking can be achieved with an example ratio of 1:1 or 2:1. If lower degree of cross-linking is desired, ratios can be tuned to achieve partial cross-linking. Additionally, in some examples, the amount of cross-linking may be controlled by mixing amphiphilic molecules 221 in suitable proportion with other amphiphilic molecules that do not include reactive moieties 311, or that include different reactive moieties, and/or that have a different architecture (e.g., AB can be mixed with ABA and/or BAB; ABA can be mixed with AB and/or BAB; and/or BAB can be mixed with AB and/or ABA).

Figure 3D:
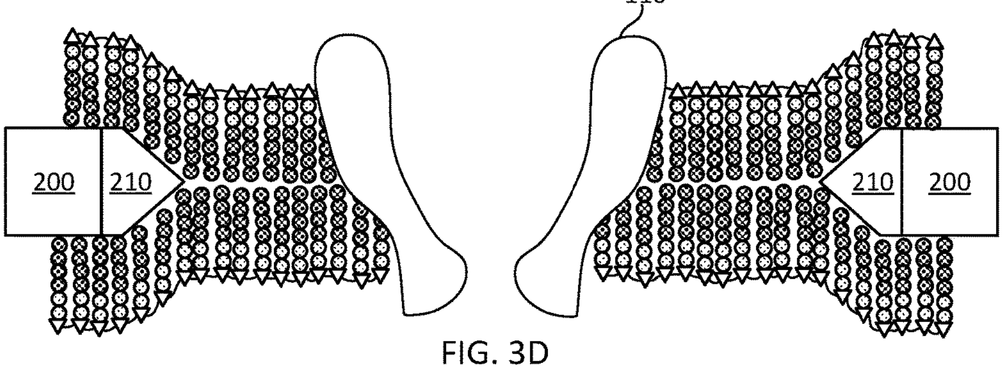
Figure 4:
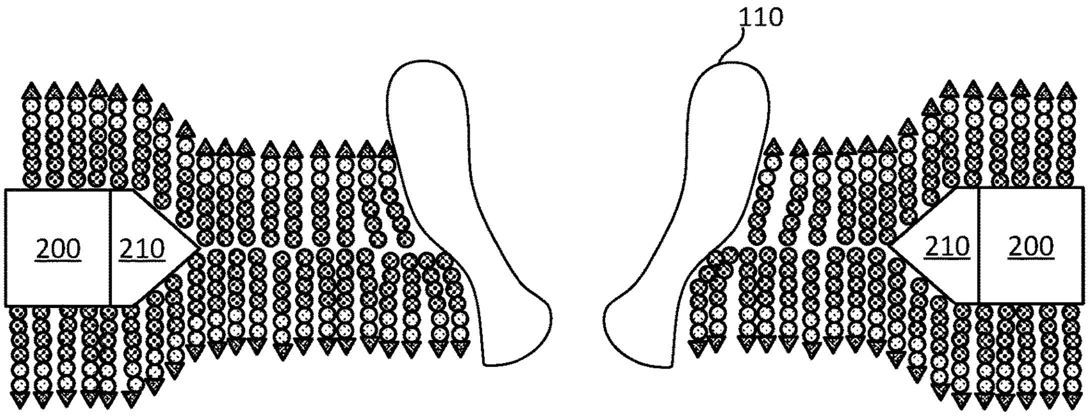
FIG. 4 schematically illustrates an alternative manner in which the operation described with reference to FIG. 3D may be performed.

In some examples, following cross-linking of amphiphilic molecules 221, nanopore 110 may be inserted into the barrier in a manner such as illustrated in FIG. 3D. FIG. 4 schematically illustrates an alternative manner in which the operation described with reference to FIG. 3D may be performed. More specifically, in the example illustrated in FIG. 4, nanopore 110 may be inserted into suspended barrier 301 before cross-linking the amphiphilic molecules within the barrier. The amphiphilic molecules then may be cross-linked in a manner such as described with reference to FIGS. 3A-3C. Nonlimiting examples of techniques for inserting nanopore 110 into the membrane, whether before or after crosslinking, include electroporation, pipette pump cycle, and detergent assisted nanopore insertion. Tools for forming membranes using synthetic polymers and inserting nanopores in the membranes are commercially available, such as the Orbit 16 TC platform available from Nanion Technologies Inc. (California, USA).

Figure 5A:
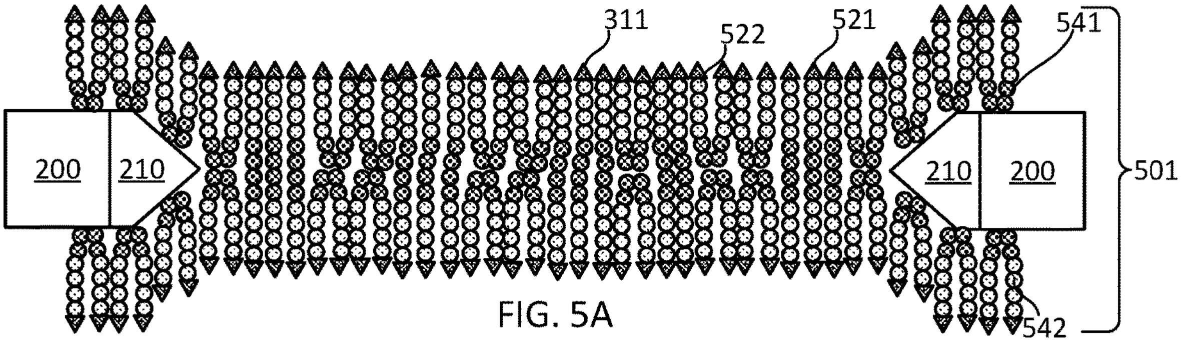
FIGS. 5A-5B schematically illustrate example operations for forming an alternative barrier including crosslinked amphiphilic molecules.
Figure 5B:
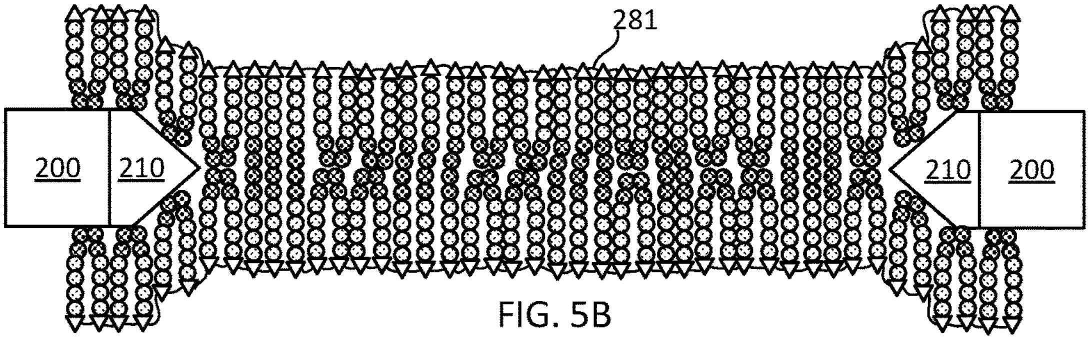

Although FIGS. 3A-3D illustrate operations for cross-linking the hydrophilic blocks of a diblock copolymer, it will be appreciated that such operations similarly may be used to cross-link other portions of a diblock copolymer or to cross-link other types of amphiphilic molecules, such as other types of polymers. FIGS. 5A-5B schematically illustrate example operations for forming an alternative barrier including crosslinked amphiphilic molecules. FIG. 5A illustrates suspended membrane 501 including molecules of an ABA triblock copolymer including hydrophobic "B" sections 541 coupled to and between hydrophilic "A" sections 542. Membrane 501 may be suspended using membrane support 200 and optional annulus 210 in a manner similar to that described with reference to FIGS. 2A-2B. Each individual ABA molecule may be in one of two arrangements. For example, ABA molecules 521 may extend through the layer in a linear fashion, with an "A" section on each side of the membrane and the "B" section in the middle of the membrane. Or, for example, ABA molecules 522 may extend to the middle of the membrane and then fold back on themselves, so that both "A" sections are on the same side of the membrane and the "B" section is in the middle of the membrane. Accordingly, in this example, barrier 501 may be considered to be partially a single layer and partially a bilayer. In other examples (not specifically illustrated) in which barrier 501 substantially includes molecules 521 which extend through the barrier in linear fashion, barrier 501 may substantially be a monolayer. In still other examples (not specifically illustrated) in which barrier 501 substantially includes molecules 522 which extend to approximately the middle of the barrier and then fold back on themselves, barrier 501 may substantially be a bilayer. Reactive moieties 311 may be coupled to hydrophilic sections 541, e.g., to the terminal hydrophilic monomer of such section. Reactive moieties 311 may be reacted with one another in a manner similar to that described with reference to FIGS. 3B-3C so as to cross-link molecules 521, 522 by forming bonds 281 illustrated in FIG. 5B. The nanopore may be inserted into the barrier at any suitable time, e.g., before cross-linking or after cross-linking.

Figure 6A:
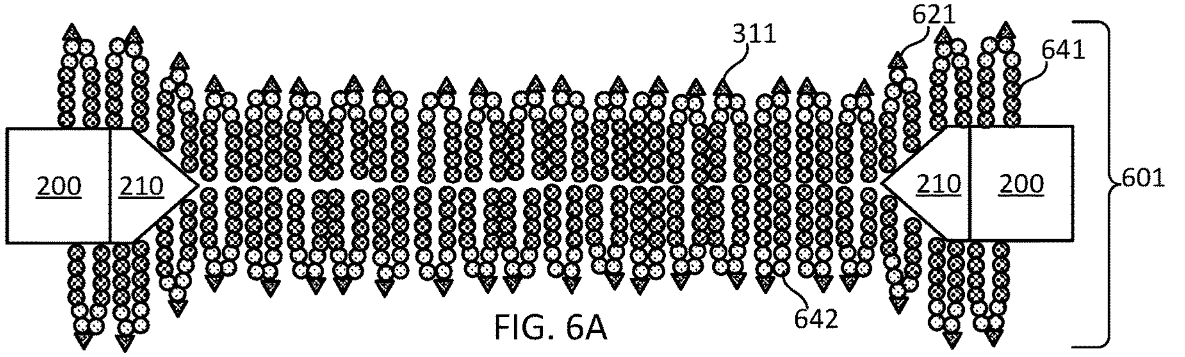
FIGS. 6A-6B schematically illustrate example operations for forming another alternative barrier including crosslinked amphiphilic molecules.
Figure 6B:
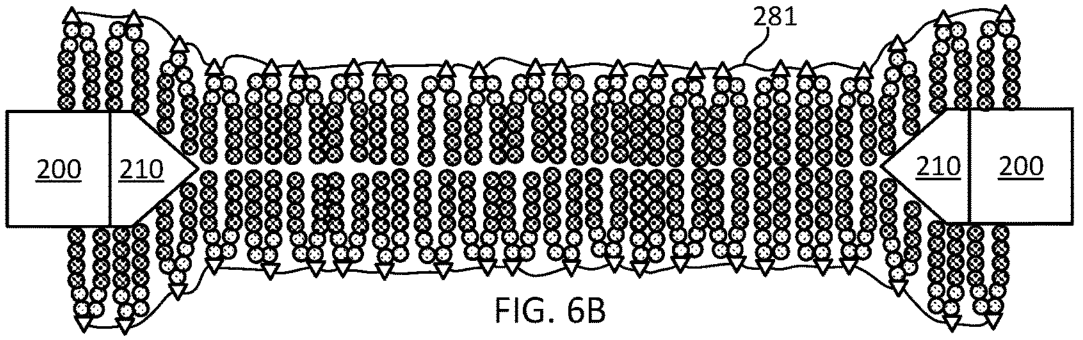

FIGS. 6A-6B schematically illustrate example operations for forming another alternative barrier including crosslinked amphiphilic molecules. FIG. 6A illustrates suspended membrane 601 including molecules 621 of a BAB triblock copolymer including hydrophilic "A" sections 642 coupled to and between hydrophobic "B" sections 641. Membrane 601 may be suspended using membrane support 200 and optional annulus 210 in a manner similar to that described with reference to FIGS. 2A-2B. In this example, membrane 601 may have a bilayer architecture with the "B" sections 641 oriented towards each other. The hydrophobic ends of the BAB molecules generally may located approximately in the middle of membrane 601, the molecules then extend towards either outer surface of the membranes, and then fold back on themselves. As such, both "B" sections are located in the middle of the membrane and the "A" section is on one side or the other of the membrane. Reactive moieties 311 may be coupled to hydrophilic sections 642, e.g., to one or more hydrophilic monomers of such section. In the example shown in FIG. 6B, reactive moieties 311 may be reacted with one another in a manner similar to that described with reference to FIGS. 3B-3C to cross-link molecules 621 via bonds 281. The nanopore may be inserted into the barrier at any suitable time, e.g., before cross-linking or after cross-linking.

Figure 7A:
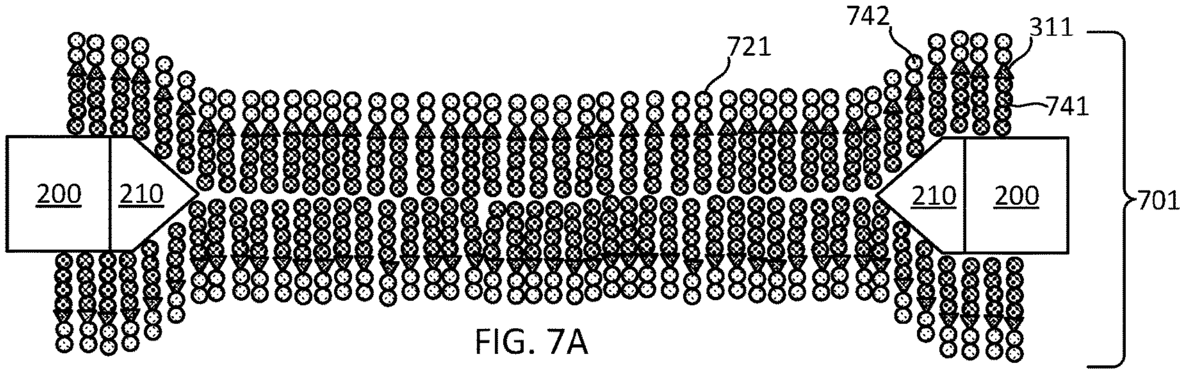
FIGS. 7A-7B schematically illustrate example operations for forming another alternative barrier including crosslinked amphiphilic molecules.
Figure 7B:
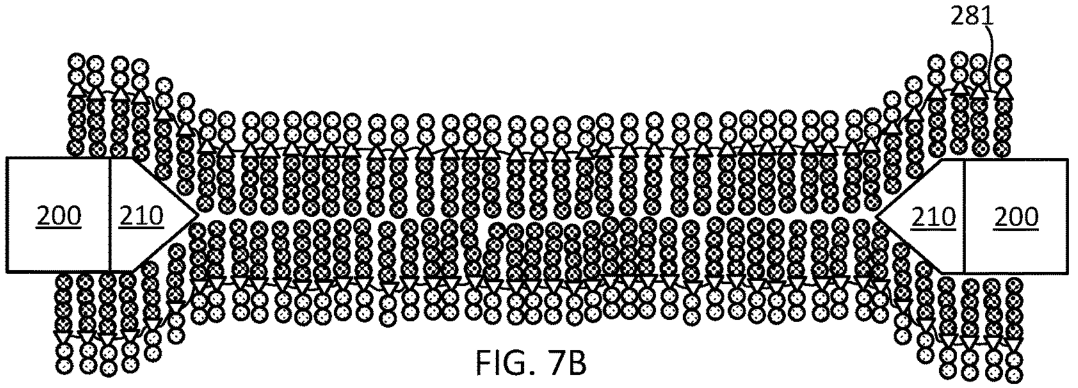

Although FIGS. 3A-3D, 4, 5A-5B, and 6A-6B illustrate the presence of reactive moieties at the ends of the hydrophilic A blocks on both sides of the suspended barrier, it will be appreciated that such reactive moieties may be provided at any suitable locations within the barrier and reacted so as to cross-link the amphiphilic molecules at such locations. For example, the reactive moiety may be located at an A-B interface. Illustratively, FIGS. 7A-7B schematically illustrate example operations for forming another alternative barrier including crosslinked amphiphilic molecules. Suspended barrier 701 illustrated in FIG. 7A includes AB diblock copolymer molecules 721 in which reactive moiety 311 is located at the A-B interface between hydrophilic block 742 and hydrophobic block 741. Barrier 701 may be suspended using membrane support 200 and optional annulus 210 in a manner similar to that described with reference to FIGS. 2A-2B. In a manner such as described with reference to FIGS. 3B-3C, reactive moieties 311 may be reacted so as to cross-link amphiphilic molecules 721 via bonds 281 as illustrated in FIG. 7B.

Figure 8A:
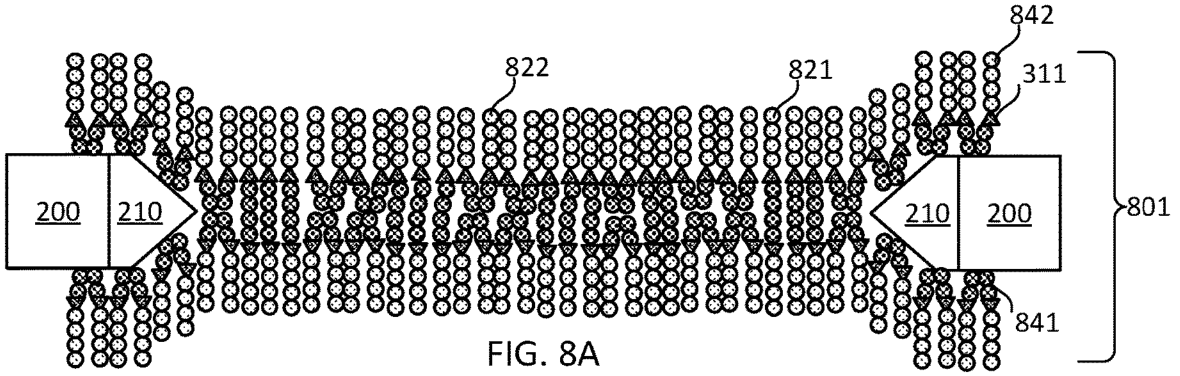
FIGS. 8A-8B schematically illustrate example operations for forming another alternative barrier including crosslinked amphiphilic molecules.
Figure 8B:
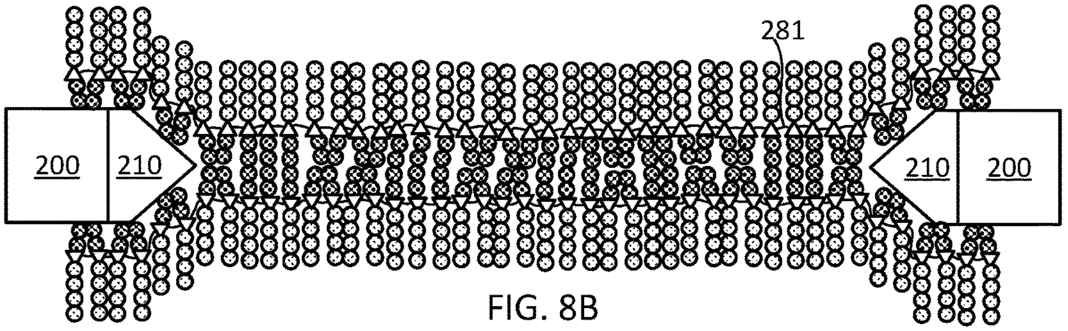

Or, for example, FIGS. 8A-8B schematically illustrate example operations for forming another alternative barrier including crosslinked amphiphilic molecules. Suspended barrier 801 illustrated in FIG. 8A includes ABA triblock copolymer molecules 821 in which reactive moiety 311 is located at the A-B interface between hydrophilic block 842 and hydrophobic block 841. Barrier 801 may be suspended using membrane support 200 and optional annulus 210 in a manner similar to that described with reference to FIGS. 2A-2B. Similarly as described with reference to FIGS. 5A-5B, each individual ABA molecule may be in one of two arrangements. For example, ABA molecules 821 may extend through the layer in a linear fashion, with an "A" section on each side of the membrane and the "B" section in the middle of the membrane. Or, for example, ABA molecules 822 may extend to the middle of the membrane and then fold back on themselves, so that both "A" sections are on the same side of the membrane and the "B" section is in the middle of the membrane. Accordingly, in this example, barrier 801 may be considered to be partially a single layer and partially a bilayer. In other examples (not specifically illustrated) in which barrier 501 substantially includes molecules 821 which extend through the barrier in linear fashion, barrier 501 may substantially be a monolayer. In still other examples (not specifically illustrated) in which barrier 801 substantially includes molecules 822 which extend to approximately the middle of the barrier and then fold back on themselves, barrier 801 may substantially be a bilayer. In a manner such as described with reference to FIGS. 3B-3C, reactive moieties 311 may be reacted so as to cross-link amphiphilic molecules 821 via bonds 281 as illustrated in FIG. 8B.

Figure 9A:
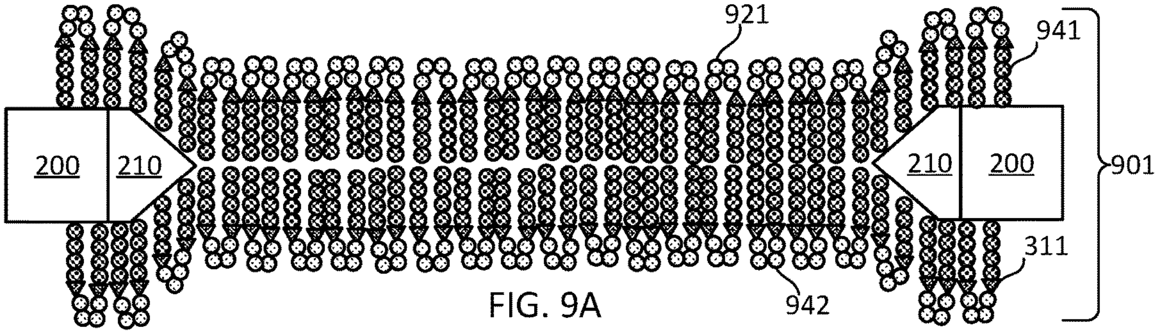
FIGS. 9A-9B schematically illustrate example operations for forming another alternative barrier including crosslinked amphiphilic molecules.
Figure 9B:
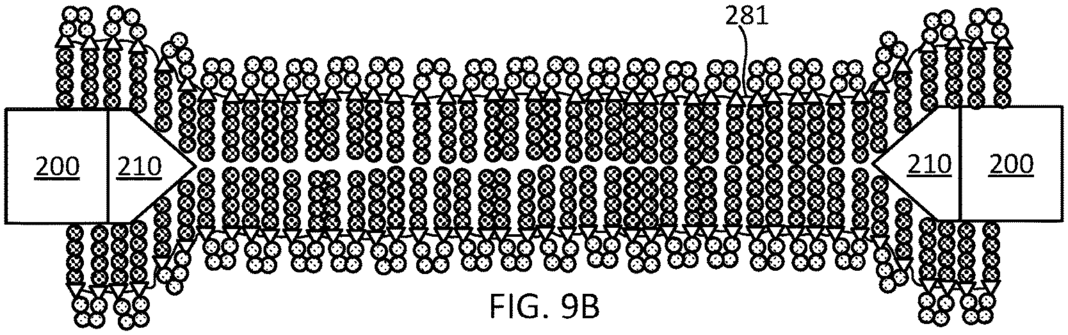

Or, for example, FIGS. 9A-8B schematically illustrate example operations for forming another alternative barrier including crosslinked amphiphilic molecules. Suspended barrier 901 illustrated in FIG. 9A includes BAB triblock copolymer molecules 921 in which reactive moiety 311 is located at the A-B interface between hydrophilic block 942 and hydrophobic block 941. Barrier 901 may be suspended using membrane support 200 and optional annulus 210 in a manner similar to that described with reference to FIGS. 2A-2B. In a manner such as described with reference to FIGS. 3B-3C, reactive moieties 311 may be reacted so as to cross-link amphiphilic molecules 921 via bonds 281 as illustrated in FIG. 9B.

Figure 10A:
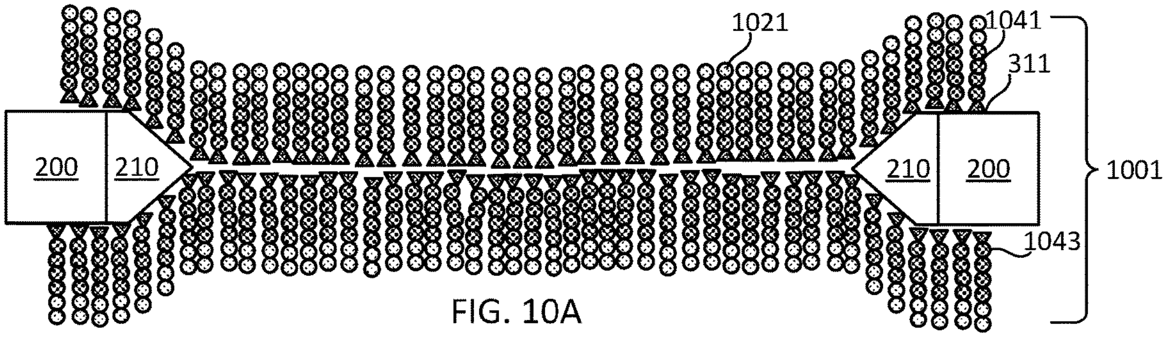
FIGS. 10A-10B schematically illustrate example operations for forming another alternative barrier including cross-linked amphiphilic molecules.
Figure 10B:
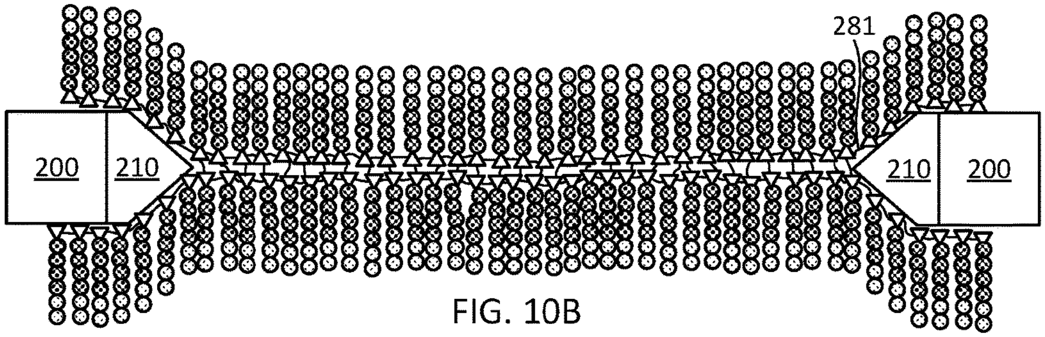
Figure 11A:
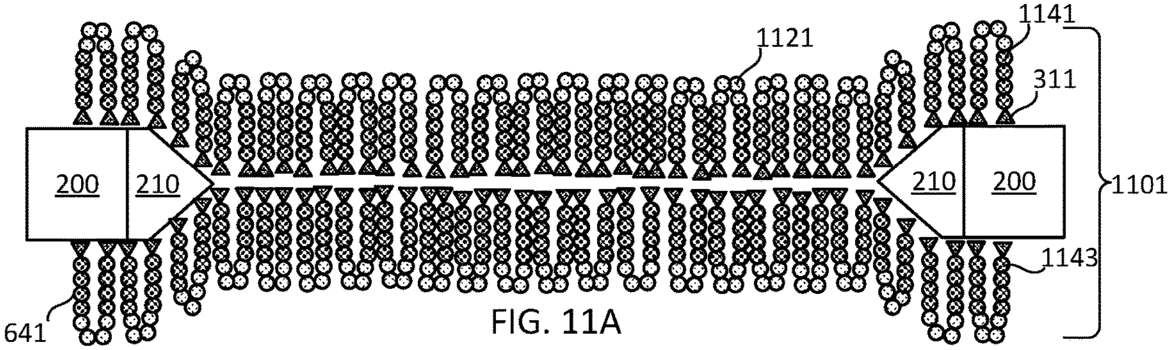
FIGS. 11A-11B schematically illustrate example operations for forming another alternative barrier including cross-linked amphiphilic molecules.
Figure 11B:
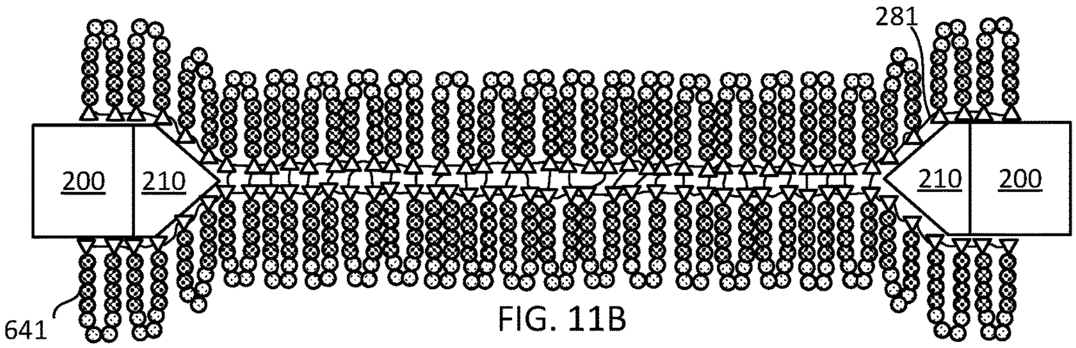

In other examples, the reactive moiety may be located at the end of the hydrophobic B block. Illustratively, FIGS. 10A-10B schematically illustrate example operations for forming another alternative barrier including crosslinked amphiphilic molecules. Suspended barrier 1001 illustrated in FIG. 10A includes AB diblock copolymer molecules 1021 in which reactive moiety 311 is located at hydrophobic block 1041, e.g., is coupled to the terminal monomer 1043 of the hydrophobic block. Barrier 1001 may be suspended using membrane support 200 and optional annulus 210 in a manner similar to that described with reference to FIGS. 2A-2B. In a manner such as described with reference to FIGS. 3B-3C, reactive moieties 311 may be reacted so as to cross-link amphiphilic molecules 1021 via bonds 281 as illustrated in FIG. 10B. Or, for example, FIGS. 11A-11B schematically illustrate example operations for forming another alternative barrier including crosslinked amphiphilic molecules. Suspended barrier 1101 illustrated in FIG. 11A includes BAB triblock copolymer molecules 1121 in which reactive moiety 311 is located at hydrophobic block 1141, e.g., is coupled to the terminal monomer 1143 of the hydrophobic block. In a manner such as described with reference to FIGS. 3B-3C, reactive moieties 311 may be reacted so as to cross-link amphiphilic molecules 1121 via bonds 281 as illustrated in FIG. 11B.

Note that depending on the particular arrangement and proximity of reactive moieties 311 to one another, in various examples provided herein bonds 281 may be located within a particular plane or planes within the barrier. For example, where bonds 281 cross-link the hydrophilic portions of amphiphilic molecules, e.g., such as described with reference to FIGS. 3A-3D, 5A-5B, and 6A-6B, and as will be described further below with reference to FIGS. 12A-12C, one set of the bonds 281 substantially may be located in a first plane providing a first outer surface of the barrier, and another set of the bonds 281 substantially may be located in a second plane providing a second outer surface of the barrier. For example, when the membrane is partially or substantially a bilayer, the bonds 281 of one of the membrane layers substantially may be located in a first plane providing a first outer surface of the membrane, the bonds 281 of the other one of the membrane layers substantially may be located in a second plane providing a second outer surface of the membrane; alternatively, when the membrane is substantially a monolayer, one set of the bonds 281 of that membrane substantially may be located in a first plane providing a first outer surface of the membrane, and another set of the bonds 281 substantially may be located in a second plane providing a second outer surface of the membrane.

Figure 13:
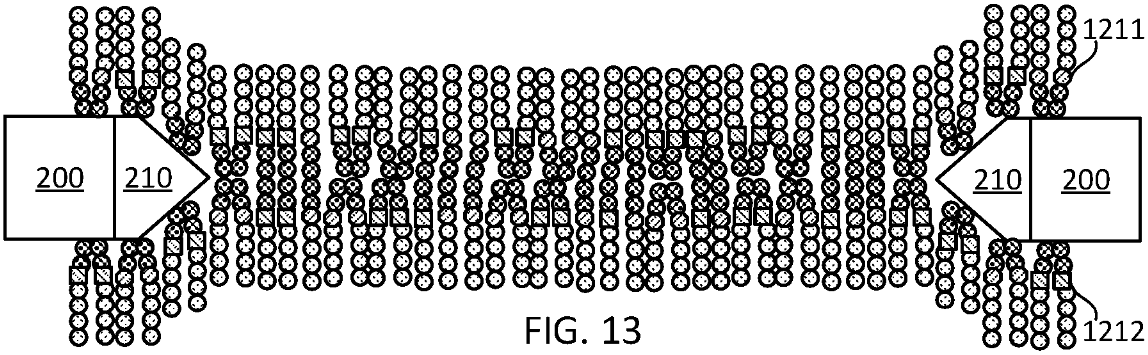
FIG. 13 illustrates an example operation for forming another alternative barrier including crosslinked amphiphilic molecules.

Or, for example, where bonds 281 cross-link the hydrophilic-hydrophobic interfaces of amphiphilic molecules, e.g., such as described with reference to 7A-7B, 8A-8B, and 9A-9B, and as will be described further below with reference to FIG. 13, one set of the bonds 281 substantially may be located in a first plane within that layer, and another set of the bonds 281 substantially may be located in a second plane within that layer. For example, when the membrane is partially or substantially a bilayer, the bonds 281 of one of the membrane layers substantially may be located in a first plane within a first layer of the membrane, the bonds 281 of the other one of the membrane layers substantially may be located in a second plane within a second layer within the membrane; alternatively, when the membrane is substantially a monolayer, one set of the bonds 281 of that membrane substantially may be located in a first plane within the membrane, and another set of the bonds 281 substantially may be located in a second plane within the membrane.

Figure 14A:
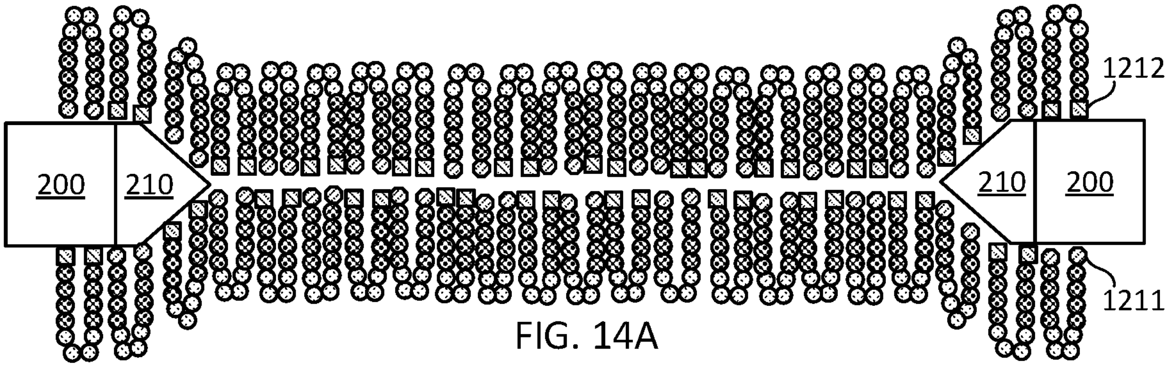
FIG. 14A illustrates an example operation for forming another alternative barrier including crosslinked amphiphilic molecules.
Figure 14B:
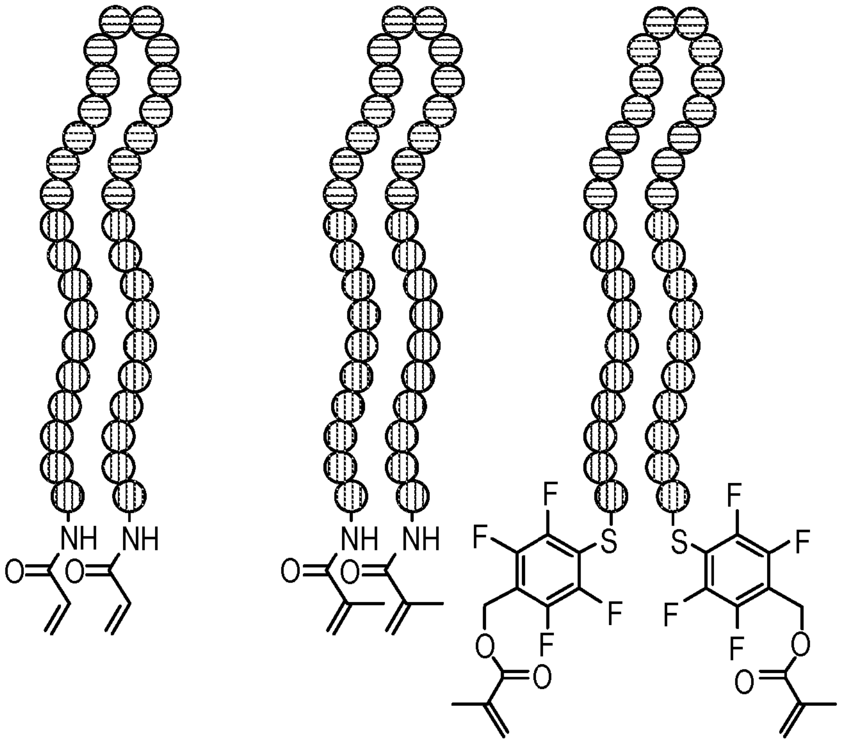
FIG. 14B schematically illustrates example triblock copolymer molecules that may be used in operations such as described with reference to FIGS. 11A-11B or FIG. 14A.

Or, for example, where bonds 281 cross-link hydrophobic portions of amphiphilic molecules, e.g., such as described with reference to FIGS. 10A-10B and 11A-11B, and as will be described further below with reference to FIGS. 14A-14B, the bonds 281 of each of the membrane layers may be located in one or more planes between the two layers. Illustratively, in a manner such as shown in FIGS. 10B and 11B, bonds 281 may be formed between reactive moieties 311 within the plane of the respective layer and/or may be formed between reactive moieties 311 in different planes than one another.

A variety of reactive moieties may be used in polymerization and cross-linking reactions such as described with reference to FIGS. 3A-11B. For example, reactive moieties 311 may be selected from the group consisting of an itaconic moiety, an N-carboxyanhydride moiety, a disulfyl pyridyl moiety, an acrylate moiety, a methacrylate moiety, an acrylamide moiety, a methacrylamide moiety, a styrenic moiety, a maleic moiety, a carboxylic acid moiety, a thiol moiety, an allyl moiety, a vinyl moiety, a propargyl moiety, and a maleimide moiety. In some examples, the polymerization reaction includes a ring-opening polymerization or a step-growth polymerization.

For AB and BAB architectures, there are ways of having a reactive moiety at the end of the B block and those could be crosslinked/polymerized (so the cross-linkages may extend laterally within the membrane). Examples of polymerizable moieties include but are not limited to acrylates or acrylamide derivatives; examples of crosslinkable moieties include but are not limited to thiols and alkenes/alkynes (to generate sulfides), thiols and maleimides (to generate thiosuccinimides), azides and alkynes/BCN/DBCO, thiols and thiols (to generate disulfides), dimethylmaleimide moieties, and the like.

For ABA architecture, there is not per se a ‘free end’ to the B block, however, some B blocks may be flanked with a central reactive moiety. Illustratively, such B blocks can be synthesized as follows: a homo-difunctional initiator containing a third central reactive moiety (such as those described above); the latter may not take part in the polymerization reaction (this can be done either through ensuring orthogonality or by being protected). Such polymerization may generate a telechelic B block that may be terminated in a fashion as to generate reactive ends that can react with the A blocks to generate ABA architecture, while preserving the aforementioned central reactive moiety for later use in the membrane for crosslinking/polymerization purposes. Alternative ways of generating such B blocks include, but not limited to: using heterodifunctional initiators (one functionality intended for the A block coupling, the other one is the initiating moiety) to polymerize B blocks, where the termination step uses a homo-difunctional initiator containing a third central reactive moiety (such as those described above) and 2 reactive moieties that can react with 2 growing B blocks.

For AB, BAB and ABA architectures, reactive moieties may be provided at the AB interface and those could be crosslinked/polymerized (so the cross-linkages may extend laterally within the membrane). Examples of polymerizable moieties include but are not limited itaconic of maleic acid derivatives; examples of crosslinkable moieties include but are not limited to thiols and alkenes/alkynes (to generate sulfides), thiols and thiols (to generate disulfides), dimethylmaleimide moieties, and the like.

For AB and ABA architectures, a reactive moiety may be provided at the end of the A block and those may be crosslinked/polymerized (so the cross-linkages may extend through the outer part of the membrane laterally). Examples of polymerizable moieties include but are not limited to acrylates or acrylamide derivatives; examples of crosslinkable moieties include but are not limited to thiols and alkenes/alkynes (to generate sulfides), thiols and thiols (to generate disulfides), azides and alkynes/BCN/DBCO, dimethylmaleimide moieties, etc.

For BAB architecture, there is not per se a ‘free end’ to the A block, however, A blocks may be flanked with a central reactive moiety. Illustratively, such A blocks may be synthesized as follows: a homo-difunctional initiator including a third central reactive moiety (such as those described above); the latter may not take part in the polymerization reaction (this can be done either through ensuring orthogonality or by being protected). Such polymerization would generate a telechelic A block that may be terminated in a fashion as to generate reactive ends that can react with the B blocks to generate BAB architecture, while preserving the aforementioned central reactive moiety for later use in the membrane for crosslinking/polymerization purposes. There are alternative ways of generating such A blocks, including but not limited to: using heterodifunctional initiators (one functionality intended for the B block coupling, the other one is the initiating moiety) to polymerize A blocks, where the termination step uses a homo-difunctional initiator containing a third central reactive moiety (such as those described above) and 2 reactive moieties that can react with 2 growing A blocks.

FIGS. 28-31 depict example chemical reactions between different reactive moieties in different locations of the block copolymer, such as described above. For simplicity, only AB block-copolymers are depicted, but—where relevant—such reactions also apply for ABA or BAB block-copolymers.

Figure 28:
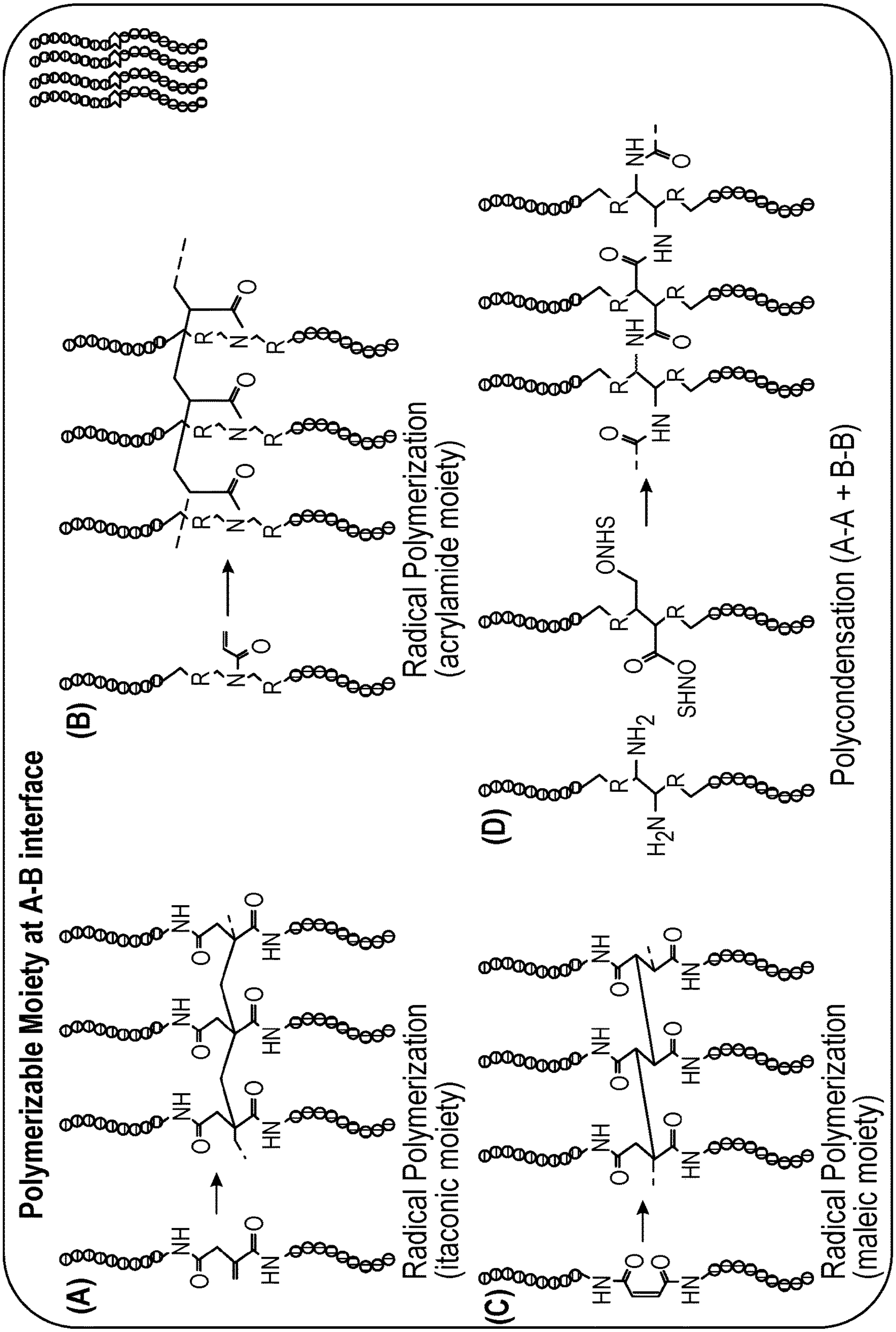
FIGS. 28-31 depict example chemical reactions between different reactive moieties in different locations of the block copolymer.

More specifically, FIG. 28 illustrates examples in which the A block and B block of a block copolymer are coupled together in a manner that produces/generates/leaves reactive moiet(ies) at the A-B interface, and the moiet(ies) then are reacted to cross-link block copolymer molecules to one another in a manner such as described with reference to FIGS. 7A-7B, 8A-8B, 9A-9B, 12A-12B, and/or 13. In example (A) shown in FIG. 28, the A and B blocks of a block copolymer molecule are coupled together using an itaconic moiety, and the itaconic moieties are polymerized using a radical polymerization process to strengthen at least one layer of the membrane, e.g., in a manner such as described with reference to FIG. 7A-7B, 8A-8B, or 9A-9B; optionally, a similar process may be used to strengthen a second layer of the membrane, if present. In example (B) shown in FIG. 28, the A and B blocks of a block copolymer molecule are coupled together using an acrylamide moiety, and the acrylamide moieties are polymerized using a radical polymerization process to strengthen at least one layer of the membrane, e.g., in a manner such as described with reference to FIG. 7A-7B, 8A-8B, or 9A-9B; optionally, a similar process may be used to strengthen a second layer of the membrane, if present. In example (C) shown in FIG. 28, the A and B blocks of a block copolymer molecule are coupled together using a maleic moiety, and the maleic moieties are polymerized using a radical polymerization process to strengthen at least one layer of the membrane, e.g., in a manner such as described with reference to FIG. 7A-7B, 8A-81B, or 9A-9B; optionally, a similar process may be used to strengthen a second layer of the membrane, if present.

In example (D) shown in FIG. 28, the A and B blocks of a first block copolymer molecule are coupled together using a first moiety, which in the illustrated example includes one or more primary amines ($—NH_2$), here first and second primary amines; and the A and B blocks of a second block copolymer molecule are coupled together using a second moiety, which in the illustrated example includes one or more NHS esters (—ONHS), here first and second NHS esters. The first moieties (e.g., amine moieties) are reacted with the second moieties (e.g., NHS esters) using a polycondensation process to strengthen at least one layer of the membrane, e.g., using first and second reactive moieties in a manner such as described with reference to FIG. 12A-12B or 13, to obtain a structure similar to that described with reference to FIG. 7A-7B, 8A-8B, or 9A-9B; optionally, a similar process may be used to strengthen a second layer of the membrane, if present. In examples in which each molecule includes two or more amines or two or more NHS esters, two or more of such molecules may be cross-linked with one another. For example, when each molecule includes three or more amines or three or more NHS esters, three or more of such molecules may be cross-linked with one another. The R groups illustrated in examples (A) and (D) of FIG. 28 may include any suitable moiety, such as aliphatic or aromatic or other non-reactive spacer.

Figure 29:
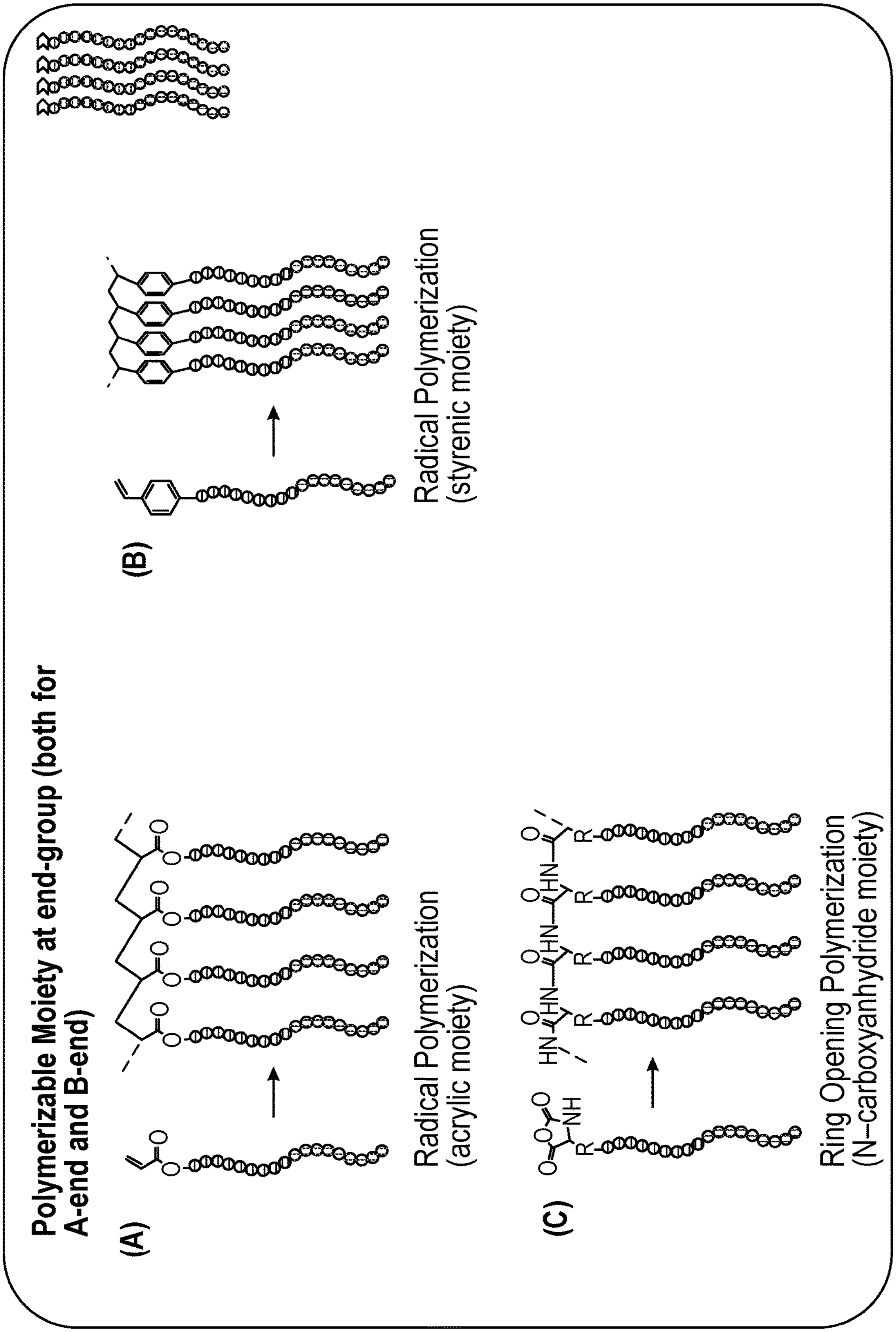

FIG. 29 illustrates examples in which a polymerizable moiety is at an end-group of an A block or at an end-group of a B block, and the moiety then is polymerized to cross-link the molecules of the block copolymer to one another in a manner such as described with reference to FIG. 3A-3D, 4, 5A-5B, 10A-10B, or 11A-11B. In example (A) shown in FIG. 29, an acrylic moiety is located at the end of an A block or at the end of a B block, and the acrylic moieties are polymerized using a radical polymerization process to strengthen at least one layer of the membrane, e.g., in a manner such as described with reference to FIG. 3A-3D, 4, 5A-5B, 10A-10B, or 11A-11B; optionally, a similar process may be used to strengthen a second layer of the membrane, if present. In example (B) shown in FIG. 29, a styrenic moiety is located at the end of an A block or at the end of a B block, and the styrenic moieties are polymerized using a radical polymerization process to strengthen at least one layer of the membrane, e.g., in a manner such as described with reference to FIG. 3A-3D, 4, 5A-5B, 10A-10B, or 11A-11B; optionally, a similar process may be used to strengthen a second layer of the membrane, if present. In example (C) shown in FIG. 29, an N-carboxyanhydride moiety is located at the end of an A block or at the end of a B block, and the N-carboxyanhydride moieties are polymerized using a ring-opening polymerization process to strengthen at least one layer of the membrane, e.g., in a manner such as described with reference to FIG. 3A-3D, 4, 5A-5B, 10A-10B, or 11A-11B; optionally, a similar process may be used to strengthen a second layer of the membrane, if present. The R groups illustrated in example (C) of FIG. 29 may include any suitable moiety, such as aliphatic or aromatic or other non-reactive spacer.

Figure 30:
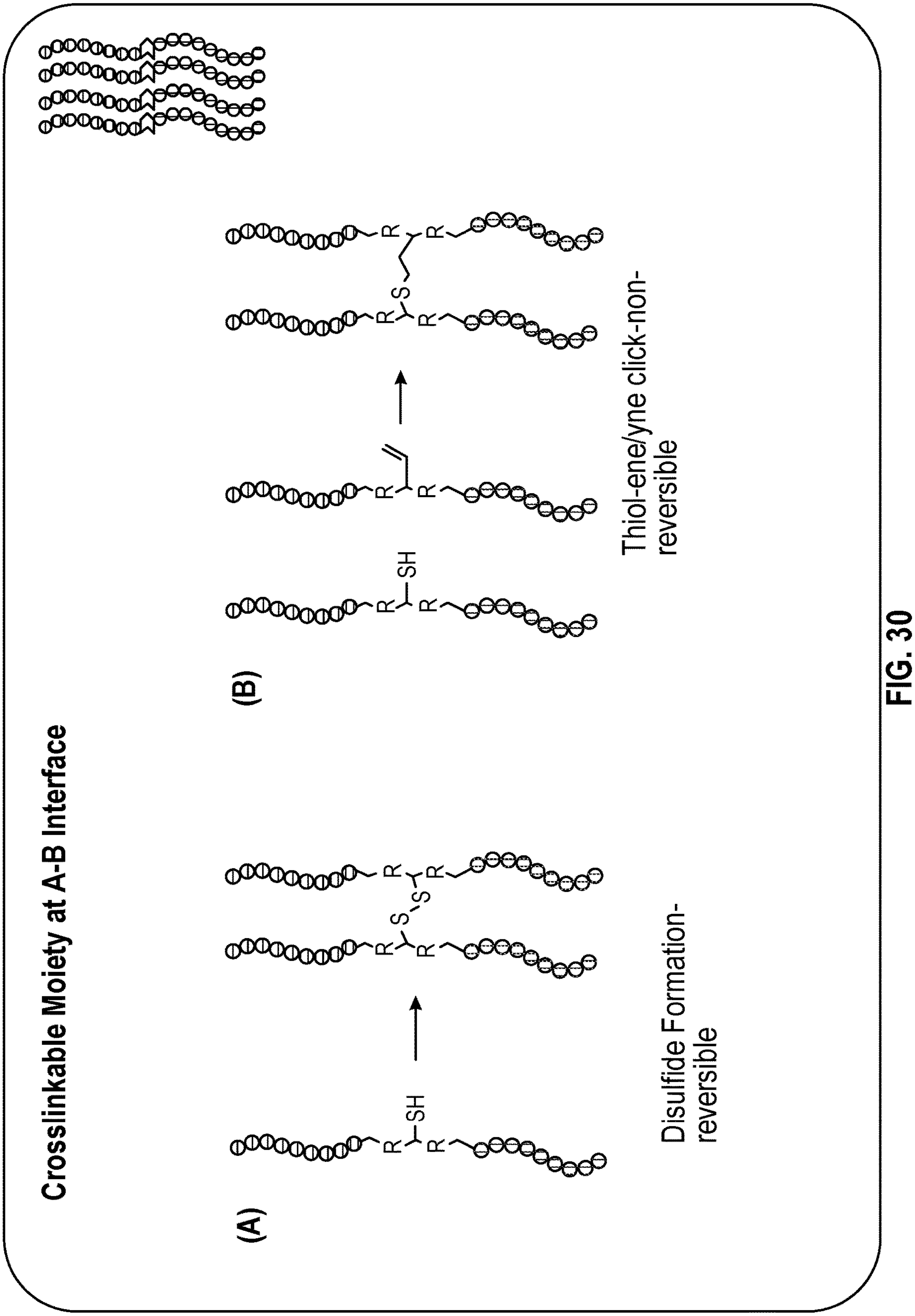

FIG. 30 illustrates additional examples in which the A block and B block of a block copolymer are coupled together using reactive moiet(ies) at the A-B interface, and the moiet(ies) then are reacted to cross-link the molecules of the block copolymer to one another in a manner such as described with reference to FIGS. 7A-7B, 8A-8B, 9A-9B, 12A-12B, and/or 13. In example (A) shown in FIG. 30, the A and B blocks of a block copolymer molecule are coupled together using a moiety including a thiol group (—SH), and the moieties are coupled together using a disulfide formation process to strengthen at least one layer of the membrane, e.g., in a manner such as described with reference to FIG. 7A-7B, 8A-8B, or 9A-9B; optionally, a similar process may be used to strengthen a second layer of the membrane, if present. In example (A) of FIG. 30, the cross-linking optionally is reversible.

In example (B) shown in FIG. 30, the A and B blocks of a first block copolymer molecule are coupled together using a first moiety, which in the illustrated example includes one or more thiol groups (—SH); and the A and B blocks of a second block copolymer molecule are coupled together using a second moiety, which in the illustrated example includes one or more alkynes or alkenes. The first moieties (e.g., thiol moieties) are reacted with the second moieties (e.g., alkynes or alkenes) for example, using a thiol-ene/yne click chemistry process (which is not reversible), to strengthen at least one layer of the membrane, e.g., using first and second reactive moieties in a manner such as described with reference to FIG. 12A-12B or 13, to obtain a structure similar to that described with reference to FIG. 7A-7B, 8A-8B, or 9A-9B; optionally, a similar process may be used to strengthen a second layer of the membrane, if present. In examples in which each molecule includes two or more thiols or two or more alkynes or alkenes, two or more of such molecules may be cross-linked with one another. For example, when each molecule includes three or more thiols or three or more alkenes, three or more of such molecules may be cross-linked with one another. The R groups illustrated in examples (A) and (B) of FIG. 30 may include any suitable moiety, such as aliphatic or aromatic or other non-reactive spacer.

Figure 31:
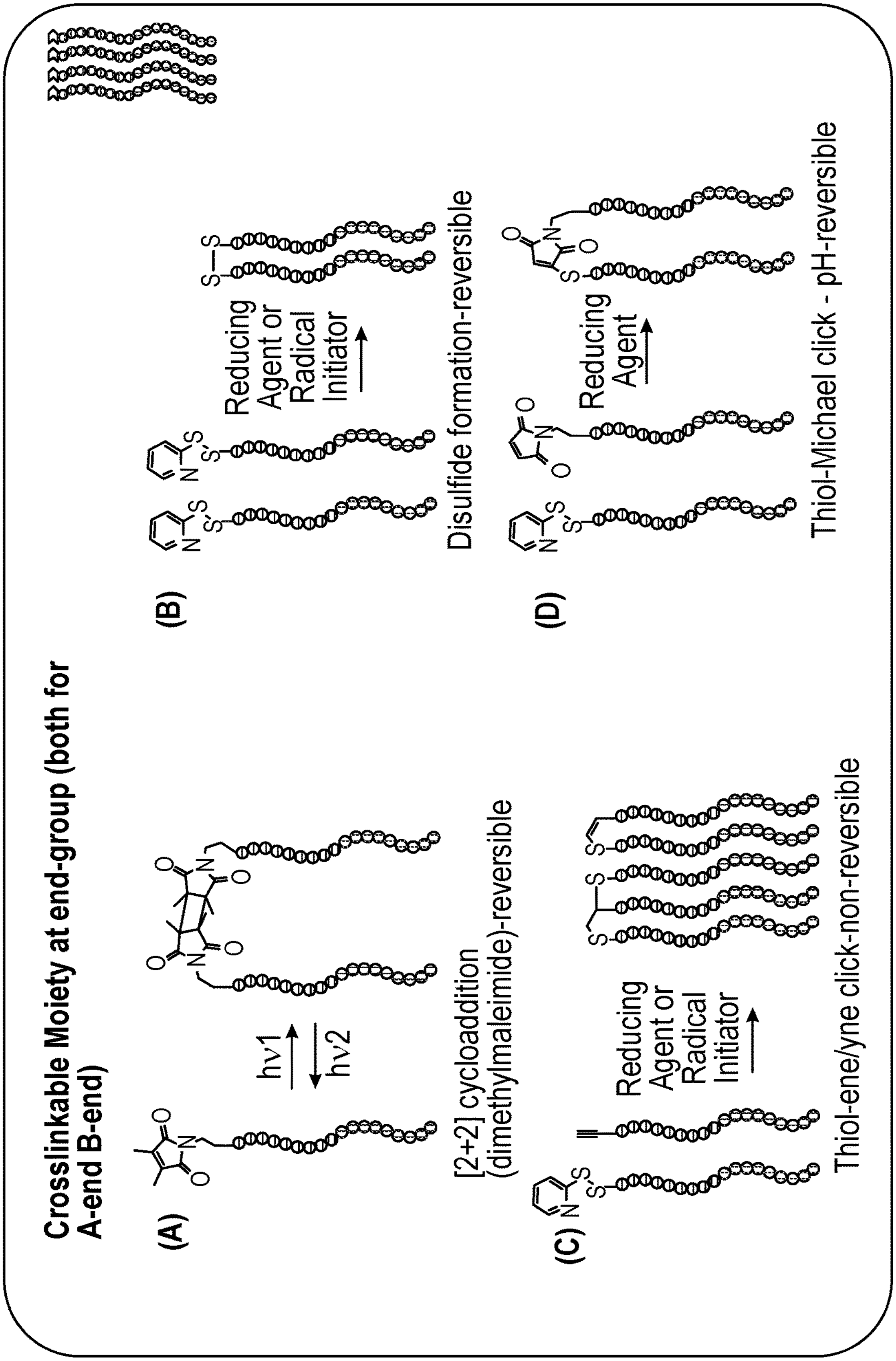

FIG. 31 illustrates additional examples in which reactive moiet(ies) are at an end-group of an A block or at an end-group of a B block, and the moiet(ies) then are reacted to cross-link the molecules of the block copolymer to one another in a manner such as described with reference to FIG. 3A-3D, 4, 5A-5B, 10A-10B, 11A-11B, 12A-12B, or 14A-14B. In example (A) shown in FIG. 31, dimethylmaleimide is located at the end of an A block or at the end of a B block, and the dimethylmaleimide moieties are reacted in a [2+2] cycloaddition process to strengthen at least one layer of the membrane, e.g., in a manner such as described with reference to FIG. 3A-3D, 4, 5A-5B, 10A-10B, or 11A-11B; optionally, a similar process may be used to strengthen a second layer of the membrane, if present. In example (A) of FIG. 31, the cross-linking optionally is reversible. In example (B) shown in FIG. 31, a disulfide pyridyl moiety is located at the end of an A block or at the end of a B block, and the disulfide pyridyl moieties are polymerized using a disulfide formation process (which may use a reducing agent or radical intiator) to strengthen at least one layer of the membrane, e.g., in a manner such as described with reference to FIG. 3A-3D, 4, 5A-5B, 10A-10B, or 11A-11B; optionally, a similar process may be used to strengthen a second layer of the membrane, if present. In example (B) of FIG. 31, the cross-linking optionally is reversible.

In example (C) shown in FIG. 31, a first block copolymer molecule includes a first moiety (e.g., disulfide pyridyl in the illustrated example) and a second block copolymer molecule includes a second moiety (e.g., alkene or alkyne in the illustrated example). The first moiety (e.g., disulfide pyridyl) is reacted with one or more of the second moieties (e.g., alkyne(s) or alkene(s)), for example using a thiol-ene/yne click chemistry process (which is not reversible), to strengthen at least one layer of the membrane, e.g., using first and second reactive moieties in a manner such as described with reference to FIG. 12A-12B or 14A-14B, to obtain a structure similar to that described with reference to FIG. 3A-3D, 4, 5A-5B, 10A-10B, 11A-11B, 12A-12B, or 14A-14B; optionally, a similar process may be used to strengthen a second layer of the membrane, if present. In the illustrated example, an alkyne may react with up to two thiols. The first reaction between the yne and thiol moieties consumes the triple bond and generates a double bond, which in turn can react with another thiol.

In example (D) shown in FIG. 31, a first block copolymer molecule includes a first moiety (e.g., disulfide pyridyl in the illustrated example) and a second block copolymer molecule includes a second moiety (e.g., maleimide in the illustrated example). The first moiety (e.g., disulfide pyridyl) is reacted with the second moiety (e.g., maleimide), for example using a thiol-Michael click chemistry process (which is pH reversible), to strengthen at least one layer of the membrane, e.g., using first and second reactive moieties in a manner such as described with reference to FIG. 12A-12B or 14A-14B, to obtain a structure similar to that described with reference to FIG. 3A-3D, 4, 5A-5B, 10A-10B, 11A-11B, 12A-12B, or 14A-14B; optionally, a similar process may be used to strengthen a second layer of the membrane, if present.

In a manner such as noted with reference to FIG. 3B, the polymerization reaction(s) optionally may be initiated using an initiator. Nonlimiting examples of suitable initiators include a photoinitiator, a redox system, or photons (such as ultraviolet (UV) light). Illustratively, the photoinitiator is UV activated and is selected from the group consisting of: 2,2-dimethoxy-2-phenylacetophenone, 2,2'-azobis(2-methylpropionamidine) dihydrochloride, 2-hydroxy-4'-(2-hydroxyethoxy)-2-methylpropiophenone, and lithium phenyl-2,4,6-trimethylbenzoylphosphinate, structures for which are shown below: 2,2-dimethoxy-2-phenylacetophenone (DMAP):

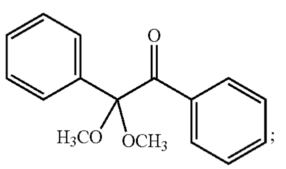 [SMILES: COC(OC)(C(=O)c1ccccc1)c1ccccc1]

2,2'-azobis(2-methylpropionamidine) dihydrochloride (V50):

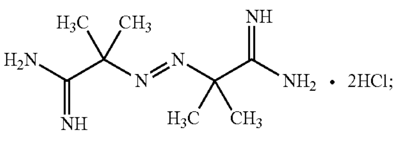

2-hydroxy-4'-(2-hydroxyethoxy)-2-methylpropiophenone (Irgacure 2959):

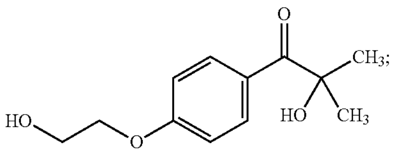 [SMILES: CC(C)(O)C(=O)c1ccc(OCCO)cc1]

and lithium phenyl-2,4,6-trimethylbenzoylphosphinate:

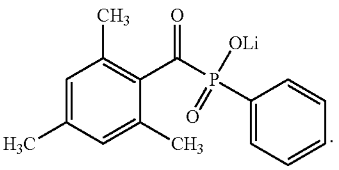

In examples described herein which UV light is used, the barrier may be located within a structure which is at least partially transparent to the UV light, so as to facilitate cross-linking and/or reversing cross-linking. For example, the barrier may be located within a flowcell the lid of which may be at least partially transparent to the UV light used for cross-linking and/or reversing cross-linking, such that a sufficient amount of the UV light reaches the barrier to sufficiently conduct the reaction.

In some examples, the redox system includes potassium persulfate and N,N,N',N'-tetramethylethylenediamine, the structures of which are shown below:

potassium persulfate (KPS):

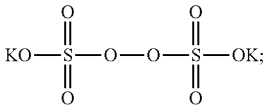

and

N,N,N',N'-tetramethylethylenediamine (TEMED):

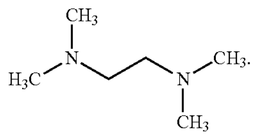

Ammonium persulfate and TEMED alternatively may be used as the redox system.

Figure 12A:
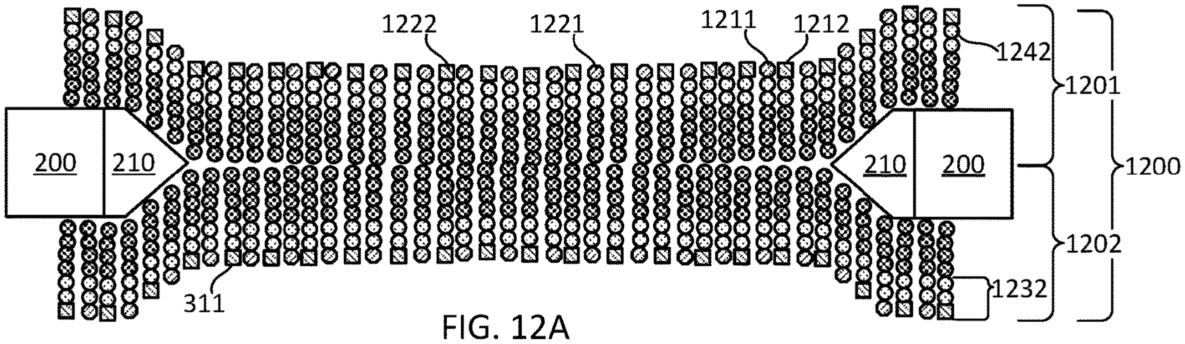
FIGS. 12A-12B schematically illustrate example operations for forming another alternative barrier including cross-linked amphiphilic molecules.
Figure 12B:
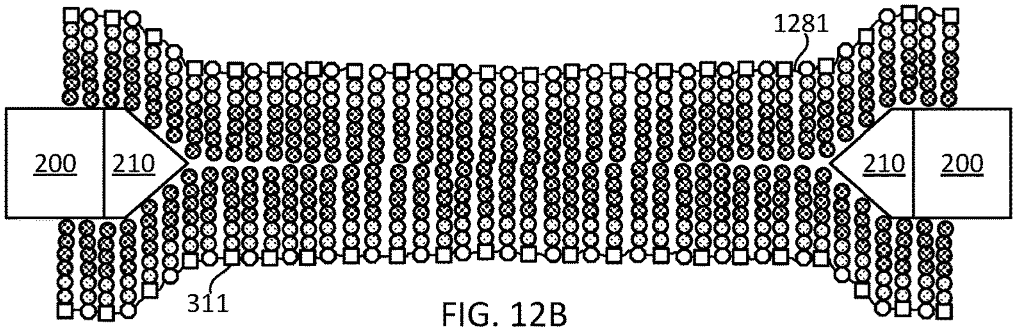

While FIGS. 3A-11B may illustrate cross-linking of amphiphilic molecules using polymerization, it will be appreciated that other types of crosslinking reactions, such as coupling reactions, suitably may be used to crosslink the amphiphilic molecules. For example, FIGS. 12A-12B schematically illustrate example operations for forming another alternative barrier including crosslinked amphiphilic molecules. FIG. 12A illustrates suspended barrier 1200. As illustrated in FIG. 12A, barrier 1200 may be configured, in some regards, similarly as membrane 101 described with reference to FIGS. 1 and 2A-2B, e.g., may include layer 1201 including a first plurality of amphiphilic molecules and layer 1202 including a second plurality of amphiphilic molecules. Some of the amphiphilic molecules of layer 1201 (and optionally also of layer 1202) may include reactive moieties 1211 (here, molecules 1221, which are located in both layer 1201 and layer 1202), while other of the amphiphilic molecules of layer 1201 (and optionally also of layer 1202) may include reactive moieties 1212 which are different than reactive moieties 1211 (here, molecules 1221, which are located in both layer 1201 and layer 1202). In examples such as illustrated in FIG. 12A, the amphiphilic molecules 1221, 1222 include molecules of an AB diblock copolymer, of which the hydrophilic "A" sections 1232 of molecules 1221 may include reactive moiety 1211 while the A sections 1232 of molecules 1222 may include reactive moiety 1212, e.g., coupled to the terminal hydrophilic monomer 1242. In other examples, just one type of reactive moiety is used. Suitable methods of forming suspended membranes using barrier supports are known in the art, such as "painting", e.g., brush painting (manual), mechanical painting (e.g., using stirring bar), and bubble painting (e.g., using flow through the device).

Reactive moieties 1211, 1212 may be reacted with one another in such a manner as to fully or partially cross-link the amphiphilic molecules with one another. For example, in a manner similar to that described with reference to FIG. 3B, barrier 1200 may be contacted with a fluid in which an initiator 1221 is dissolved which is chemically reactive with reactive moieties 1211 and/or 1212 e.g., so as to form products in which the amphiphilic molecules 221 are cross-linked to one another, such as via coupling of moieties 1211 to moieties 1212.

FIG. 12B illustrates the products of polymerization reactions between the amphiphilic molecules, in which bonds 1281 are formed between reactive moieties 1211 and 1212 (the fill of which is changed from crosshatched to white to indicate that such moieties have reacted and are no longer available for reaction). Although FIG. 12B may suggest that each reactive moiety 1211 is cross-linked to two of moieties 1212 via respective bonds 1281 and that each reactive moiety 1212 is cross-linked to two of moieties 1211 via respective bonds 1281, it will be appreciated that each reactive moiety may form bonds with any suitable number of other such reactive moieties, e.g., one, two, three, or more than three other such reactive moieties, and that bonds 1281 can be of different types than one another, e.g., may include different moieties than one another. The relative proportion of such products may be controlled in a manner such as described elsewhere herein, e.g., through the type of reactive moieties used, the type of initiator used, and the reaction conditions, so as to control the amount of cross-linking provided using reactions between the reactive moieties 1211 and 1212. Additionally, in some examples, the amount of cross-linking may be controlled by mixing the amphiphilic molecules respectively including reactive moieties 1211, 1212 in suitable proportion with other amphiphilic molecules that do not include reactive moieties 1211 and 1212, or that include different reactive moieties, and/or that have a different architecture (e.g., AB can be mixed with ABA and/or BAB; ABA can be mixed with AB and/or BAB; and/or BAB can be mixed with AB and/or ABA). For example, the ratio between the different types of amphiphilic molecules may be selected so as to determine the extent of cross-linking. Illustratively, in the case where two different amphiphilic molecules are used, the ratio may be selected (e.g., a ratio of about 1:2 of monofunctional to bifunctional molecules) so as to provide substantially full cross-linking between the molecules whereas a lower ratio (e.g., a ratio of about 1:1) may leave some molecules unreacted and thus only partially cross-linked.

In some examples, following cross-linking of amphiphilic molecules 1221, 1222, or before cross-linking of amphiphilic molecules 1221, 1222, nanopore 110 may be inserted into the barrier in a manner, e.g., in a manner such as described with reference to FIG. 3D or FIG. 4.

In a similar manner as described with reference to FIGS. 5A-5B, 6A-6B, 7A-7B, 8A-8B, 9A-9B, 10A-10B, and 11A-11B, the type(s) of amphiphilic molecules used, and the locations of the reactive moieties 1211, 1212 within such molecules, suitably may be varied. For example, moieties 1211 and 1212 instead may be located at the A-B interface of the molecules of FIGS. 12A-12C, or instead may be located at the B block of the molecules of FIGS. 12A-12C. Or, for example, moieties 1211 and 1212 instead may be provided within ABA triblock copolymers, e.g., at the A block, at the A-B interface, or at the B block. Or, for example, moieties 1211 and 1212 instead may be provided within BAB triblock copolymers, e.g., at the A block, at the A-B interface, or at the B block. FIG. 13 illustrates an example operation for forming another alternative barrier including crosslinked amphiphilic molecules, in which moieties 1211 and 1212 are provided at the A-B interface of ABA triblock copolymers. FIG. 14 illustrates an example operation for forming another alternative barrier including crosslinked amphiphilic molecules, in which moieties 1211 and 1212 are provided at the B block of BAB triblock copolymers. The barriers are illustrated in FIGS. 13 and 14A prior to crosslinking, and suitably may be crosslinked in a manner to form bonds 1281 such as provided herein, e.g., with reference to FIGS. 12A-12C.

A variety of reaction schemes may be used in coupling reactions such as described with reference to FIGS. 12A-14B. For example, the coupling reaction may include a thiol-ene click reaction, a thiol-yne click reaction, a strain-promoted alkyne-azide cycloaddition (e.g., an azide with DBCO or BCN), an amide coupling (primary amide with N-hydroxysuccinimide (NHS) or pentafluorophenyl (PFP)-activated esters), a thiol/aza-Michael reaction (thiol/primary amine with maleimide, maleic, fumaric, acrylic, or acrylamide), a [2+2] photocycloaddition (e.g., dimethylmaleimide, enones, or coumarin), a protein-ligand interaction (e.g., biotin-avidin or biotin-streptavidin), condensation (e.g., amine with an NHS ester), or host-guest chemistry (e.g., cyclodextrin-adamantane). Such reactions may be irreversible. Alternatively, reversible reactions may be used such as a disulfide formation, an imine formation, [2+2] cycloaddition, thiol-Michael click reaction, or an enamine formation (e.g., aldehyde/ketone). Nonlimiting examples of reactive moieties 1211, 1212 may include a disulfide pyridyl moiety, a lipoamido moiety, a propargyl moiety, an azide moiety, a DBCO moiety, a BCN moiety, an amine moiety, an activated carboxylic moiety, a dimethylmaleimide moiety, a propargyl moiety, an NHS ester, or a maleimide moiety. Optionally, the coupling reaction may be initiated using an initiator, such as a free-radical initiator, a redox system, a reducing agent, or photons. Nonlimiting examples of free-radical initiators include 2-hydroxy-4'-(2-hydroxyethoxy)-2-methylpropiophenone and 2,2'-azobis(2-methylpropionamidine) dihydrochloride, structures of which are provided above. A nonlimiting example of a redox system is potassium persulfate or ammonium persulfate and N,N,N',N'-tetramethylethylenediamine, structures of which are provided above. Nonlimiting examples of reducing agents include tris(2-carboxyethyl) phosphine, dithiothreitol, sodium ascorbate, and a phosphine.

Figure 12C:
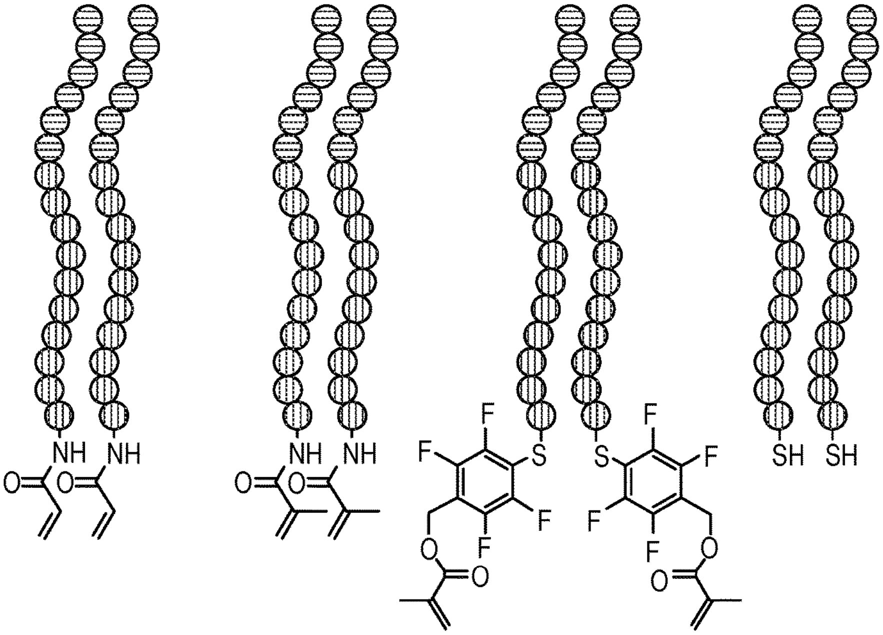
FIG. 12C schematically illustrates example diblock copolymer molecules that may be used in operations such as described with reference to FIGS. 3A-3D or FIGS. 12A-12B.

FIG. 12C schematically illustrates example diblock copolymer molecules that may be used in operations such as described with reference to FIG. 3A-3D or 12A-12B, and FIG. 14B schematically illustrates example triblock copolymer molecules that may be used in operations such as described with reference to FIG. 11A-11B or FIG. 14A. From left to right in FIGS. 12C and 14B, the groups include acrylamide (used for polymerization reaction), methacrylamide (used for polymerization reaction), penta-fluoro benzyl methacrylate (used for polymerization reaction), and thiol (used for coupling reaction). Other nonlimiting examples are described with reference to FIGS. 28-31. Still other nonlimiting examples are described elsewhere herein.

Figures 15A, 15B, 15C:
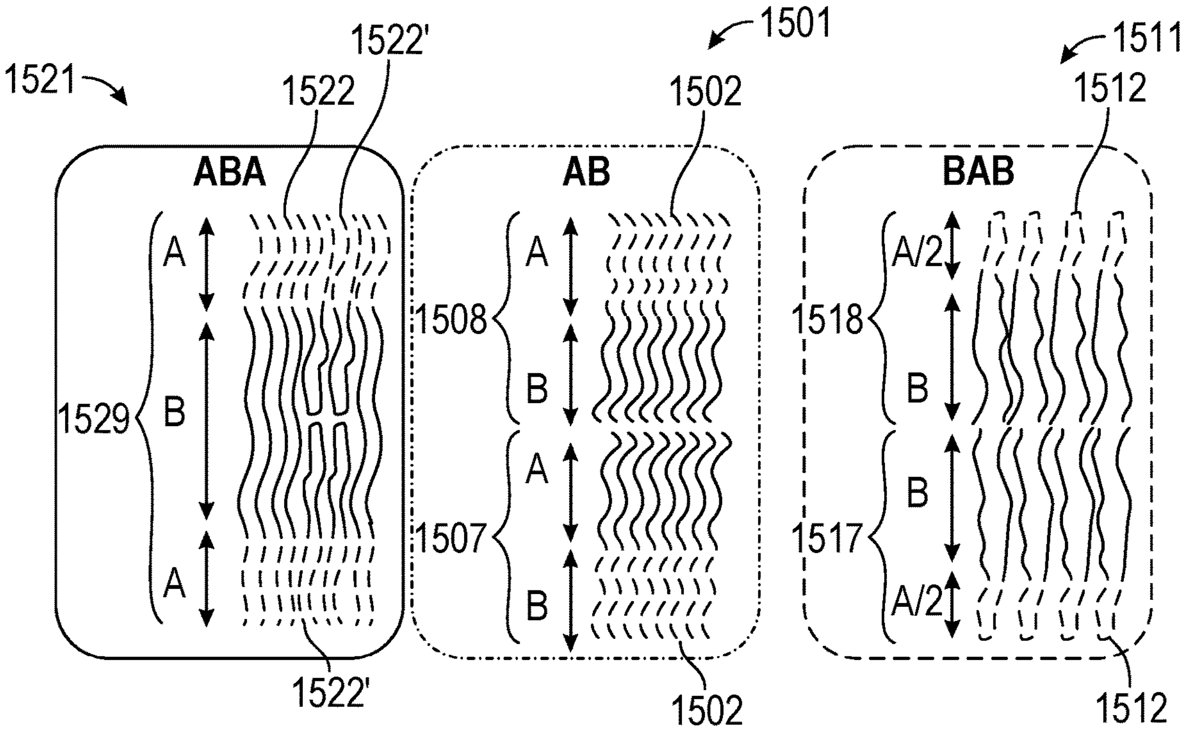
FIGS. 15A-15C schematically illustrate further details of membranes using block copolymers which may be included in the nanopore composition and device of FIG. 1 and used in respective operations described with reference to FIGS. 3A-14B.

FIGS. 15A-15C schematically illustrate further details of membranes using block copolymers which may be included in the nanopore composition and device of FIG. 1 and used in respective operations described with reference to FIGS. 3A-14B. It will be appreciated that such membranes suitably may be adapted for use in any other composition or device, and are not limited to use with nanopores. The hydrophilic blocks of the membranes described with reference to FIGS. 15A-15C may include reactive moieties 311, 1211, or 1212 such as described elsewhere herein.

Referring now to FIG. 15B, membrane 1501 uses a diblock "AB" copolymer. Membrane 1501 includes first layer 1507 which may contact fluid 120 and second layer 1508 which may contact fluid 120' in a manner similar to that described with reference to FIG. 1. First layer 1507 includes a first plurality of molecules 1502 of a diblock AB copolymer, and second layer 1508 includes a second plurality of the molecules 1502 of the diblock AB copolymer. As illustrated in FIG. 15B, each molecule 1502 of the diblock copolymer includes a hydrophobic block, denoted "B" and being approximately of length "B," coupled to a hydrophilic block, denoted "A" and being approximately of length "A". The hydrophilic A blocks of the first plurality of molecules 1502 (the molecules forming layer 1507) form a first outer surface of the membrane 1501, e.g., contact fluid 120. The hydrophilic A blocks of the second plurality of molecules 1502 (the molecules forming layer 1508) form a second outer surface of the membrane 1502, e.g., contact fluid 120'. The respective ends of the hydrophobic B blocks of the first and second pluralities of molecules contact one another within the membrane 1501 in a manner such as illustrated in FIG. 15B. As illustrated, substantially all of the molecules 1502 within layer 1507 may extend substantially linearly and in the same orientation as one another, and similarly substantially all of the molecules 1502 within layer 1508 may extend substantially linearly and in the same orientation as one another (which is opposite that of the orientation the molecules within layer 1507). Accordingly, first and second layers 1507, 1508 each may have a thickness of approximately A+B, and membrane 1501 may have a thickness of approximately 2A+2B. In some examples, length A is about 2 repeating units (RU) to about 100 RU, or about 1 repeating unit (RU) to about 50 RU, e.g., about 5 RU to about 40 RU, or about 10 RU to about 30 RU, or about 10 RU to about 20 RU, or about 20 RU to about 40 RU. Additionally, or alternatively, in some examples, length B is about 2 RU to about 100 RU, or about 5 RU to about 100 RU, e.g., about 10 RU to about 80 RU, or about 20 RU to about 50 RU, or about 50 RU to about 80 RU. Optionally, barrier 1501 described with reference to FIG. 15B may be suspended across an aperture in a manner such as described with reference to FIGS. 2A-2B.

Referring now to FIG. 15C, membrane 1511 uses a triblock "BAB" copolymer. Membrane 1511 includes first layer 1517 which may contact fluid 120 and second layer 1518 which may contact fluid 120' in a manner similar to that described with reference to FIG. 1. First layer 1517 includes a first plurality of molecules 1512 of a triblock copolymer, and second layer 1518 includes a second plurality of the molecules 1512 of the triblock copolymer. As illustrated in FIG. 15C, each molecule 1512 of the triblock copolymer includes first and second hydrophobic blocks, each denoted "B" and being approximately of length "B," and a hydrophilic block disposed between the first and second hydrophobic blocks, denoted "A" and being approximately of length "A". The hydrophilic A blocks of the first plurality of molecules 1512 (the molecules forming layer 1517) form a first outer surface of the membrane 1511, e.g., contact fluid 120. The hydrophilic A blocks of the second plurality of molecules 1512 (the molecules forming layer 1518) form a second outer surface of the membrane 1511, e.g., contact fluid 120'. The respective ends of the hydrophobic B blocks of the first and second pluralities of molecules contact one another within the membrane 1511 in a manner such as illustrated in FIG. 15C. As illustrated, substantially all of the molecules 1512 within layer 1517 may extend in the same orientation as one another, and may be folded at the A block so that the A block can contact the fluid while the B blocks are interior to the membrane 1511. Similarly, substantially all of the molecules 1512 within layer 1518 may extend in the same orientation as one another (which is opposite that of the orientation the molecules within layer 1517), and may be folded at their A blocks so that the A blocks contact the fluid while the B blocks are interior to the membrane 1511. Accordingly, first and second layers 1517, 1518 each may have a thickness of approximately A/2+B, and membrane 1511 may have a thickness of approximately A+2B. In some examples, length A is about 2 RU to about 100 RU, e.g., about 10 RU to about 80 RU, or about 20 RU to about 50 RU, or about 50 RU to about 80 RU. Additionally, or alternatively, in some examples, length B is about 2 RU to about 100 RU, or about 5 RU to about 100 RU, e.g., about 10 RU to about 80 RU, or about 20 RU to about 50 RU, or about 50 RU to about 80 RU. Optionally, barrier 1511 described with reference to FIG. 15B may be suspended across an aperture in a manner such as described with reference to FIGS. 2A-2B.

Referring now to FIG. 15A, membrane 1521 uses a triblock "ABA" copolymer. Membrane 1521 includes layer 1529 which may contact both fluids 120 and 120'. Layer 1529 includes a plurality of molecules 1522 of a triblock ABA copolymer. As illustrated in FIG. 15A, each molecule 1522 of the triblock copolymer includes first and second hydrophilic blocks, each denoted "A" and being approximately of length "A," and a hydrophobic block disposed between the first and second hydrophilic blocks, denoted "B" and being approximately of length "B". The hydrophilic A blocks at first ends of molecules 1522 (the molecules forming layer 1529) form a first outer surface of the membrane 1521, e.g., contact fluid 120. The hydrophilic A blocks at second ends of molecules 1522 form a second outer surface of the membrane 1521, e.g., contact fluid 120'. The hydrophobic B blocks of the molecules 1522 are within the membrane 1511 in a manner such as illustrated in FIG. 15C. As illustrated, the majority of molecules 1522 within layer 1529 may extend substantially linearly and in the same orientation as one another. Optionally, as illustrated in FIG.

15A, some of the molecules 1522' may be folded at their B blocks, such that both of the hydrophilic A blocks of such molecules may contact the same fluid as one another. Accordingly, the example shown in FIG. 15A may be considered to be partially a single layer, and partially a bilayer. In other examples (not specifically illustrated), layer 1529 may be entirely a single-layer or may be entirely a bilayer, e.g., as also described elsewhere herein. Regardless of whether the membrane includes molecules 1522 which extend substantially linearly and/or molecules 1522' which are folded, as illustrated in FIG. 15A, layer 1529 may have a thickness of approximately 2A+B. In some examples, length A is about 1 RU to about 100 RU, e.g., about 2 RU to about 100 RU, or about 10 RU to about 80 RU, or about 20 RU to about 50 RU, or about 50 RU to about 80 RU. Additionally, or alternatively, in some examples, length B is about 2 RU to about 100 RU, or about 5 RU to about 100 RU, e.g., about 10 RU to about 80 RU, or about 20 RU to about 50 RU, or about 50 RU to about 80 RU. It will be appreciated that any end groups that are coupled to the hydrophilic or hydrophobic blocks contribute to the overall thickness of the barrier. Optionally, barrier 1521 described with reference to FIG. 15A may be suspended across an aperture in a manner such as described with reference to FIGS. 2A-2B.

It will be appreciated that the layers of the various membranes provided herein may be configured so as to have any suitable dimensions. Illustratively, to form membranes of similar dimension as one another:

A-B-A triblock copolymer (FIG. 15A) may have 2 hydrophilic blocks, each of length A (each A block is of $M_w$=x) and 1 hydrophobic block of length B ($M_w$=y); when self-assembled, those A-B-A triblock copolymers would form membranes with a top hydrophilic layer of length A, a core hydrophobic layer of length B, and a bottom hydrophilic layer of length A.

A-B diblock copolymer (FIG. 15B) may have 1 hydrophilic block of length A ($M_w$=x), and 1 hydrophobic block of length B ($M_w$=y/2); when self-assembled, those A-B diblock copolymers would form membranes with a top hydrophilic layer of length A, a core hydrophobic layer of length 2B, and a bottom hydrophilic layer of length A.

B-A-B triblock copolymer (FIG. 15C) may have 1 hydrophilic block of length A ($M_w$=x), and 2 hydrophobic blocks, each of length of B (each B block is of $M_w$=y/2); when self-assembled, those B-A-B triblock copolymers would form membranes with a top hydrophilic layer of length A/2, a core hydrophobic layer of length 2B, and a bottom hydrophilic layer of length A/2. Additionally, or alternatively, the polymer packing into the layer(s) of the membrane may affect the hydrophilic ratio for each of the membranes, where hydrophilic ratio may be defined as the ratio between molecular mass of the hydrophilic block and the total molecular weight (MW or $M_w$) of the block copolymer (BCP) (hydrophilic ratio=$M_w$ hydrophilic block/$M_w$ BCP). For example:

A-B-A triblock copolymer (FIG. 15A), hydrophilic ratio=2x/(2x+y);

A-B diblock copolymer (FIG. 15B), hydrophilic ratio=x/(x+y/2); and

B-A-B triblock copolymer (FIG. 15C), hydrophilic ratio=x/(x+y).

The present diblock and triblock copolymers may include any suitable combination of hydrophobic and hydrophilic blocks. In some examples, the hydrophilic A block may include a polymer selected from the group consisting of: N-vinyl pyrrolidone, polyacrylamide, zwitterionic polymer, hydrophilic polypeptide, nitrogen containing units, and poly (ethylene oxide) (PEO). Illustratively, the polyacrylamide may be selected from the group consisting of: poly(N-isopropyl acrylamide) (PNIPAM), and charged polyacrylamide, and phosphoric acid functionalized polyacrylamide. Nonlimiting examples of zwitterionic monomers that may be polymerized to form zwitterionic polymers include:

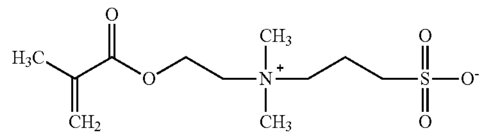
and
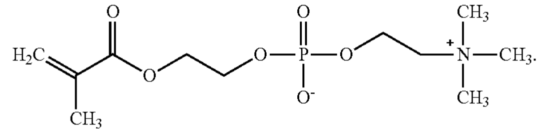

Nonlimiting examples of hydrophilic polypeptides include:

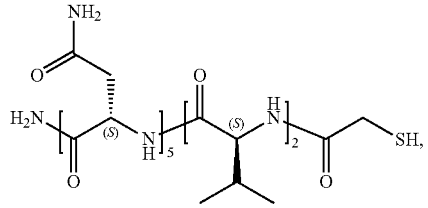
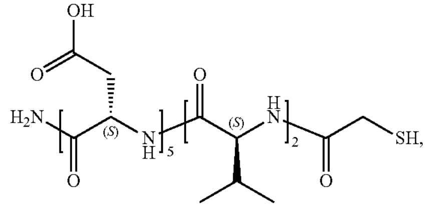
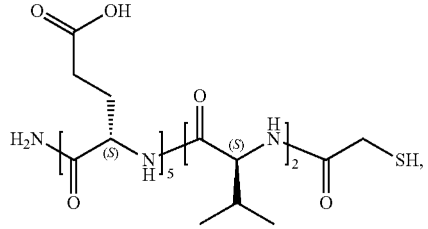
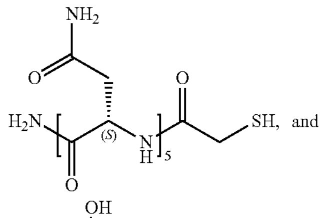
and
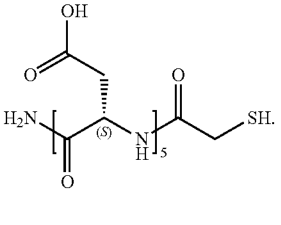

A nonlimiting example of a charged polyacrylamide is

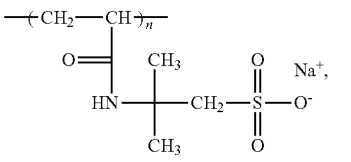

where n is between about 1 and about 100. Nonlimiting examples of nitrogen containing units include:

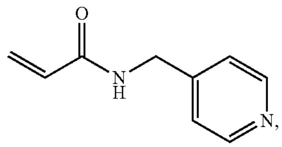

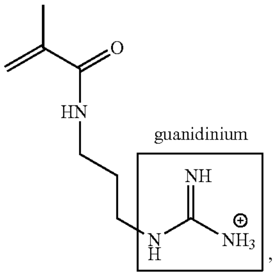

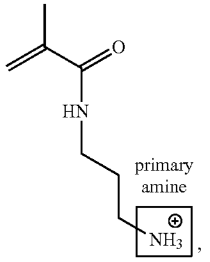

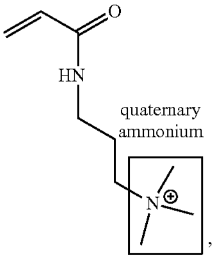

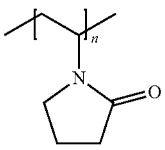

NVP,

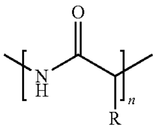

Peptides,

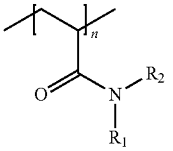

AM, and

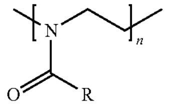

Oxa.

In some examples, the hydrophobic B block may include a polymer selected from the group consisting of: poly (dimethylsiloxane) (PDMS), polybutadiene (PBd), polyisoprene, polymyrcene, polychloroprene, hydrogenated polydiene, fluorinated polyethylene, polypeptide, and poly (isobutylene) (PIB). Nonlimiting examples of hydrogenated polydienes include saturated polybutadiene (PBu), saturated polyisoprene (PI), saturated poly(myrcene),

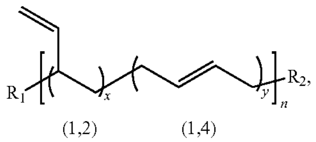

(1,2) (1,4)
cis/trans

-continued

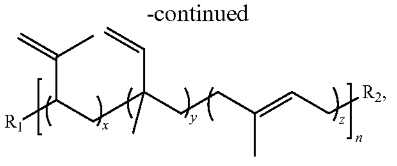

(3,4) (1,2) (1,4)
cis/trans

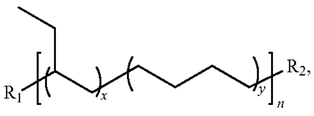

and (1,2) (1,4)

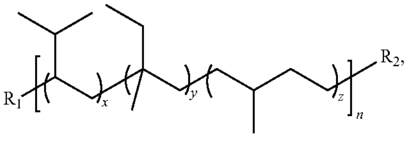

(3,4) (1,2) (1,4)

where n is between about 2 and about 100, x is between about 2 and about 100, y is between about 2 and about 100, z is between about 2 and about 100, $R_1$ is a functional group selected from the group consisting of a carboxylic acid, a carboxyl group, a methyl group, a hydroxyl group, a primary amine, a secondary amine, a tertiary amine, a biotin, a thiol, an azide, a propargyl group, an allyl group, an acrylate group, a zwitterionic group, a sulfate, a sulfonate, an alkyl group, an aryl group, an orthogonal functionality, and a hydrogen, and $R_2$ is a reactive moiety selected from the group consisting of a maleimide group, an allyl group, a propargyl group, a BCN group, a carboxylate group, an amine group, a thiol group, a DBCO group, an azide group, an N-hydroxysuccinimide group, a biotin group, a carboxyl group, an NHS-activated ester, and other activated esters. In other nonlimiting examples of hydrogenated polydienes, $R_1$ is a reactive moiety selected from the group consisting of a maleimide group, an allyl group, a propargyl group, a BCN group, a carboxylate group, an amine group, a thiol group, a DBCO group, an azide group, an N-hydroxysuccinimide group, a biotin group, a carboxyl group, an NHS-activated ester, and other activated esters. A nonlimiting example of fluorinated polyethylene is

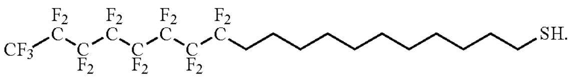 [SMILES: FC(F)(F)C(F)(F)C(F)(F)C(F)(F)C(F)(F)C(F)(F)C(F)(F)C(F)(F)CCCCCCCCCCCS]

Nonlimiting examples of hydrophobic polypeptides include (0<x<1):

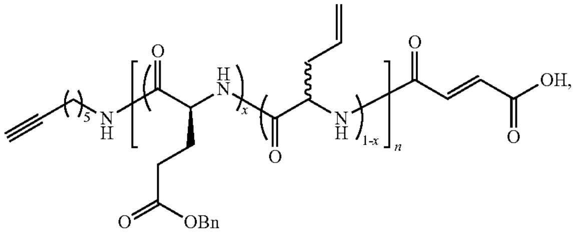

0 < x < 1

-continued

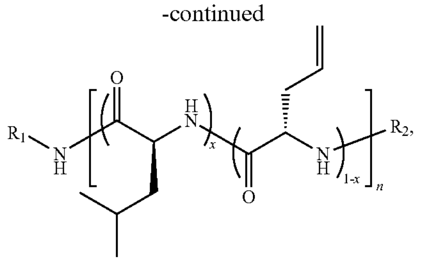

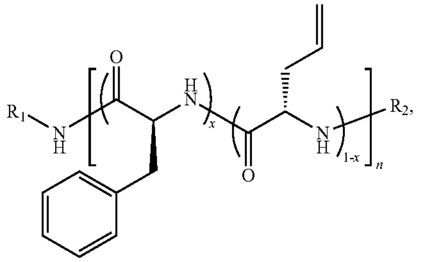

and

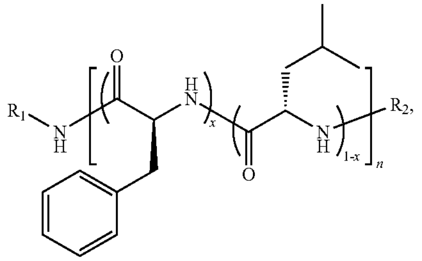

where n is between about 2 and about 100.

In one nonlimiting example, an AB diblock copolymer includes PDMS-b-PEO, where "-b-" denotes that the polymer is a block copolymer. In another nonlimiting example, an AB diblock copolymer includes PBd-b-PEO. In another nonlimiting example, an AB diblock copolymer includes PIB-b-PEO. In another nonlimiting example, a BAB triblock copolymer includes PDMS-b-PEO-b-PDMS. In another nonlimiting example, a BAB triblock copolymer includes PBd-b-PEO-b-PBd. In another nonlimiting example, a BAB triblock copolymer includes PIB-b-PEO-b-PIB. In another nonlimiting example, an ABA triblock copolymer includes PEO-b-PBd-b-PEO. In another nonlimiting example, and ABA triblock copolymer includes PEO-b-PDMS-b-PEO. In another nonlimiting example, an ABA triblock copolymer includes PEO-b-PIB-b-PEO. It will be appreciated that any suitable hydrophilic block(s) may be used with any suitable hydrophobic block(s). Additionally, in examples including two hydrophilic blocks, those blocks may be but need not necessarily include the same polymers as one another. Similarly, in examples including two hydrophobic blocks, those blocks may be but need not necessarily include the same polymers as one another.

The respective molecular weights, glass transition temperatures, and chemical structures of the hydrophobic and hydrophilic blocks suitably may be selected so as to provide the membrane with appropriate stability for use and ability to insert a nanopore. For example, the respective molecular weights of the hydrophobic and hydrophilic blocks may affect how thick each of the blocks (and thus layers of the membrane) are, and may influence stability as well as capacity to insert the nanopore, e.g., through electroporation, pipette pump cycle, or detergent assisted nanopore insertion. Additionally, or alternatively, the ratio of molecular weights of the hydrophilic and hydrophobic blocks may affect self-assembly of those blocks into the layers of the membrane. Additionally, or alternatively, the respective glass transition temperatures ($T_g$) of the hydrophobic and hydrophilic blocks may affect the lateral fluidity of the layers of the membrane; as such, in some examples it may be useful for the hydrophobic and/or hydrophilic blocks to have a $T_g$ of less than the operating temperature of the device, e.g., less than room temperature, and in some examples less than about 0° C. Additionally, or alternatively, chemical structures of the hydrophobic and hydrophilic blocks may affect the way the chains get packed into the layers, and stability of those layers.

For nanopore sequencing applications, membrane fluidity can be considered beneficial. Without wishing to be bound by any theory, the fluidity of a block copolymer membrane is believed to be largely imparted by the physical property of the hydrophobic "B" blocks. More specifically, B blocks including "low $T_g$" hydrophobic polymers (e.g., having a $T_g$ below around 0° C.) may be used to generate membranes that are more fluid than those with B blocks including "high $T_g$" polymers (e.g., having a $T_g$ above room temperature). For example, in certain examples, a hydrophobic B block of the copolymer has a $T_g$ of less than about 20° C., less than about 0° C., or less than about −20° C.

Hydrophobic B blocks with a low $T_g$ may be used to help maintain membrane flexibility under conditions suitable for performing nanopore sequencing, e.g., in a manner such as described with reference to FIGS. 32-36. In some examples, hydrophobic B blocks with a sufficiently low $T_g$ for use in nanopore sequencing may include, or may consist essentially of, PIB, which may be expected to have a $T_g$ in the range of about −75° C. to about −25° C. In other examples, hydrophobic B blocks with a sufficiently low $T_g$ for use in nanopore sequencing may include, or may consist essentially of, PDMS, which may be expected to have a $T_g$ in the range of about −135° C. (or lower) to about −115° C. In still other examples, hydrophobic B blocks with a sufficiently low $T_g$ for use in nanopore sequencing may include, or may consist essentially of, PBd. Different forms of PBd may be used as B blocks in the present barriers. For example, the cis-1,4 form of PBd may be expected to have a $T_g$ in the range of about −105° C. to about −85° C. Or, for example, the cis-1,2 form of PBd may be expected to have a $T_g$ in the range of about −25° C. to about 0° C. Or, for example, the trans-1,4 form of PBd may be expected to have a $T_g$ in the range of about −95° C. to about −5° C. In yet other examples, hydrophobic B blocks with a sufficiently low $T_g$ for use in nanopore sequencing may include, or may consist essentially of, polymyrcene (PMyr), which may be expected to have a $T_g$ in the range of about −75° C. to about −45° C. In yet other examples, hydrophobic B blocks with a sufficiently low $T_g$ for use in nanopore sequencing may include, or may consist essentially of, polyisoprene (PIP). Different forms of PIP may be used as B blocks in the present barriers. For example, the cis-1,4 form of PIP may be expected to have a $T_g$ in the range of about −85° C. to about −55° C. Or, for example, the trans-1,4 form of PIP may be expected to have a $T_g$ in the range of about −75° C. to about −45° C.

Hydrophobic B blocks with a fully saturated carbon backbone, such as PIB, also may be expected to increase chemical stability of the block copolymer membrane. Additionally, or alternatively, branched structures within the hydrophobic B block, such as with PIB, may be expected to induce chain entanglement, which may be expected to enhance the stability of the block copolymer membrane. This may allow for a smaller hydrophobic block to be used, ameliorating the penalty of hydrophobic mismatch towards an inserted nanopore. Additionally, or alternatively, hydrophobic B blocks with relatively low polarity may be expected to be better electrical insulators, thus improving electrical performance of a device for nanopore sequencing (e.g., such as described with reference to FIGS. 32-36).

In some examples of the AB copolymer shown below including PBd as the B block and PEO as the A block, R is reactive group 311, 1211, or 1212; m=about 2 to about 100; and n=about 2 to about 100.

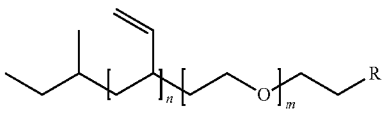

In some nonlimiting examples, R is reactive group 311, 1211, or 1212; n=about 8 to about 50; and m=about 1 to about 20. In some nonlimiting examples, R is reactive group 311, 1211, or 1212; n=about 10 to about 15; and m=about 5 to about 15.

In some examples of the ABA copolymer shown below including one or more PIB blocks as the B block and PEO as the A block, at least one of $R_1$ and $R_2$ may be reactive group 311, 1211, or 1212, and the other of $R_1$ and $R_2$ may be reactive group 311, 1211, or 1212, or may be a group which is not reactive to the chemistry which is used to react 311, 1211, or 1212; V is an optional group that corresponds to a bis-functional initiator from which the isobutylene may be propagated and can be tert-butylbenzene, a phenyl connected to the hydrophobic blocks via the para, meta, or ortho positions, naphthalene, another aromatic group, an alkane chain with between about 2 and about 20 carbons, or another aliphatic group; m=about 2 to about 100; and n=about 2 to about 100. V may optionally be flanked by functional groups selected from the group consisting of a carboxylic acid, a carboxyl group, a methyl group, a hydroxyl group, a primary amine, a secondary amine, a tertiary amine, a biotin, a thiol, an azide, a propargyl group, an allyl group, an acrylate group, a zwitterionic group, a sulfate, a sulfonate, an alkyl group, an aryl group, any orthogonal functionality, and a hydrogen. When V is absent, only one PIB block is present and n=about 2 to about 100. $L_1$ and $L_2$ are independently linkers, which in some examples may be nonreactive, e.g., may include at least one moiety selected from the group consisting of an amide, a thioether (sulfide), a succinic group, a maleic group, a methylene, an ether, and a product of a "click" reaction. In other examples, $L_1$ and/or $L_2$ may be reactive, and may correspond to reactive moieties 311, 1211, or 1212 and may be cross-linked in a manner similar to that described with reference to FIGS. 8A-8B. In such examples, $R_1$ and/or $R_2$ need not necessarily be reactive.

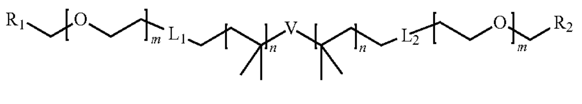

In some nonlimiting examples of the above structure, n=about 2 to about 50, and m=about 1 to about 50, V=tert-butylbenzene, and $L_1$=$L_2$=ethyl sulfide. In other nonlimiting examples, n=about 5 to about 20, m=about 2 to about 15, V=tert-butylbenzene, and $L_1$=$L_2$=ethyl sulfide. In other nonlimiting examples, n=about 13 to about 19, m=about 2 to about 5, V=tert-butylbenzene, and $L_1$=$L_2$=ethyl sulfide. In other nonlimiting examples, n=about 7 to about 13, m=about 7 to about 13, V=tert-butylbenzene, and $L_1$=$L_2$=ethyl sulfide. In particular, in one nonlimiting example, n=16, m=3, V=tert-butylbenzene, and $L_1$=$L_2$=ethyl sulfide. In another nonlimiting example, n=10, m=10, V=tert-butylbenzene, and $L_1$=$L_2$=ethyl sulfide. In another nonlimiting example, n=16, m=8, V=tert-butylbenzene, and $L_1$=$L_2$=ethyl sulfide.

In some examples, multifunctional precursors may be sourced and used as precursors to the synthesis of bifunctional initiators to which V corresponds in the example further above. For example, the multifunctional precursor may be 5-tert-butylisophthalic acid (TBIPA) which can be synthesized into 1-(tert-butyl)-3,5-bis(2-methoxypropan-2-yl)benzene (TBDMPB) using reactions known in the art. In another example, TBIPA may be synthesized into 1-tert-butyl-3,5-bis(2-chloropropan-2-yl)benzene using reactions known in the art. The use of such bifunctional initiators allows cationic polymerization on both sides of the initiator, generating bifunctional PIBs, such as allyl-PIB-allyl, which can then be coupled to hydrophilic A blocks to generate ABA block copolymers including PIB as the B block. Here, although the bifunctional initiator may be located between first and second PIB polymers, it should be understood that the first and second PIB polymers and the bifunctional initiator (V) together may be considered to form a B block, e.g., of an ABA triblock copolymer.

In another nonlimiting example, an ABA triblock copolymer includes

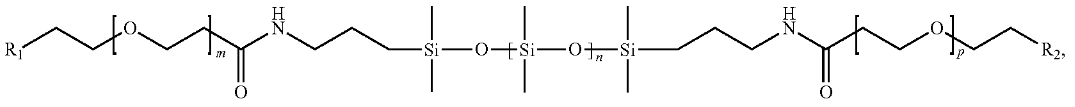

where m=about 2 to about 100, n=about 2 to about 100, p=about 2 to about 100, at least one of $R_1$ and $R_2$ may be reactive group 311, 1211, or 1212 and the other of $R_1$ and $R_2$ may be reactive group 311, 1211, or 1212 or may be a group which is not reactive to the chemistry which is used to react 311, 1211, or 1212. In some nonlimiting examples, m=about 2 to about 30, n=about 25 to about 45, and p=about 2 to about 30. In some nonlimiting examples, m=about 2 to about 15, n=about 30 to about 40, and p=about 2 to about 15. In some nonlimiting examples, m=about 7 to about 11, n=about 35 to about 40, and p=about 7 to about 11. In some nonlimiting examples, m=about 2 to about 5, n=about 30 to about 37, and p=about 2 to about 5. In particular, in one nonlimiting example, m=3, n=34, and p=3. In another nonlimiting example, m=9, n=37, and p=9.

In some examples of the AB copolymer shown below including a PIB block as the B block and PEO as the A block, R is reactive group 311, 1211, or 1212; m=about 2 to about 100; n=about 2 to about 100; and L is a linker. In some examples, L is non-reactive, e.g., is selected from the group consisting of an amide, a thioether (sulfide), a succinic group, a maleic group, a methylene, an ether, or a product of a click reaction. In other examples, L may be reactive, and may correspond to reactive moieties 311, 1211, or 1212 and may be cross-linked in a manner similar to that described with reference to FIGS. 8A-8B. In such examples, R need not necessarily be reactive.

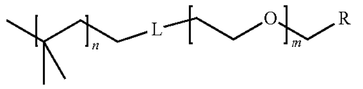

In one nonlimiting example, n=13, m=8, and L is ethyl sulfide. In another nonlimiting example, n=13, m=3, and L is ethyl sulfide. In another nonlimiting example, n=30, m=8, and L is ethyl sulfide. In another nonlimiting example, n=30, m=3, and L is ethyl sulfide.

Figure 16:
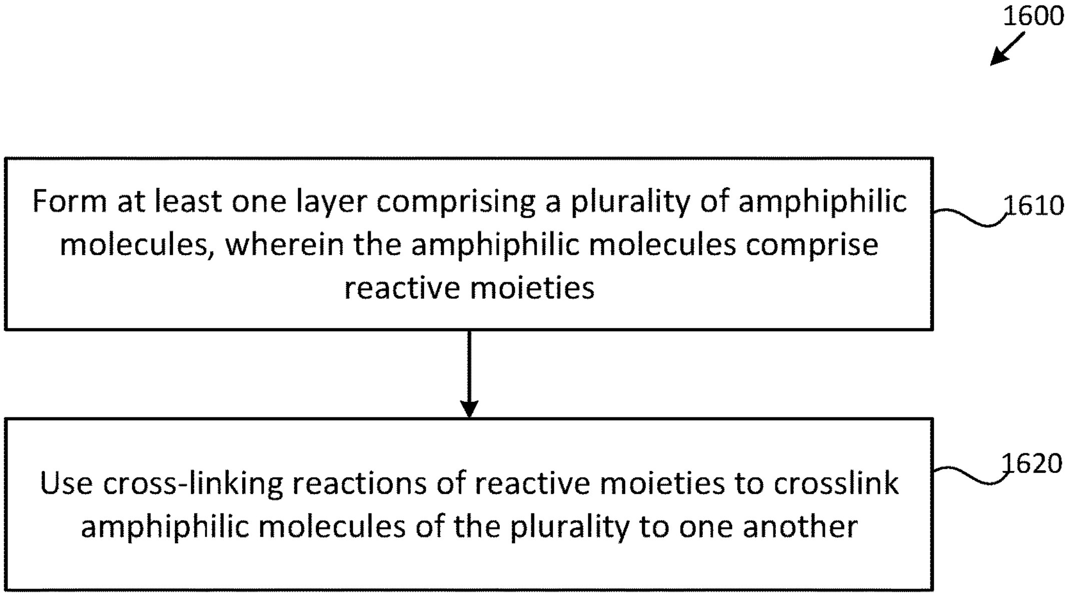
FIG. 16 illustrates an example flow of operations in a method for forming a barrier including cross-linked amphiphilic molecules.

Accordingly, it will be appreciated that a wide variety of amphiphilic molecules and a wide variety of reactive moieties may be used to generate barriers that are stabilized using covalent bonds to molecules, e.g., for use in a nanopore device such as described with reference to FIG. 1. FIG. 16 illustrates an example flow of operations in a method 1600 for forming a barrier including molecules covalently bonded to amphiphilic molecules. Method 1600 may include forming at least one layer including a plurality of amphiphilic molecules, wherein the amphiphilic molecules include reactive moieties (operation 1610). For example, operation 1610 may include forming first and second layers respectively including first and second pluralities of the amphiphilic molecules. In other examples, operation 1610 may include forming a single layer, or a layer which is partially a single layer and partially a bilayer. That is, barrier 101 may include molecules of block copolymers (e.g., AB, ABA, or BAB), which have any suitable arrangement within the barrier, such as described elsewhere herein. The hydrophilic "A" blocks, the hydrophobic "B" blocks, or the A-B interfaces of the amphiphilic molecules (e.g., block copolymers) may be coupled to reactive moieties (e.g., 311, 1211, or 1212) in a manner such as described with reference to FIGS. 3A-14B.

Method 1600 illustrated in FIG. 16 also may include using crosslinking reactions of the reactive moieties to crosslink amphiphilic molecules of the plurality to one another (operation 1620). In examples including first and second layers, the crosslinking reactions may be used to couple amphiphilic molecules of the first layer to one another and/or to amphiphilic molecules of the second layer, and/or may be used to crosslink amphiphilic molecules of the second layer to one another and/or to amphiphilic molecules of the first layer. In some examples of operation 1620, reactive moieties 311 may be used to polymerize the amphiphilic molecules in a manner such as described with reference to FIGS. 3A-11B. In other examples of operation 1620, reactive moieties 1211 and 1212 may be used to couple the amphiphilic molecules to one another in a manner such as described with reference to FIGS. 12A-14B. Optionally, a nanopore may be inserted into the barrier at any suitable time, e.g., before any of the reactions described herein, or after any of the reactions described herein.

Figure 32:
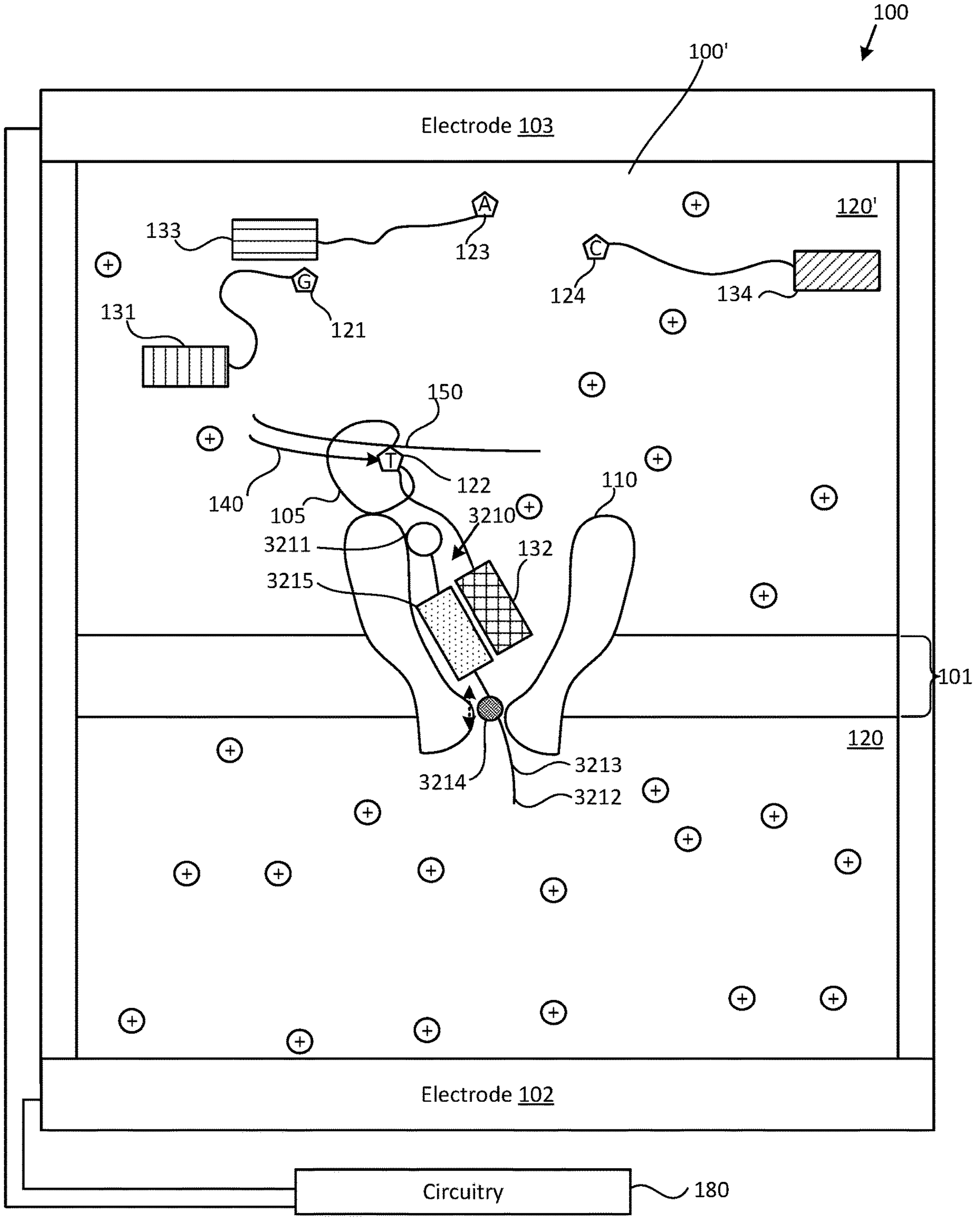
FIG. 32 schematically illustrates a cross-sectional view of an example use of the composition and device of FIG. 1.

It will further be appreciated that the present barriers may be used in any suitable device or application. For example, FIG. 32 schematically illustrates a cross-sectional view of an example use of the composition and device of FIG. 1. Device 100 illustrated in FIG. 32 may be configured to include fluidic well 100', barrier 101 which may have a configuration such as described elsewhere herein, first and second fluids 120, 120', and nanopore 110 in a manner such as described with reference to FIG. 1. In the nonlimiting example illustrated in FIG. 32, second fluid 120' optionally may include a plurality of each of nucleotides 121, 122, 123, 124, e.g., G, T, A, and C, respectively. Each of the nucleotides 121, 122, 123, 124 in second fluid 120' optionally may be coupled to a respective label 131, 132, 133, 134 coupled to the nucleotide via an elongated body (elongated body not specifically labeled). Optionally, device 100 further may include polymerase 105. As illustrated in FIG. 32, polymerase 105 may be within the second composition of second fluid 120'. Alternatively, polymerase 105 may be coupled to nanopore 110 or to barrier 101, e.g., via a suitable elongated body (not specifically illustrated). Device 100 optionally further may include first and second polynucleotides 140, 150 in a manner such as illustrated in FIG. 32. Polymerase 105 may be for sequentially adding nucleotides of the plurality to the first polynucleotide 140 using a sequence of the second polynucleotide 150. For example, at the particular time illustrated in FIG. 32, polymerase 105 incorporates nucleotide 122 (T) into first polynucleotide 140, which is hybridized to second polynucleotide 150 to form a duplex. At other times (not specifically illustrated), polymerase 105 sequentially may incorporate other of nucleotides 121, 122, 123, 124 into first polynucleotide 140 using the sequence of second polynucleotide 150.

Circuitry 180 illustrated in FIG. 32 may be configured to detect changes in an electrical characteristic of the aperture responsive to the polymerase sequentially adding nucleotides of the plurality to the first polynucleotide 140 using a sequence of the second polynucleotide 150. In the nonlimiting example illustrated in FIG. 32, nanopore 110 may be coupled to permanent tether 3210 which may include head region 3211, tail region 3212, elongated body 3213, reporter region 3214 (e.g., an abasic nucleotide), and moiety 3215. Head region 3211 of tether 3210 is coupled to nanopore 110 via any suitable chemical bond, protein-protein interaction, or any other suitable attachment that is normally irreversible. Head region 3211 can be attached to any suitable portion of nanopore 110 that places reporter region 3214 within aperture 3213 and places moiety 3215 sufficiently close to polymerase 105 so as to interact with respective labels 131, 132, 133, 134 of nucleotides 121, 122, 123, 124 that are acted upon by polymerase 105. Moiety 3215 respectively may interact with labels 131, 132, 133, 134 in such a manner as to move reporter region 3214 within aperture 113 and thus alter the rate at which salt 160 moves through aperture 113, and thus may detectably alter the electrical conductivity of aperture 113 in such a manner as to be detected by circuitry 180. For further details regarding use of permanent tethers coupled to nanopores to sequence polynucleotides, see U.S. Pat. No. 9,708,655, the entire contents of which are incorporated by reference herein.

Figure 33:
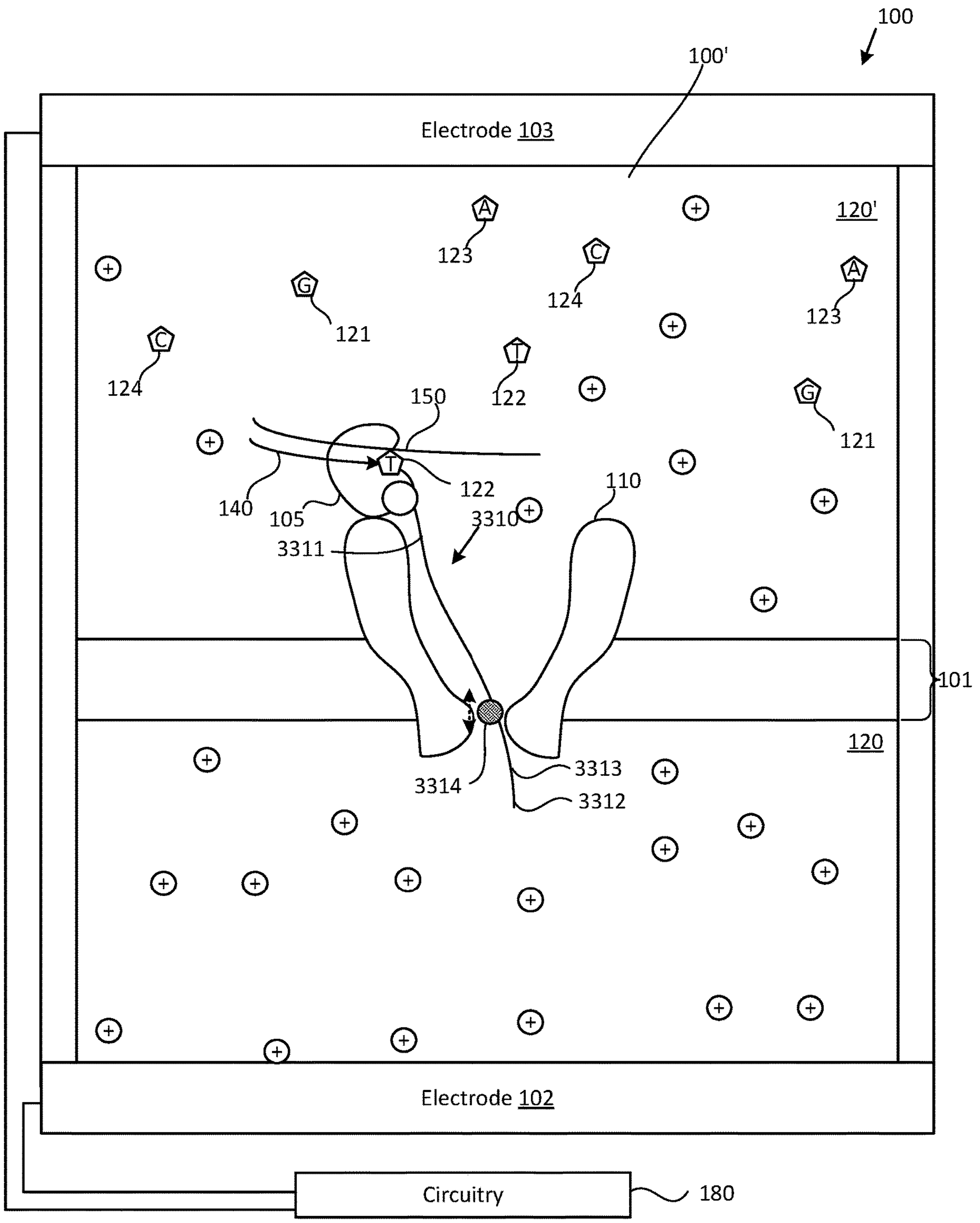
FIG. 33 schematically illustrates a cross-sectional view of another example use of the composition and device of FIG. 1.

FIG. 33 schematically illustrates a cross-sectional view of another example use of the composition and device of FIG. 1. As illustrated in FIG. 33, device 100 may include fluidic well 100', barrier 101 which may have a configuration such as described elsewhere herein, first and second fluids 120, 120', nanopore 110, and first and second polynucleotides 140, 150, all of which may be configured similarly as described with reference to FIG. 32. In the nonlimiting example illustrated in FIG. 33, nucleotides 121, 122, 123, 124 need not necessarily be coupled to respective labels. Polymerase 105 may be coupled to nanopore 110 and may be coupled to permanent tether 3310 which may include head region 3311, tail region 3312, elongated body 3313, and reporter region 3314 (e.g., an abasic nucleotide). Head region 3311 of tether 3310 is coupled to polymerase 105 via any suitable chemical bond, protein-protein interaction, or any other suitable attachment that is normally irreversible. Head region 3311 can be attached to any suitable portion of polymerase 105 that places reporter region 3314 within aperture 113. As polymerase 105 interacts with nucleotides 121, 122, 123, 124, such interactions may cause polymerase 105 to undergo conformational changes. Such conformational changes may move reporter region 3314 within aperture 113 and thus alter the rate at which salt 160 moves through aperture 113, and thus may detectably alter the electrical conductivity of aperture 113 in such a manner as to be detected by circuitry 180. For further details regarding use of permanent tethers coupled to polymerases to sequence polynucleotides, see U.S. Pat. No. 9,708,655, the entire contents of which are incorporated by reference herein.

Figure 34:
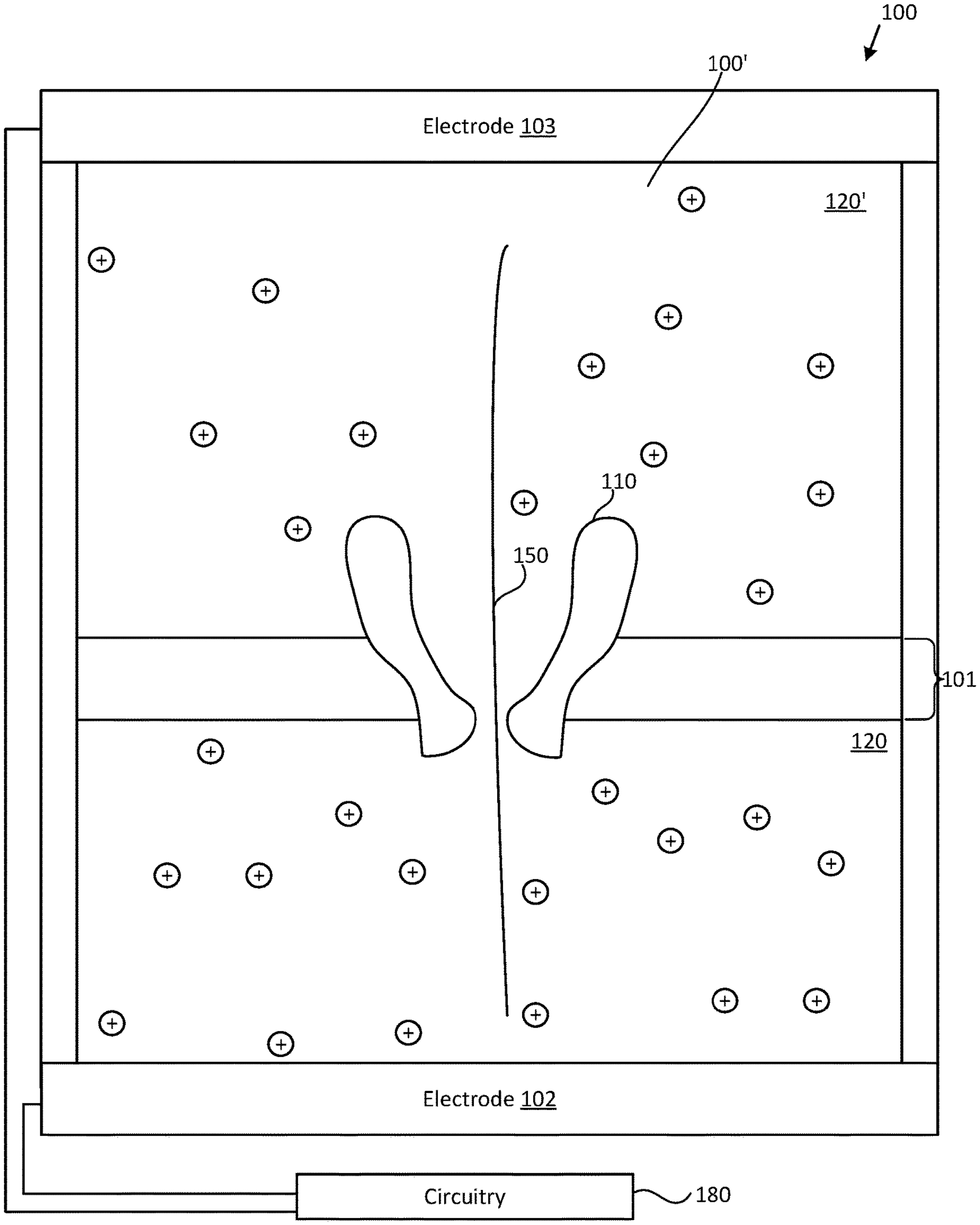
FIG. 34 schematically illustrates a cross-sectional view of another example use of the composition and device of FIG. 1.

FIG. 34 schematically illustrates a cross-sectional view of another example use of the composition and device of FIG. 1. As illustrated in FIG. 34, device 100 may include fluidic well 100', barrier 101 which may have a configuration such as described elsewhere herein, first and second fluids 120, 120', and nanopore 110 all of which may be configured similarly as described with reference to FIG. 32. In the nonlimiting example illustrated in FIG. 34, polynucleotide 150 is translocated through nanopore 110 under an applied force, e.g., a bias voltage that circuitry 180 applies between electrode 102 and electrode 103. As bases in polynucleotide 150 pass through nanopore 110, such bases may alter the rate at which salt 160 moves through aperture 113, and thus may detectably alter the electrical conductivity of aperture 113 in such a manner as to be detected by circuitry 180. For further details regarding use of nanopores to sequence polynucleotides being translocated therethrough, see U.S. Pat. No. 5,795,782, the entire contents of which are incorporated by reference herein.

Figure 35:
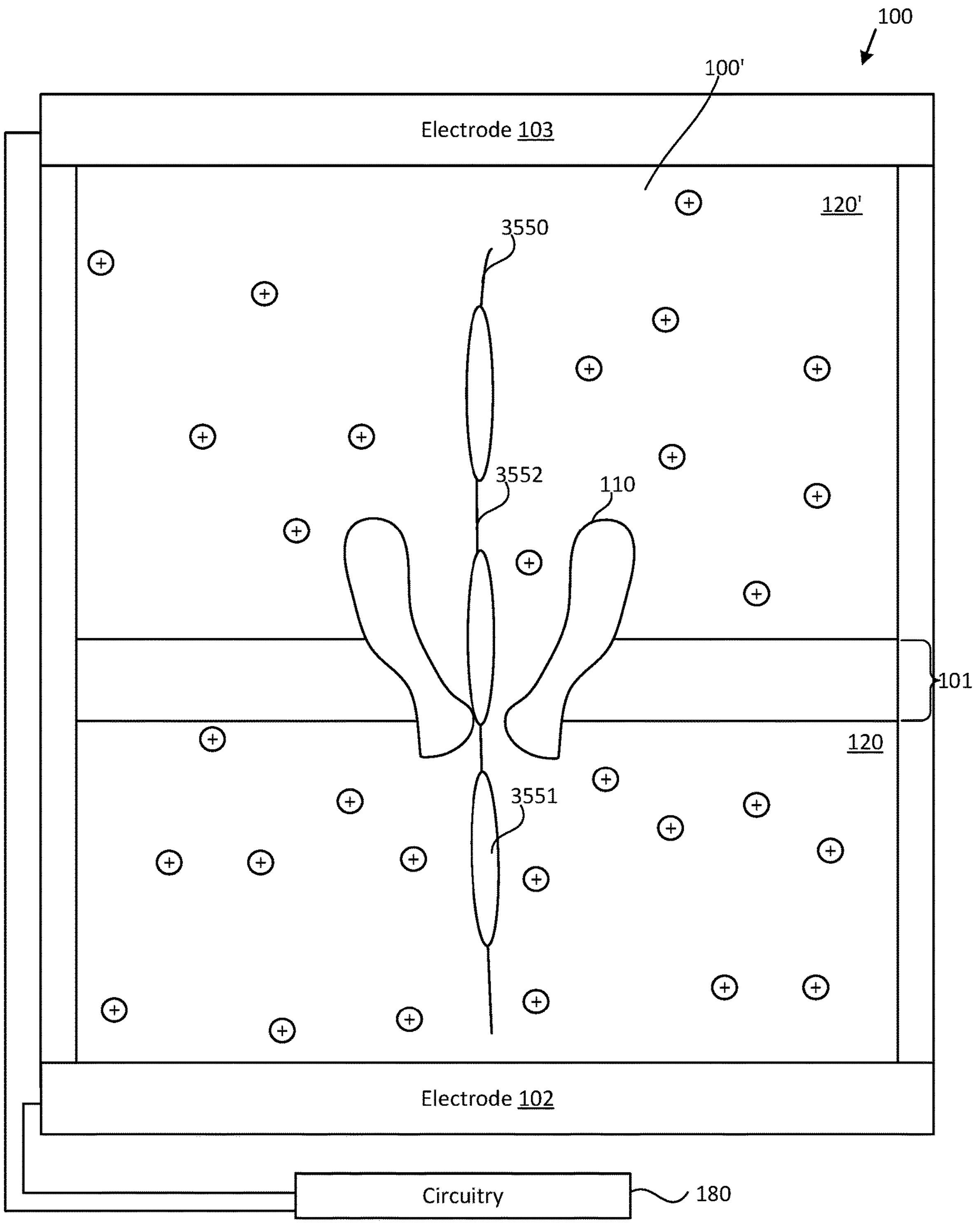
FIG. 35 schematically illustrates a cross-sectional view of another example use of the composition and device of FIG. 1.

FIG. 35 schematically illustrates a cross-sectional view of another example use of the composition and device of FIG. 1. As illustrated in FIG. 35, device 100 may include fluidic well 100', barrier 101 which may have a configuration such as described elsewhere herein, first and second fluids 120, 120', and nanopore 110 all of which may be configured similarly as described with reference to FIG. 32. In the nonlimiting example illustrated in FIG. 35, surrogate polymer 3550 is translocated through nanopore 110 under an applied force, e.g., a bias voltage that circuitry 180 applies between electrode 102 and electrode 103. As used herein, a "surrogate polymer" is intended to mean an elongated chain of labels having a sequence corresponding to a sequence of nucleotides in a polynucleotide. In the example illustrated in FIG. 35, surrogate polymer 3550 includes labels 3551 coupled to one another via linkers 3552. An XPANDOMER™ is a particular type of surrogate polymer developed by Roche Sequencing, Inc. (Pleasanton, CA). XPANDOMERS™ may be prepared using Sequencing By eXpansion™ (SBX™, Roche Sequencing, Pleasanton CA). In Sequencing by eXpansion™, an engineered polymerase polymerizes xNTPs which include nucleobases coupled to labels via linkers, using the sequence of a target polynucleotide. The polymerized nucleotides are then processed to generate an elongated chain of the labels, separated from one another by linkers which are coupled between the labels, and having a sequence that is complementary to that of the target polynucleotide. For example descriptions of XPANDOMERS™, linkers (tethers), labels, engineered polymerases, and methods for SBX™, see the following patents, the entire contents of each of which are incorporated by reference herein: U.S. Pat. Nos. 7,939,249, 8,324,360, 8,349,565, 8,586,301, 8,592,182, 9,670,526, 9,771,614, 9,920,386, 10,301,345, 10,457,979, 10,676,782, 10,745,685, 10,774,105, and 10,851,405.

Figure 36:
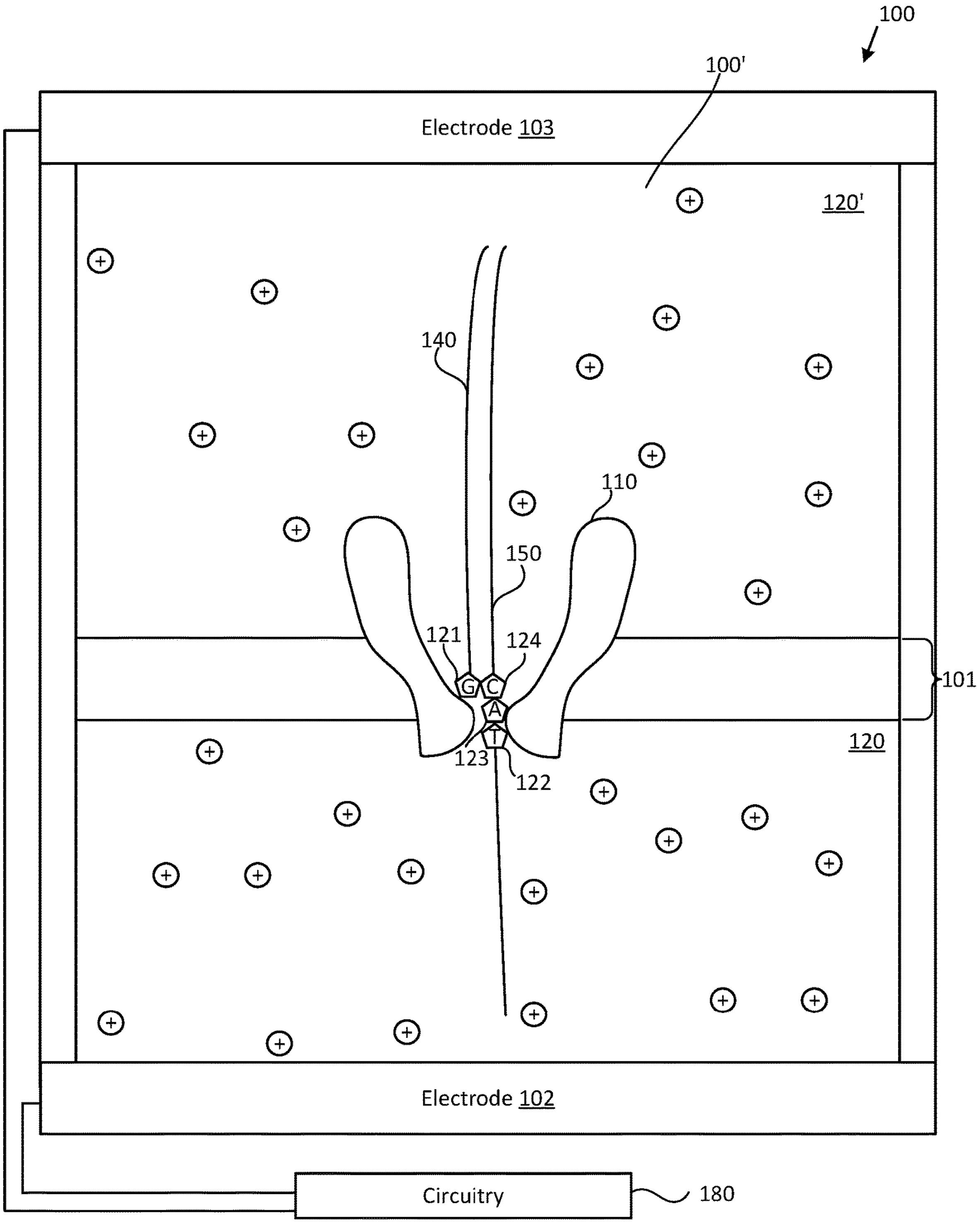
FIG. 36 schematically illustrates a cross-sectional view of another example use of the composition and device of FIG. 1.

FIG. 36 schematically illustrates a cross-sectional view of another example use of the composition and device of FIG. 1. As illustrated in FIG. 36, device 100 may include fluidic well 100', barrier 101 which may have a configuration such as described with reference to FIGS. 2A-2C, 14A-14B, 15, and/or 16 (that is, barrier 101 optionally may be suspended using a barrier support, and may include any AB, ABA, or BAB copolymer provided herein), first and second fluids 120, 120', and nanopore 110 all of which may be configured similarly as described with reference to FIG. 4. In the nonlimiting example illustrated in FIG. 36, a duplex between polynucleotide 140 and polynucleotide 150 is located within nanopore 110 under an applied force, e.g., a bias voltage that circuitry 180 applies between electrode 102 and electrode 103. A combination of bases in the double-stranded portion (here, the base pair GC 121, 124 at the terminal end of the duplex) and bases in the single-stranded portion of polynucleotide 150 (here, bases A and T 123, 122) may alter the rate at which salt 160 moves through aperture 113, and thus may detectably alter the electrical conductivity of aperture 113 in such a manner as to be detected by circuitry 180. For further details regarding use of nanopores to sequence polynucleotides being translocated therethrough, see US Patent Publication No. 2023/0090867 to Mandell et al., the entire contents of which are incorporated by reference herein.

WORKING EXAMPLES

The following examples are intended to be purely illustrative, and not limiting of the present invention.

Figure 17:
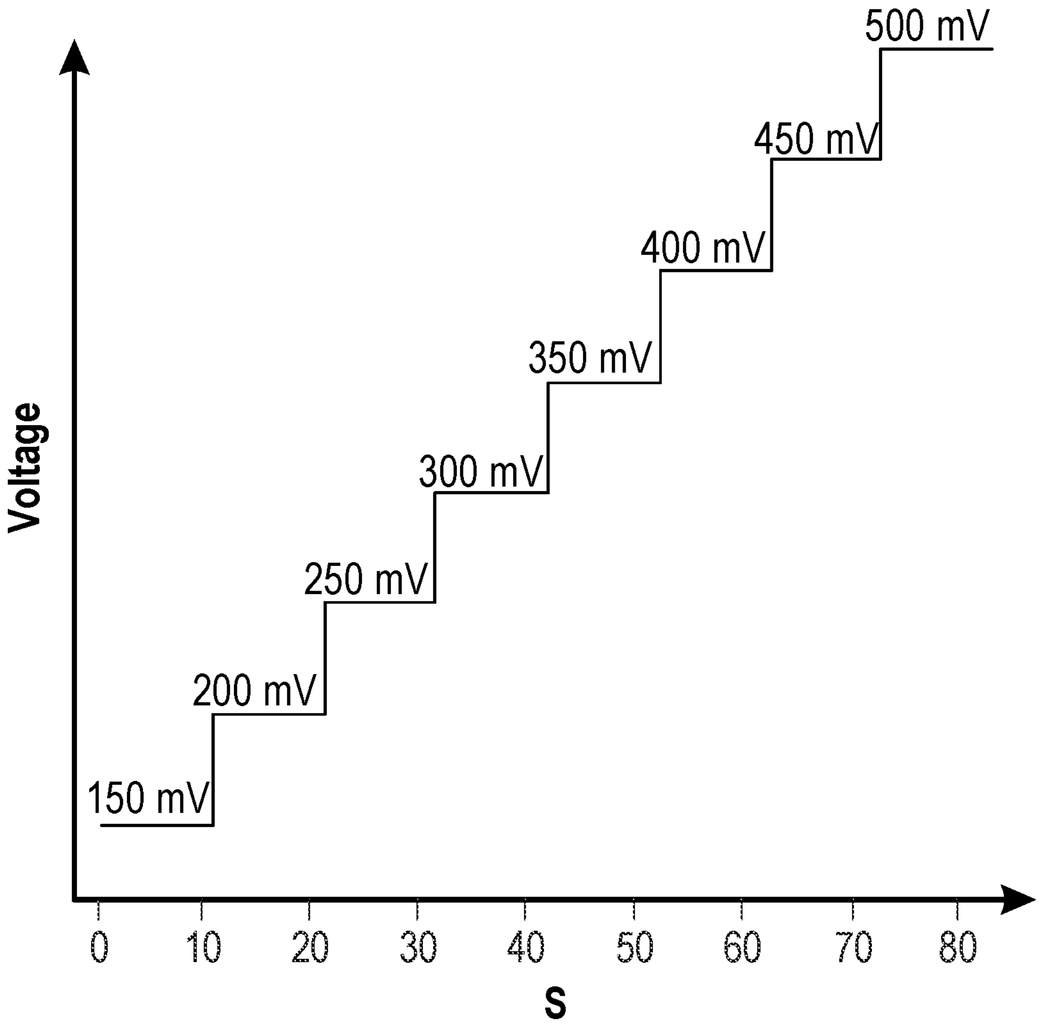
FIG. 17 illustrates the voltage breakdown waveform used to assess polymeric membrane stability.

The performances of different membranes were assessed in terms of membrane stability. Membranes suspended by barriers with circular apertures were generated, and then characterized using an automated patch clamp device using Ag/AgCl electrodes. FIG. 17 illustrates the voltage breakdown waveform used to assess polymeric membrane stability. Membrane stability was quantified as the percentage of membranes remaining at the end of each step of the voltage ramp illustrated. The voltage ramp was stepped in 50 mV steps from 150 mV to 500 mV, as shown in FIG. 17. Each step lasted for 10 seconds. The membranes were painted using the Orbit 16 TC platform using standard buffer conditions (1M KCl, 50 mM HEPES, pH=7.4).

Example 1

In Example 1, polymer 1, a PDMS-b-PEO-acrylate polymer (AB polymer with reactive acrylate moieties at the ends of the A blocks) was mixed with polymer 2, a succinate-b-PDMS-b-succinate polymer (ABA polymer with succinate acid as the A blocks) were mixed together in a 4:1 ratio and used to form membranes such as described with reference to FIG. 3A. Structures of these polymers are shown below:

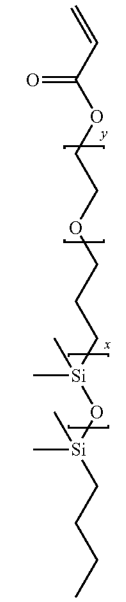

Polymer 1, PDMS-b-PEO-acrylate, in which the A block included about 8-9 PEO repeating units (RU) and the B block included about 19-20 PDMS RU, in which the acrylate moiety is coupled to the terminal PEO via an ester bond; and

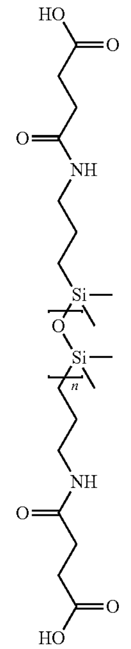

Polymer 2, succinate-PDMS-succinate, in which the A blocks included about 1 succinate acid RU and the B block included about 41 RU, in which the succinate moiety is coupled to the terminal PDMS via an amide bond.

Figure 18A:
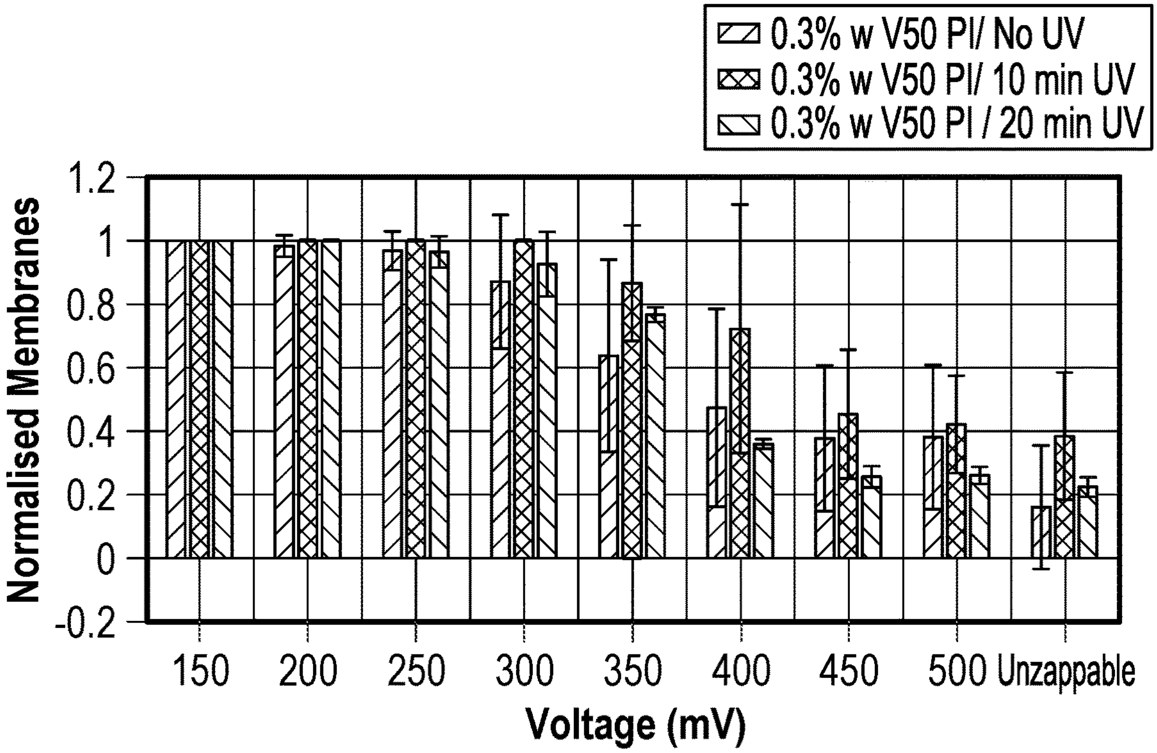
FIG. 18A is a plot of the measured membrane stability for membranes that were crosslinked using a photoinitiator under different conditions.

The membranes were crosslinked using polymerization under a variety of conditions in a manner such as described with reference to FIG. 3B, and their stability measured using the waveform described with reference to FIG. 17. FIG. 18A is a plot of the measured membrane stability for membranes that were crosslinked using a photoinitiator under different conditions. More specifically, during formation of the membranes, the 4:1 mixture of polymer 1 and polymer 2 was mixed with 0.3 wt % of the photoinitiator (PI) V50. A first subset of the membranes were exposed to UV light at about 1350 mW and a wavelength of about 365 nm for 10 minutes; a second subset of the membranes were exposed to UV light for 20 minutes; and a third subset of the membranes were not exposed to UV light as a control. From FIG. 18A it may be seen that the membranes that were exposed to the UV light for 10 minutes had the greatest stability at increased voltages, while the membranes that were exposed to the UV light for 20 minutes had stability that was lower than those exposed for 10 minutes, and in some cases was lower than those which were not exposed to UV. Membranes deemed "unzappable" were those which remained stable at a voltage of about 1 V, the highest voltage that could be generated using the system, for at least about 100 ms. From these results, it may be understood that the duration of UV exposure suitably may be adjusted to result in a desired degree of crosslinking and stability.

Figure 18B:
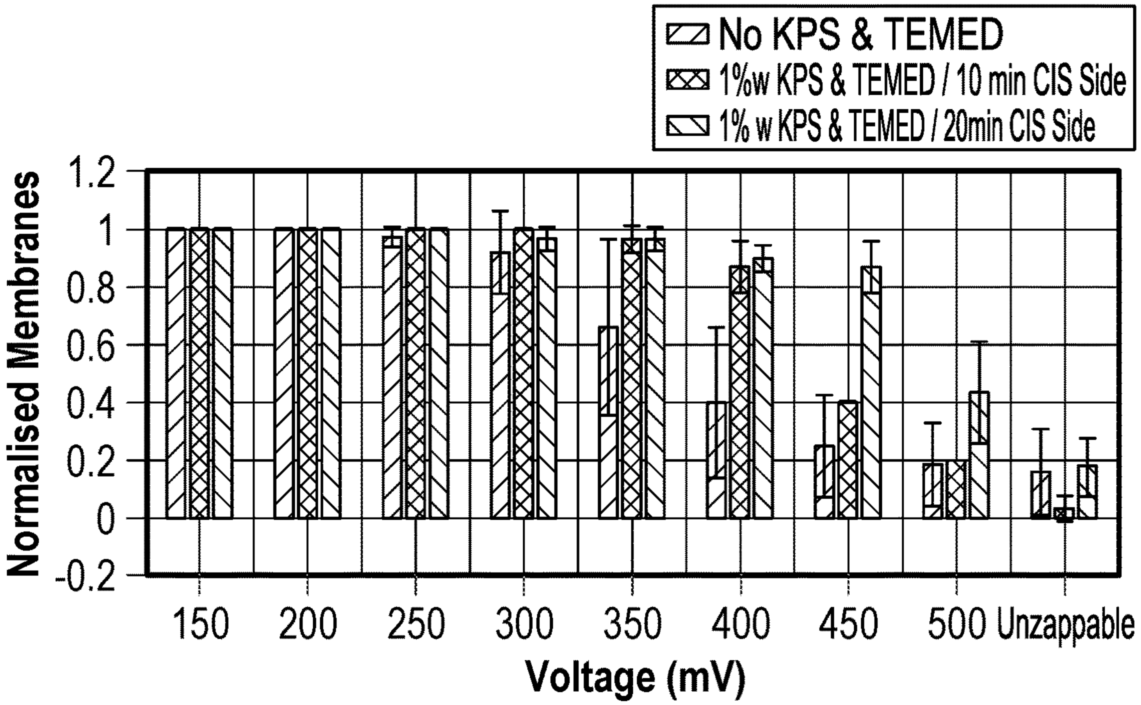
FIG. 18B is a plot of the measured membrane stability for membranes that were crosslinked using a redox system under different conditions.

FIG. 18B is a plot of the measured membrane stability for membranes that were crosslinked using a redox system under different conditions. More specifically, the 4:1 mixture of polymer 1 and polymer 2 was used to form membranes. For some membranes, the buffer solution on the second (cis) side 112 of the membranes was exchanged with a similar buffer solution containing 1 wt % each of KPS and TEMED. A first subset of the membranes were incubated with the KPS/TEMED mixture for 10 minutes; a second subset of the membranes incubated with the KPS/TEMED mixture for 20 minutes; and a third subset of the membranes were not incubated with the KPS/TEMED mixture as a control. From FIG. 18B it may be seen that the membranes that were incubated with KPS/TEMED had the greatest stability at all voltages, while the membranes that were incubated for 10 minutes had stability that was lower than those exposed for 20 minutes, and the membranes that were not incubated with KPS/TEMED had the lowest stability. From these results, it may be understood that the duration of redox system exposure suitably may be adjusted to result in a desired degree of crosslinking and stability.

Figure 18C:
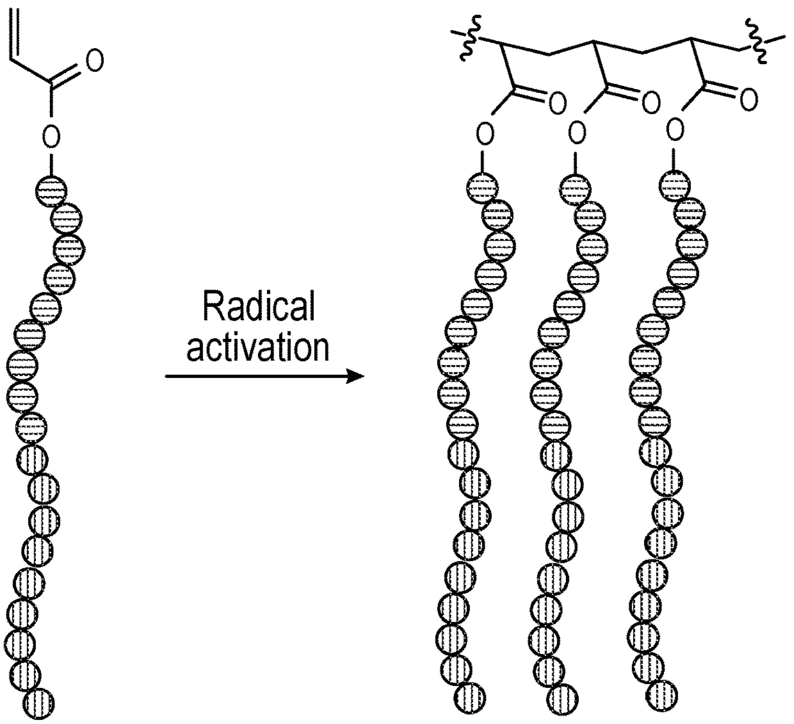
FIG. 18C schematically illustrates an example reaction product in the membranes that were crosslinked as described with reference to FIGS. 18A-18B.

FIG. 18C schematically illustrates an example reaction product in the membranes that were crosslinked as described with reference to FIGS. 18A-18B. As shown in FIG. 18C, the reaction product of the polymerization of the acrylate moieties of polymer 1 includes polyacrylate formed in a plane at the ends of the A blocks of the block copolymer. Note that although a second layer of the AB copolymer is not shown, in some examples a similar reaction product may be formed in a plane at the ends of such A blocks in a second layer, e.g., in examples in which both sides of the membrane are contacted with the initiator. In other examples, the polyacrylate substantially may be formed only at the ends of the A blocks in a first layer, e.g., in examples in which only the ends of that layer are contacted with the initiator.

Example 2

In Example 2, polymer 3, a maleic-b-PDMS-b-maleic polymer (ABA polymer with reactive maleic acid moieties at the terminal ends of the A blocks) was used to form membranes such as described with reference to FIG. 5A. The structure of polymer 3 is shown below:

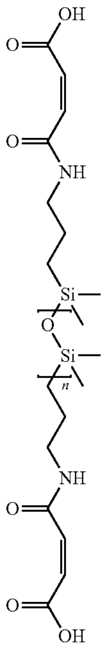

Polymer 3, in which the A blocks included about 1 maleic acid RU and the B block included about 41 PDMS RU, in which the maleic moieties are coupled to the A blocks via respective amide bonds.

Figure 19A:
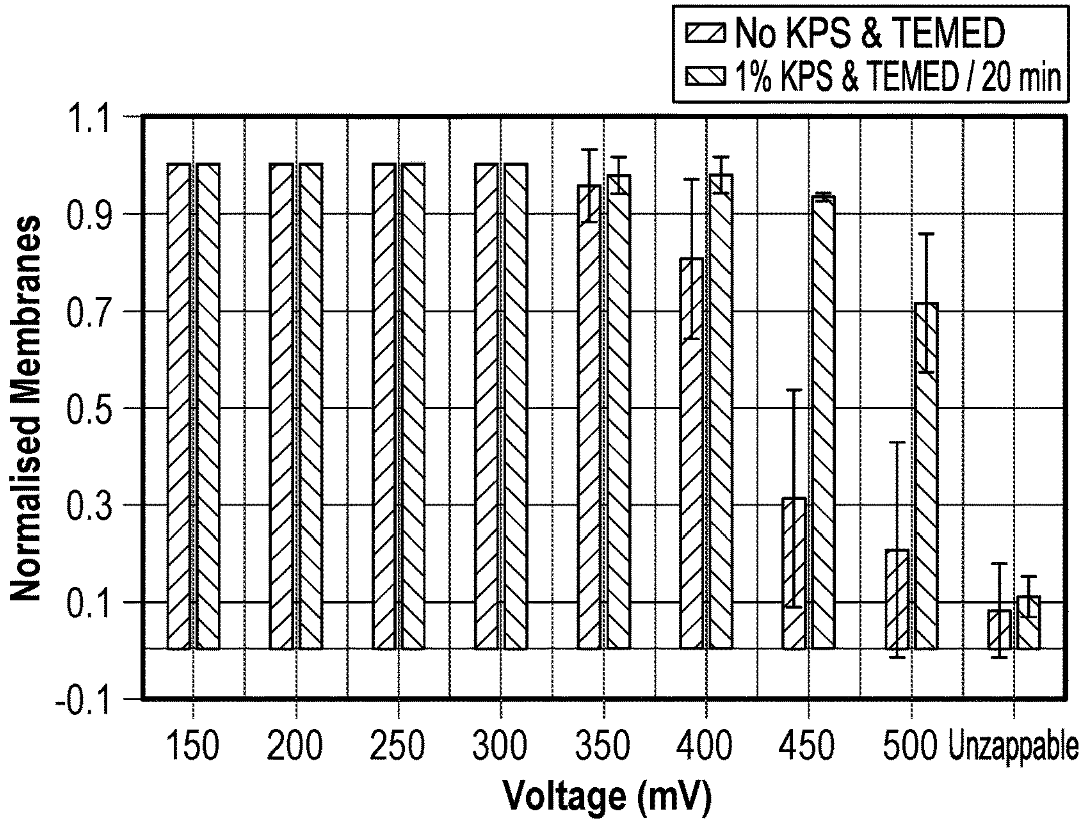
FIG. 19A is a plot of the measured membrane stability for membranes that were crosslinked using a redox system.

The membranes were crosslinked in a manner such as described with reference to FIG. 5B, and their stability measured using the waveform described with reference to FIG. 17. FIG. 19A is a plot of the measured membrane stability for membranes that were crosslinked using a redox system. More specifically, after forming the membranes the buffer solution on the second (cis) side 112 of the membranes was exchanged with a similar buffer solution containing 1 wt % each of KPS and TEMED. A first subset of the membranes were incubated with the KPS/TEMED mixture for 20 minutes; a second subset of the membranes were not incubated with the KPS/TEMED mixture as a control. From FIG. 19A it may be seen that the membranes that were incubated with KPS/TEMED had higher stability at higher voltages than those that were not incubated with KPS/TEMED. From these results, it may be understood that crosslinking enhanced stability of the membranes.

Figure 19B:
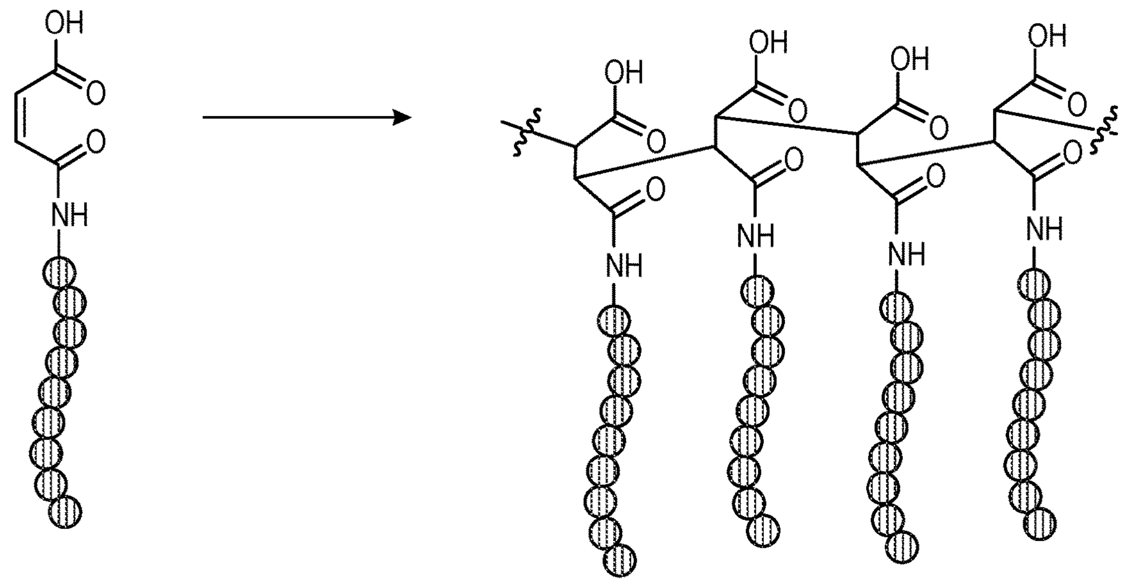
FIG. 19B schematically illustrates an example reaction product in the membranes that were crosslinked as described with reference to FIG. 19A.

FIG. 19B schematically illustrates an example reaction product in the membranes that were crosslinked as described with reference to FIG. 19A. As shown in FIG. 19A, the reaction product of the polymerization of the maleic moieties of polymer 3 includes poly(maleic acid derivative) formed in a plane at the ends of the A blocks of the block copolymer—where in this specific example, the A blocks are formed by a single maleic moiety, but in other implementations, the A block maybe be formed by a hydrophilic polymer with a terminal maleic moiety. Note that although the maleic moieties on the other side of the membrane are not shown, in some examples a similar reaction product may be formed in a plane on the other side of the membrane, e.g., in examples in which both sides of the membrane are contacted with the initiator. In other examples, the reaction product substantially may be formed only at the ends of one set of the A blocks, e.g., in examples in which only one side of the membrane is contacted with the initiator.

Example 3

In example 3, a PEO-b-maleic-PDMS-b-maleic-PEO polymer (ABA polymer with reactive maleic acid moieties at the A-B interface) is used to form membranes such as described with reference to FIG. 8A. The structure of polymer 4 is shown below:

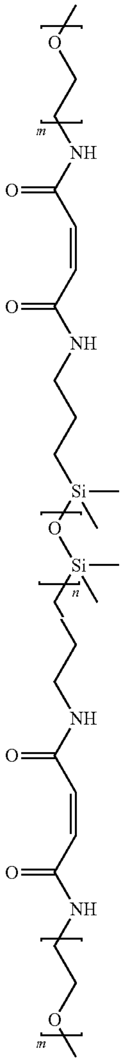

Polymer 4, in which the A blocks included about 8 PEO RU and the B block included about 41 PDMS RU, in which the maleic moieties are coupled to the A and B blocks via respective amide bonds.

Figure 20:
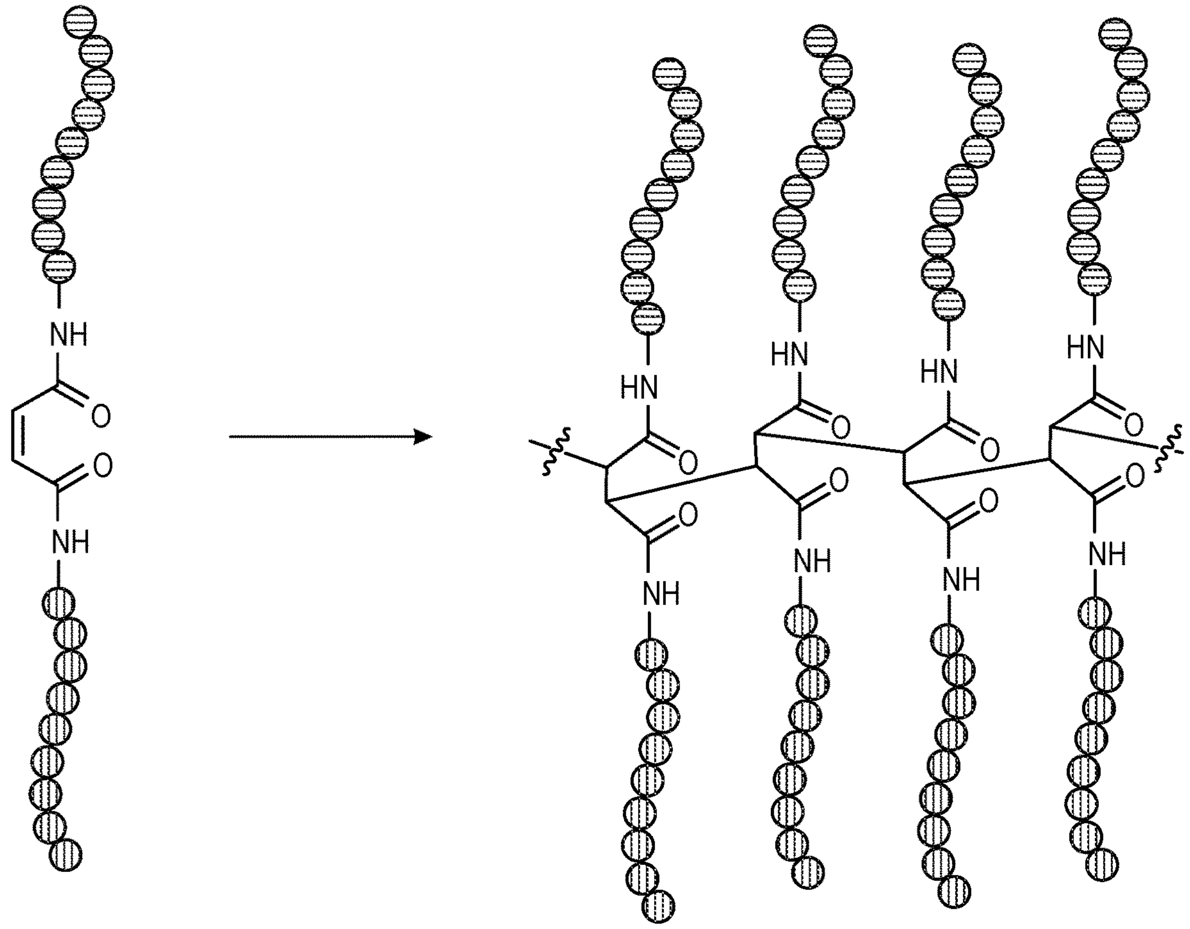
FIG. 20 schematically illustrates an example reaction product in the membranes that are crosslinked as described in Example 3.

The membranes are crosslinked in a manner such as described with reference to FIG. 8B. FIG. 20 schematically illustrates an example reaction product in the membranes that are crosslinked as described in Example 3. As shown in FIG. 20, the reaction product of the polymerization of the maleic moieties of polymer 4 includes poly(maleic acid derivative) formed in a plane at the A-B interface of the block copolymer. Note that although the maleic moieties on the other side of the membrane are not shown, in some examples a similar reaction product may be formed in a plane on the other side of the membrane.

Example 4

In Example 4, polymer 5, a propargyl-PEO-b-PDMS-b-PEO-propargyl polymer (ABA polymer with reactive propargyl moieties at the ends of the A blocks) was mixed with polymer 6, a disulfide pyridyl-PEO-b-PDMS-b-PEO-disulfide pyridyl polymer (ABA polymer with disulfide pyridyl moieties at the ends of the A blocks) were mixed together in a 1:2 ratio and used to form membranes such as described with reference to FIGS. 12A-12B. Structures of these polymers are shown below:

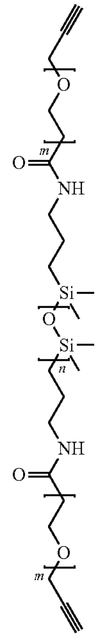

Polymer 5, in which the A block included about 8 PEO RU and the B block included about 41 PDMS RU, in which the propargyl moieties are coupled to the terminal PEOs via respective ether bonds; and

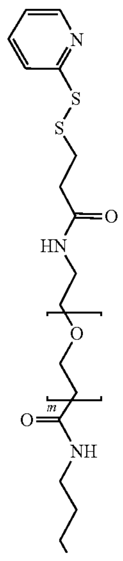

-continued

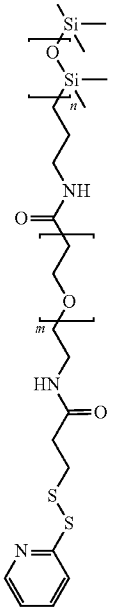

Polymer 6, in which the A blocks included about 8 PEO RU and the B block included about 41 RU, in which the disulfide pyridyl moieties are coupled to the terminal PEOs via respective amide bonds.

Figure 21A:
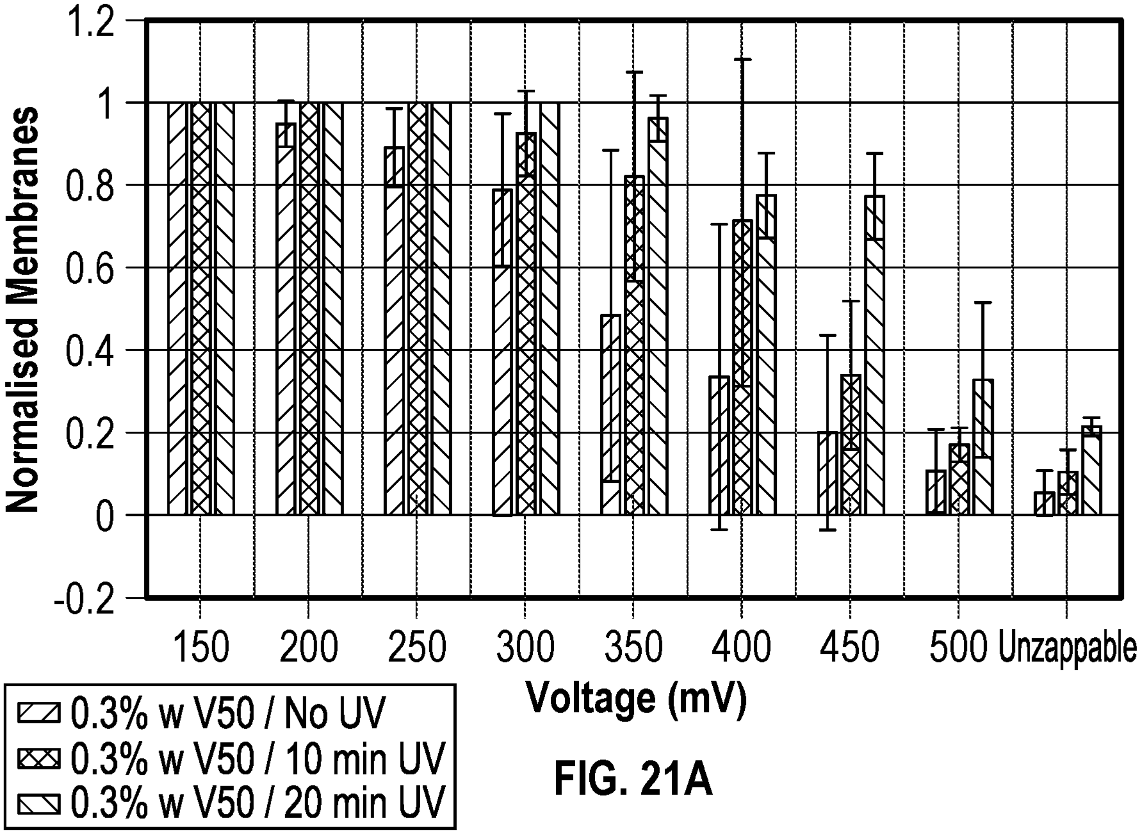
FIG. 21A is a plot of the measured membrane stability for membranes that were crosslinked using a first photoinitiator under different conditions.

The membranes were crosslinked using coupling reactions under a variety of conditions in a manner such as described with reference to FIGS. 12A-12B and 13, and their stability measured using the waveform described with reference to FIG. 17. FIG. 21A is a plot of the measured membrane stability for membranes that were crosslinked using a first photoinitiator under different conditions. More specifically, during formation of the membranes, the 1:2 mixture of polymer 5 and polymer 6 was mixed with 0.3 wt % of the photoinitiator (PI) V50. A first subset of the membranes were exposed to UV light at about 1350 mW and a wavelength of about 365 nm for 10 minutes; a second subset of the membranes were exposed to UV light for 20 minutes; and a third subset of the membranes were not exposed to UV light as a control. From FIG. 21A it may be seen that the membranes that were exposed to the UV light for 10 minutes had the greatest stability at higher voltages, while the membranes that were exposed to the UV light for 10 minutes had stability that was lower than those exposed for 10 minutes, and those which were not exposed to UV had the lowest stability. From these results, it may be understood that the duration of UV exposure suitably may be adjusted to result in a desired degree of crosslinking and stability.

Figure 21B:
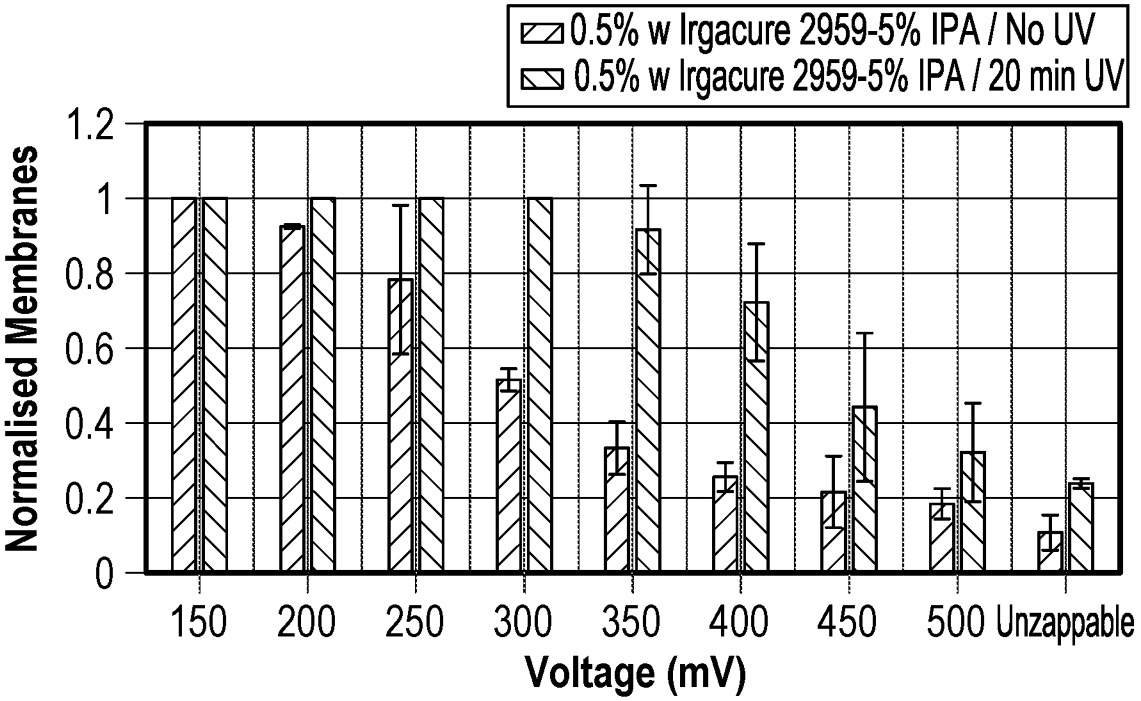
FIG. 21B is a plot of the measured membrane stability for membranes that were crosslinked using a second photoinitiator.

FIG. 21B is a plot of the measured membrane stability for membranes that were crosslinked using a second photoinitiator. More specifically, during formation of the membranes, the 1:2 mixture of polymer 5 and polymer 6 was mixed with 0.5 wt % of the PI Irgacure 2959 with 5 wt % isopropyl alcohol (IPA). A first subset of the membranes were exposed to UV light at about 1350 mW and a wavelength of about 365 nm for 20 minutes; and a second subset of the membranes were not exposed to UV light as a control. From FIG. 21B it may be seen that the membranes that were exposed to the UV light for 20 minutes had the greatest stability at higher voltages, while the membranes that were not exposed to the UV light had the lowest stability. From these results, it may be understood that the duration of UV exposure suitably may be adjusted to result in a desired degree of crosslinking and stability.

Figure 21C:
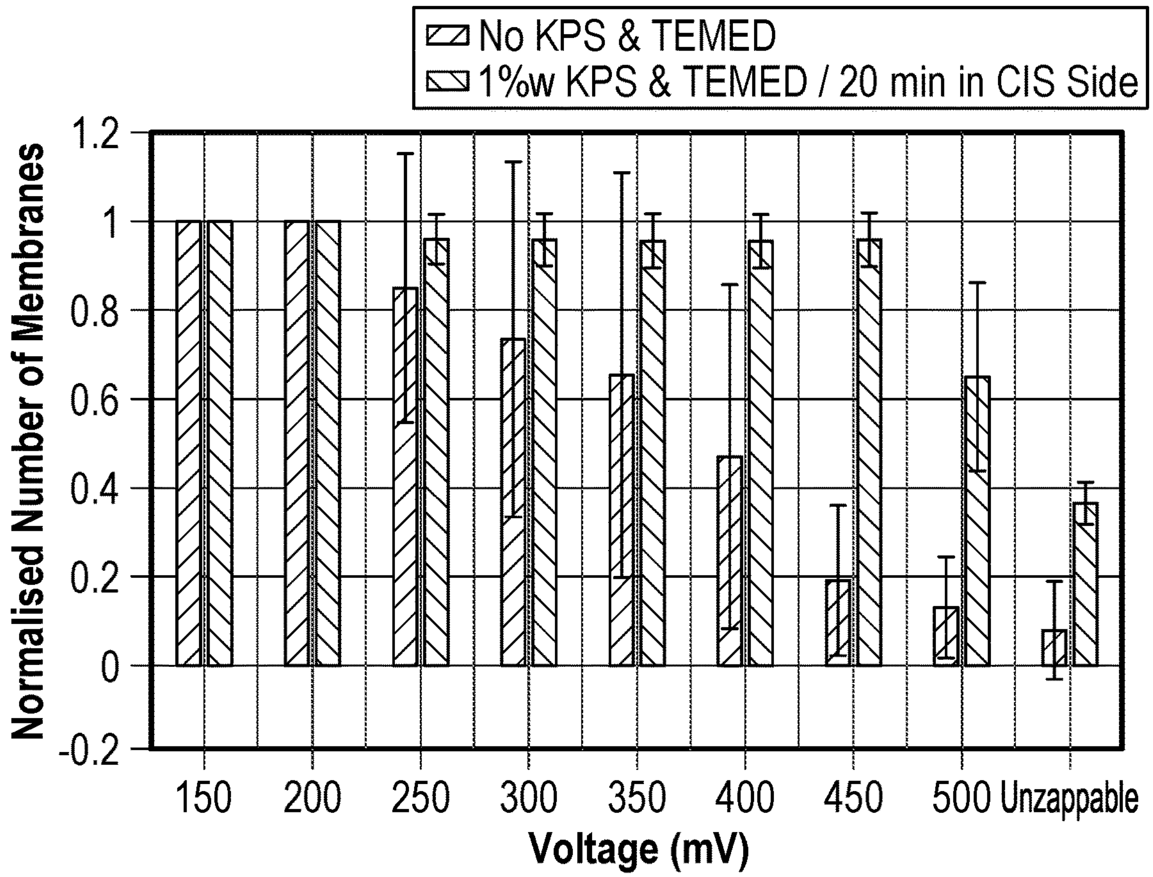
FIG. 21C is a plot of the measured membrane stability for membranes that were crosslinked using a redox system.

FIG. 21C is a plot of the measured membrane stability for membranes that were crosslinked using a redox system. More specifically, the 1:2 mixture of polymer 5 and polymer 6 was used to form membranes. For some membranes, the buffer solution on the second (cis) side 112 of the membranes was exchanged with a similar buffer solution containing 1 wt % each of KPS and TEMED. A first subset of the membranes were incubated with the KPS/TEMED mixture for 20 minutes; and a second subset of the membranes were not incubated with the KPS/TEMED mixture as a control. From FIG. 21C it may be seen that the membranes that were incubated with KPS/TEMED had the greatest stability at higher voltages, and the membranes that were not incubated with KPS/TEMED had the lowest stability. From these results, it may be understood that the duration of redox system exposure suitably may be adjusted to result in a desired degree of crosslinking and stability.

Figure 21D:
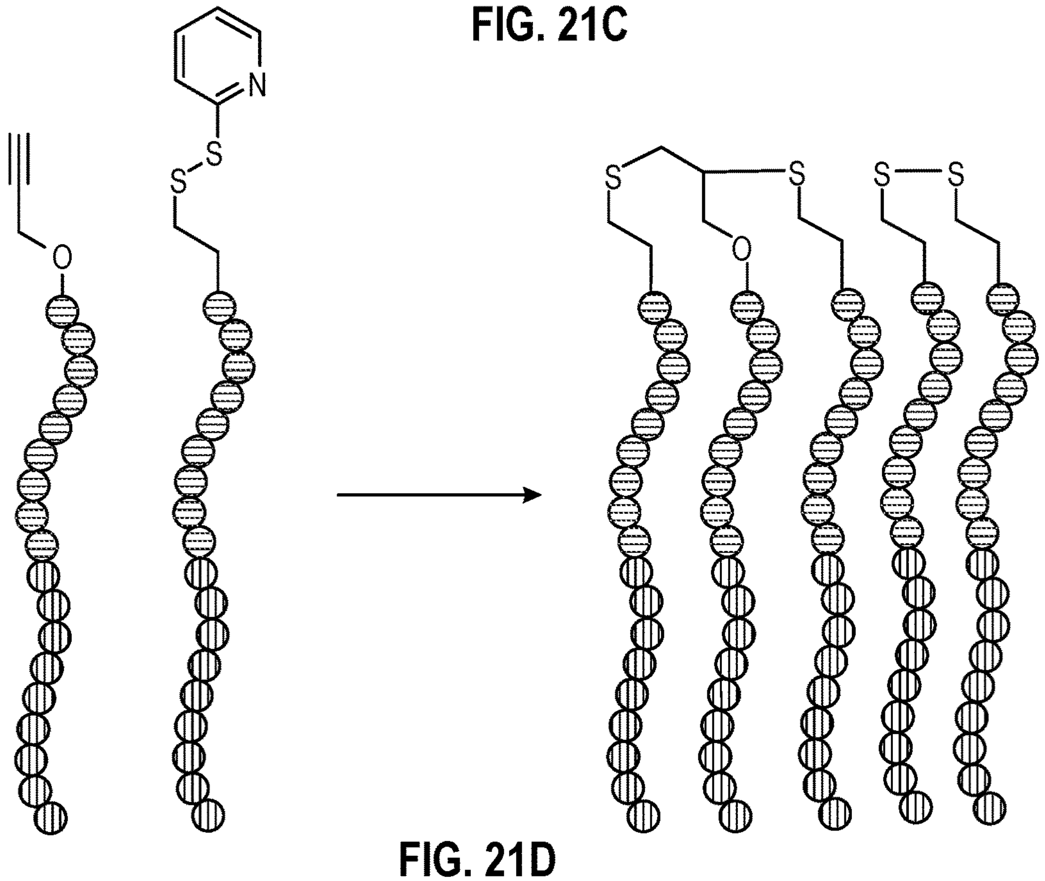
FIG. 21D schematically illustrates an example reaction product in the membranes that were crosslinked as described with reference to FIGS. 21A-21C.

FIG. 21D schematically illustrates an example reaction product in the membranes that were crosslinked as described with reference to FIGS. 21A-21C. As shown in FIG. 21D, the reaction product of thiol-yne click coupling between the propargyl moieties of polymer 5 and the disulfide pyridyl moieties of polymer 6 includes sulfide bonds formed in a plane at the ends of the A blocks of the block copolymer. Note that the other end of the ABA copolymer is not shown, in some examples similar reaction products may be formed in a plane at the ends of the other A blocks, e.g., in examples in which both sides of the membrane are contacted with the initiator. In other examples, the reaction products substantially may be formed only at the ends of the A blocks on the first side of the membrane, e.g., in examples in which only that side of the membrane is contacted with the initiator.

Example 5

In Example 5, polymer 5 (the propargyl-PEO-b-PDMS-b-PEO-propargyl ABA polymer of Example 4) is mixed with polymer 7, a lipoamido-PEO-b-PDMS-b-PEO-lipoamido polymer (ABA polymer with lipoamido moieties at the ends of the A blocks) are mixed together in a 1:1 ratio and used to form membranes such as described with reference to FIGS. 12A and 13. The structure of polymer 7 is shown below:

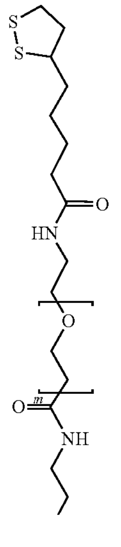

-continued

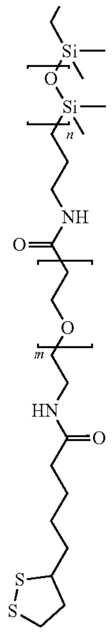

Polymer 7, in which the A blocks included about 8 PEO RU and the B block included about 41 RU, in which the lipoamido moieties are coupled to the terminal PEOs via respective amide bonds.

Figure 22:
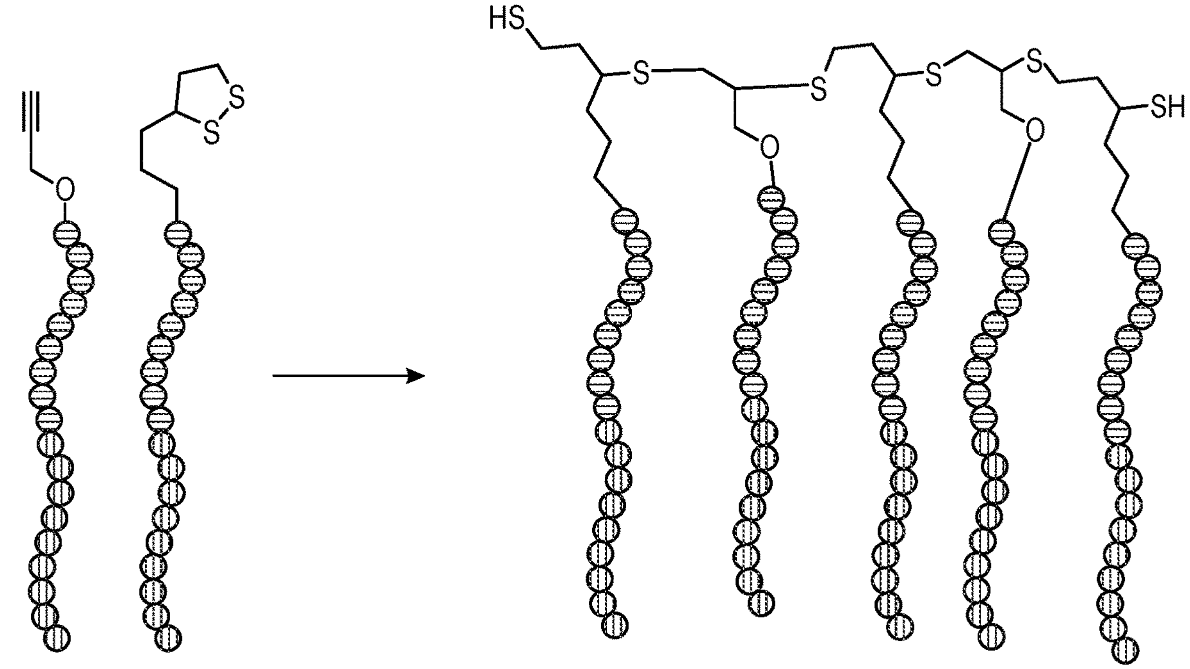
FIG. 22 schematically illustrates an example reaction product in the membranes that are crosslinked as described in Example 5.

The membranes are crosslinked using coupling reactions in a manner such as described with reference to FIGS. 12A-12B. FIG. 22 schematically illustrates an example reaction product in the membranes that are crosslinked as described in Example 5. As shown in FIG. 22, the reaction products of ring-opening and di-thiol formation coupling between the propargyl moieties of polymer 5 and the lipoamido moieties of polymer 7 includes sulfide bonds formed in a plane at the ends of the A blocks of the block copolymer. Note that the other end of the ABA copolymer is not shown, in some examples similar reaction products may be formed in a plane at the ends of the other A blocks, e.g., in examples in which both sides of the membrane are contacted with the initiator. In other examples, the reaction products substantially may be formed only at the ends of the A blocks on the first side of the membrane, e.g., in examples in which only that side of the membrane is contacted with the initiator.

Example 6

Figure 23A:
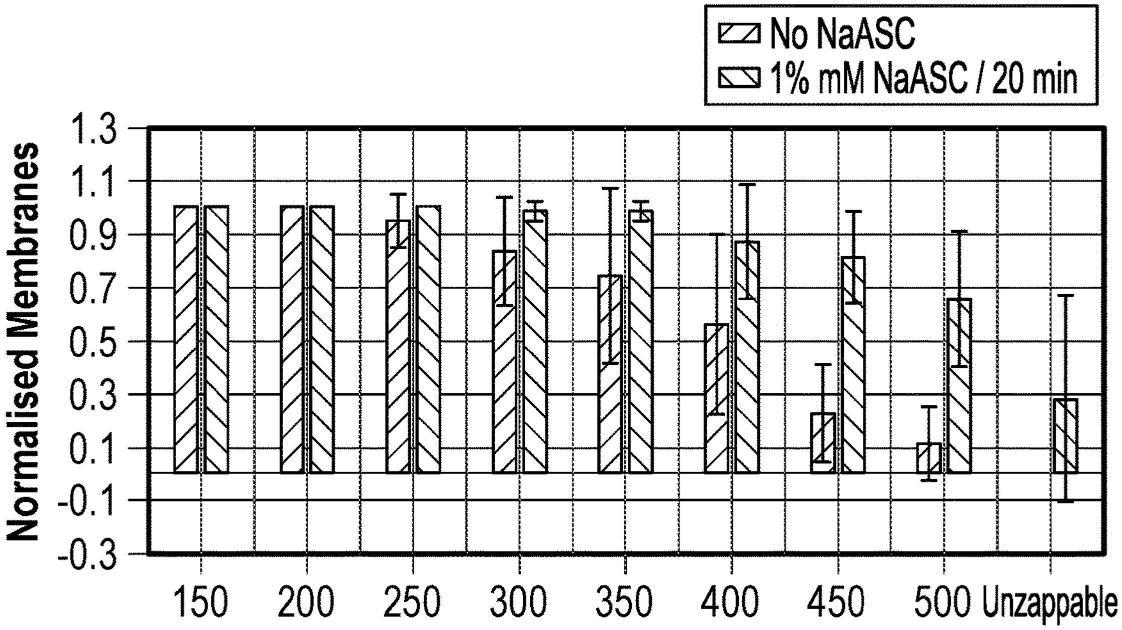
FIG. 23A is a plot of the membrane stability for membranes that were crosslinked with a reducing agent.

In Example 6, polymer 6 (the disulfide pyridyl-PEO-b-PDMS-b-PEO-disulfide pyridyl polymer of Example 4) was used to form membranes such as described with reference to FIG. 3A. The membranes were crosslinked using coupling reactions in a manner such as described with reference FIGS. 12A-12B, and 13, and their stability measured using the waveform described with reference to FIG. 17. FIG. 23A is a plot of the membrane stability for membranes that were crosslinked with a reducing agent. More specifically, after forming the membranes, the buffer solution on the second (cis) side 112 of a first set of the membranes was exchanged with a similar buffer solution containing 1 mM sodium ascorbate as the reducing agent. The reducing agent cleaved the pyridyl group from polymer 6, yielding free thiols at the ends of the A blocks of the copolymer. The reducing agent and pyridyl groups were washed away using several washes with an aqueous buffer including 1 M KCl and 50 mM HEPES. The free thiols then spontaneously reacted to form disulfide bridges between pairs of copolymer molecules. A second subset of the membranes were not incubated with the reducing agent as a control. From FIG. 23A it may be seen that the membranes that were incubated with the reducing agent for 20 minutes had higher stability at higher voltages than those that were not incubated with reducing agent. From these results, it may be understood that crosslinking enhanced stability of the membranes.

Figure 23B:
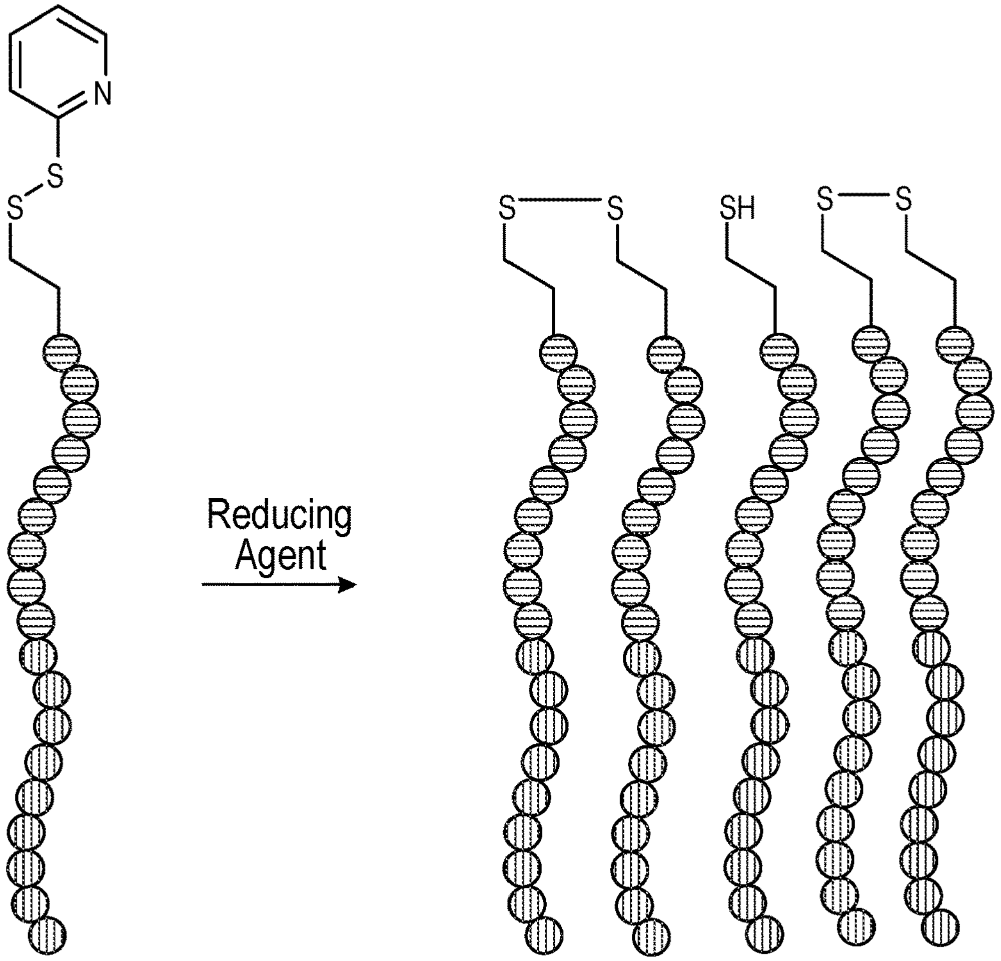
FIG. 23B schematically illustrates example reaction products in the membranes that were crosslinked as described with reference to FIG. 23A.

FIG. 23B schematically illustrates an example reaction product in the membranes that were crosslinked as described with reference to FIG. 23A. As shown in FIG. 23A, the reaction products of the coupling of the deprotected thiol moieties of polymer 6 includes a mixture of thiol groups and disulfide bridges formed in a plane at the ends of the A blocks of the block copolymer. Note that although the thiols and disulfide bridges on the other side of the membrane are not shown, in some examples a similar reaction product may be formed in a plane on the other side of the membrane, e.g., in examples in which both sides of the membrane are contacted with the reducing agent. In other examples, the reaction product substantially may be formed only at the ends of one set of the A blocks, e.g., in examples in which only one side of the membrane is contacted with the reducing agent. The reactions optionally may be reversible. For example, a reducing agent may be used to cleave disulfide bridges to obtain free thiols and reverse the cross-linking. Such reversibility may be useful, for example, in applications in which the membranes are shipped cross-linked for stability and then the cross-linking is reversed so the membranes are more fluid during use, e.g., sequencing.

Example 7

In Example 7, polymer 7 (the lipoamido-PEO-b-PDMS-b-PEO-lipoamido polymer of Example 5) is used to form membranes such as described with reference to FIG. 3A. The membranes are crosslinked using coupling reactions in a manner such as described with reference FIGS. 12A-12B, and 13. More specifically, after forming the membranes, the buffer solution on the second (cis) side 112 of the membranes is exchanged with a similar buffer solution containing a reducing agent. The reducing agent cleaves the disulfide within the lipoamido group of polymer 7, yielding free thiols at the ends of the A blocks of the copolymer. The reducing agent is washed away. The free thiols then oxidatively dimerize leading to formation of disulfide bridges between pairs of copolymer molecules.

Figure 24:
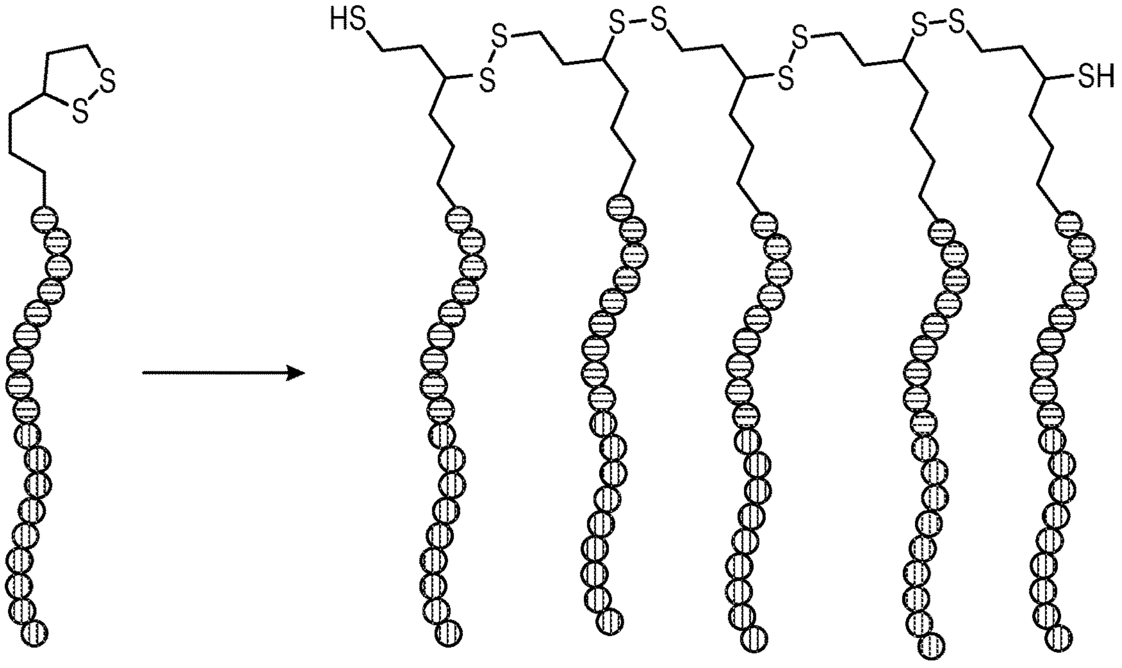
FIG. 24 schematically illustrates example reaction products in the membranes that are crosslinked as described in Example 7.

FIG. 24 schematically illustrates example reaction products in the membranes that are crosslinked as described in Example 7. As shown in FIG. 24, the reaction products of the coupling of the deprotected thiol moieties of polymer 7 includes a mixture of different disulfide bridges formed in a plane at the ends of the A blocks of the block copolymer. Note that although disulfide bridges on the other side of the membrane are not shown, in some examples a similar reaction product may be formed in a plane on the other side of the membrane, e.g., in examples in which both sides of the membrane are contacted with the reducing agent. In other examples, the reaction product substantially may be formed only at the ends of one set of the A blocks, e.g., in examples in which only one side of the membrane is contacted with the reducing agent.

Example 8

In Example 8, polymer 6 (the disulfide pyridyl-PEO-b-PDMS-b-PEO-disulfide pyridyl polymer ABA polymer of Example 4) was mixed with polymer 8, a maleimide-PEO-b-PDMS-b-PEO-maleimide polymer (ABA polymer with maleimide moieties at the ends of the A blocks) were mixed together in a 1:1 ratio and used to form membranes such as described with reference to FIGS. 12A and 13. The structure of polymer 8 is shown below:

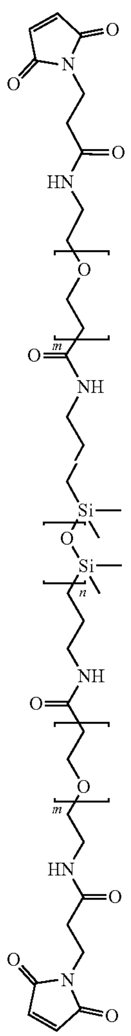

Polymer 8, in which the A blocks included about 8 PEO RU and the B block included about 41 RU, in which the maleimide moieties are coupled to the terminal PEOs via respective amide bonds.

Figure 25A:
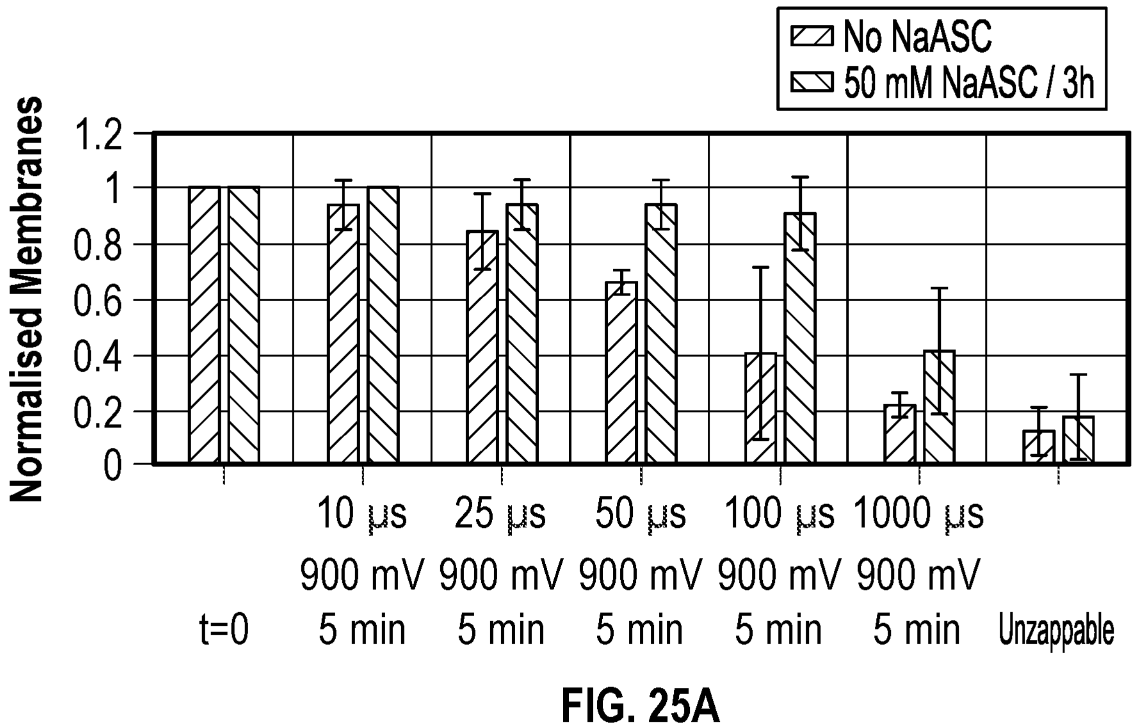
FIG. 25A is a plot of the measured membrane stability for membranes that were crosslinked using a reducing agent.

The membranes were crosslinked using coupling reactions in a manner such as described with reference to FIGS. 12A-12B and 13, and their stability measured using the waveform described with reference to FIG. 17. FIG. 25A is a plot of the measured membrane stability for membranes that were crosslinked using a reducing agent. More specifically, after forming the membranes, the buffer solution on the second (cis) side 112 of a first set of the membranes was exchanged with a similar buffer solution containing 1 mM sodium ascorbate as the reducing agent. The reducing agent cleaved the pyridyl group from polymer 6, yielding free thiols at the ends of the A blocks of the copolymer. The reducing agent and pyridyl groups were washed away using an aqueous buffer in the manner described in Example 6. The free thiols then cross-linked with the maleimide moieties of polymer 8. A second subset of the membranes were not incubated with the reducing agent as a control. From FIG. 25A it may be seen that the membranes that were incubated with the reducing agent for 3 hours had higher stability at higher voltages than those that were not incubated with reducing agent.

In this example, a modified waveform was used that increase pulse duration every five minutes, from 900 mV/1000 us. More specifically, the full waveform used was as follows:

Waveform A for 5 min
- −60 mV/180 ms
- 10 mV/20 ms
- 40 mV/480 ms with 8 pulses 900 mV/10 us every 30 ms Waveform B for 5 min
- −60 mV/180 ms
- 10 mV/20 ms
- 40 mV/480 ms with 8 pulses 900 mV/25 us every 30 ms Waveform C for 5 min
- −60 mV/180 ms
- 10 mV/20 ms
- 40 mV/480 ms with 8 pulses 900 mV/50 us every 30 ms Waveform D for 5 min
- −60 mV/180 ms
- 10 mV/20 ms
- 40 mV/480 ms with 8 pulses 900 mV/100 us every 30 ms Waveform E for 5 min
- −60 mV/180 ms
- 10 mV/20 ms
- 40 mV/480 ms with 8 pulses 900 mV/1000 us every 30 ms The motivation for this modified waveform was to increase resolution of the QC method. More specifically, the primary waveform 150 mV to 500 mV showed that membranes without cross-linking were very stable at 500 mV, so it was decided to use a harsher waveform to assess membranes with and without crosslinking. From these results, it may be understood that crosslinking enhanced stability of the membranes.

Figure 25B:
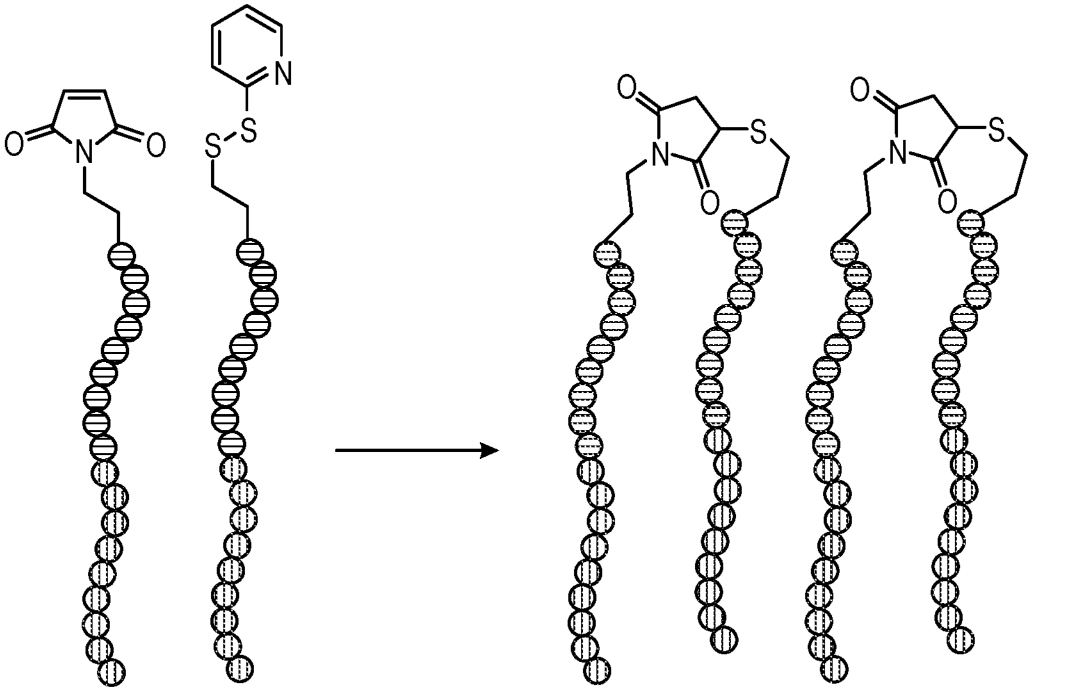
FIG. 25B schematically illustrates example reaction products in the membranes that were crosslinked as described with reference to FIG. 25A.

FIG. 25B schematically illustrates example reaction products in the membranes that were crosslinked as described with reference to FIG. 25A. As shown in FIG. 25B, the reaction products of coupling between the free thiol moieties of polymer 6 and the maleimide moieties of polymer 8 includes thiosuccinimide formed in a plane at the ends of the A blocks of the block copolymer. Note that the other end of the ABA copolymer is not shown, in some examples similar reaction products may be formed in a plane at the ends of the other A blocks, e.g., in examples in which both sides of the membrane are contacted with the reducing agent. In other examples, the reaction products substantially may be formed only at the ends of the A blocks on the first side of the membrane, e.g., in examples in which only that side of the membrane is contacted with the reducing agent.

Example 9

In Example 9, polymer 7 (the lipoamido-PEO-b-PDMS-b-PEO-lipoamido polymer polymer of Example 5) and with polymer 8 (the maleimide-PEO-b-PDMS-b-PEO-maleimide polymer of Example 8) are mixed together in a 1:1 ratio and used to form membranes such as described with reference to FIGS. 12A and 13.

Figure 26:
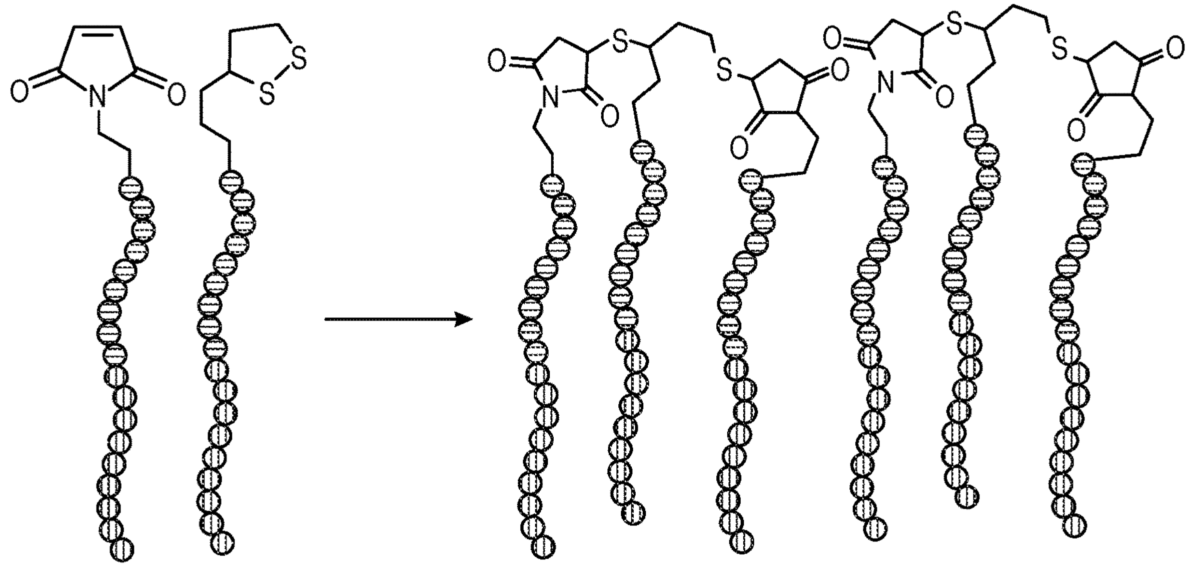
FIG. 26 schematically illustrates example reaction products in the membranes that are crosslinked as described in Example 9.

The membranes are crosslinked using coupling reactions in a manner such as described with reference to FIGS. 12A-12B and 13. More specifically, after forming the membranes, the buffer solution on the second (cis) side 112 of the membranes is exchanged with a similar buffer solution containing a reducing agent. The reducing agent opens the lipoamido group of polymer 7, yielding free thiols at the ends of the A blocks of the copolymer. The reducing agent is washed away. The free thiols then cross-link with the maleimide moieties of polymer 8. FIG. 26 schematically illustrates example reaction products in the membranes that are crosslinked as described in Example 9. As shown in FIG. 26, the reaction products of coupling between the free thiol moieties of polymer 7 and the maleimide moieties of polymer 8 includes thiosuccinimide formed in a plane at the ends of the A blocks of the block copolymer. Note that the other end of the ABA copolymer is not shown, in some examples similar reaction products may be formed in a plane at the ends of the other A blocks, e.g., in examples in which both sides of the membrane are contacted with the reducing agent. In other examples, the reaction products substantially may be formed only at the ends of the A blocks on the first side of the membrane, e.g., in examples in which only that side of the membrane is contacted with the reducing agent.

Example 10

In Example 10, polymer 10, a dimethyl maleimide-PEO-b-PDMS-b-PEO-dimethyl maleimide ABA polymer, is used to form membranes such as described with reference to FIG. 3A. The structure of polymer 10 is shown below:

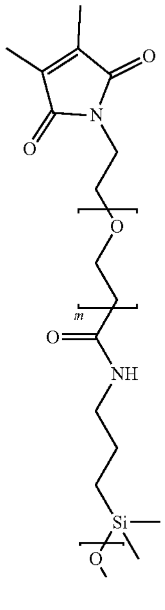

-continued

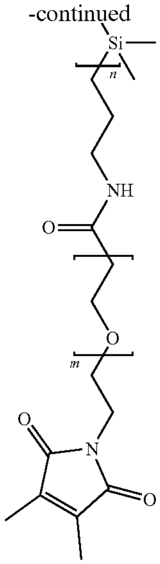

Polymer 10, in which in which the A blocks include about 10 PEO RU and the B block includes about 41 RU, in which the dimethyl maleimide moieties are coupled to the terminal PEOs via respective ether bonds.

Figure 27:
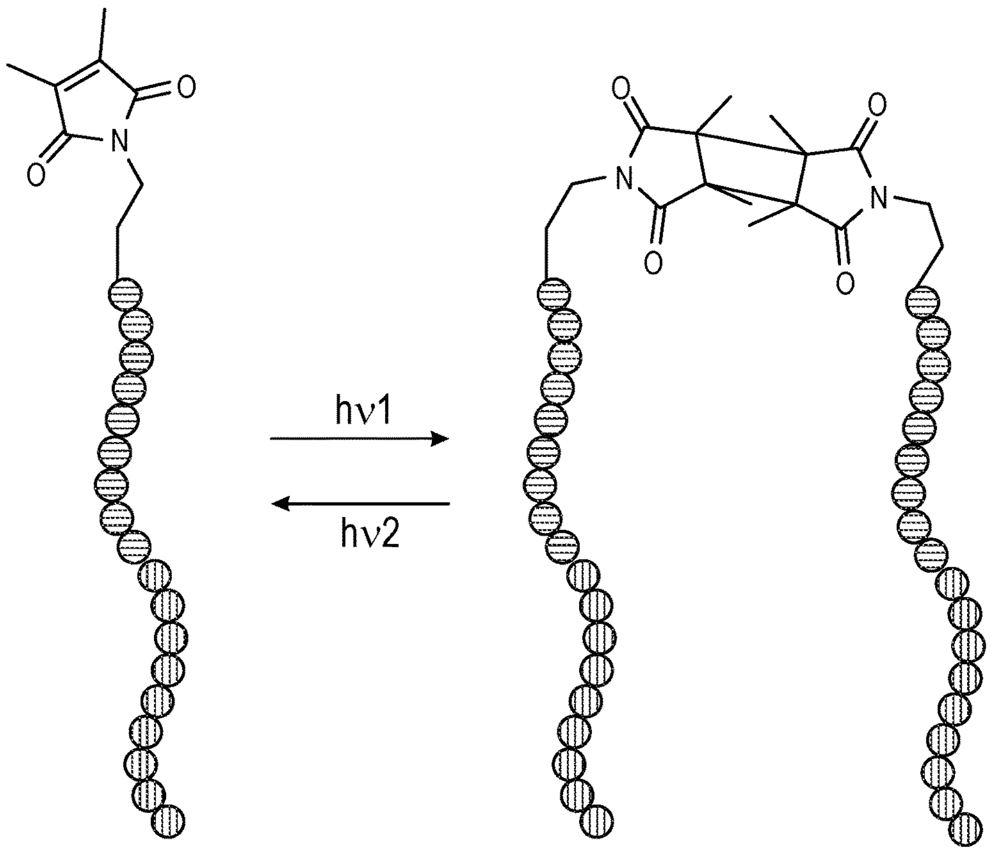
FIG. 27 schematically illustrates example reaction products in the membranes that are crosslinked as described in Example 10.

The membranes are crosslinked using coupling reactions in a manner such as described with reference FIGS. 3A-3C, 12A-12B, and 13. More specifically, after forming the membranes, the membrane is exposed to UV light responsive to which the dimethyl maleimide moieties react with one another leading to coupling between pairs of copolymer molecules. FIG. 27 schematically illustrates example reaction products in the membranes that are crosslinked as described in Example 10. As shown in FIG. 27, the reaction products of the coupling of the UV activated dimethyl maleimide moieties of polymer 10 includes a dimethylmaleimide conjugation product formed in a plane at the ends of the A blocks of the block copolymer. Note that although reaction products on the other side of the membrane are not shown, in some examples a similar reaction product may be formed in a plane on the other side of the membrane, e.g., in examples in which both sides of the membrane are contacted with the reducing agent. In other examples, the reaction product substantially may be formed only at the ends of one set of the A blocks, e.g., in examples in which only one side of the membrane is contacted with the reducing agent.

ADDITIONAL COMMENTS

While various illustrative examples are described above, it will be apparent to one skilled in the art that various changes and modifications may be made therein without departing from the invention. The appended claims are intended to cover all such changes and modifications that fall within the true spirit and scope of the invention.

It is to be understood that any respective features/examples of each of the aspects of the disclosure as described herein may be implemented together in any appropriate combination, and that any features/examples from any one or more of these aspects may be implemented together with any of the features of the other aspect(s) as described herein in any appropriate combination to achieve the benefits as described herein.

What is claimed is:

1. A barrier between first and second fluids, the barrier comprising:

at least one layer comprising a plurality of amphiphilic molecules, wherein amphiphilic molecules of the plurality of amphiphilic molecules comprise at least one hydrophobic block coupled to at least one hydrophilic block at an interface and are crosslinked to one another at the interface.

2. The barrier of claim 1, wherein the at least one layer comprises:

a first layer comprising a first plurality of amphiphilic molecules; and a second layer comprising a second plurality of amphiphilic molecules contacting the first plurality of amphiphilic molecules.

3. The barrier of claim 2, wherein amphiphilic molecules of the first layer are crosslinked to one another, and wherein amphiphilic molecules of the second layer are crosslinked to one another.

4. The barrier of claim 1, wherein the amphiphilic molecules comprise molecules of a diblock copolymer, molecules of the diblock copolymer comprising the hydrophobic block coupled to the hydrophilic block.

5. The barrier of claim 1, wherein the amphiphilic molecules comprise molecules of a triblock copolymer.

6. The barrier of claim 5, each molecule of the triblock copolymer comprising first and second hydrophobic blocks and the hydrophilic block coupled to and between the first and second hydrophobic blocks.

7. The barrier of claim 5, each molecule of the triblock copolymer comprising first and second hydrophilic blocks and the hydrophobic block coupled to and between the first and second hydrophilic blocks.

8. The barrier of claim 1, wherein the amphiphilic molecules are crosslinked by a product of a polymerization reaction.

9. The barrier of claim 8, wherein the product of the polymerization reaction comprises a reacted itaconic moiety, a reacted N-carboxyanhydride moiety, a reacted disulfyl pyridyl moiety, a reacted N-hydroxy succinimide (NHS) ester, a reacted acrylate moiety, a reacted methacrylate moiety, a reacted acrylamide moiety, a reacted methacrylamide moiety, a reacted styrenic moiety, a reacted maleic moiety, a reacted carboxylic acid moiety, a reacted thiol moiety, a reacted allyl moiety, a reacted vinyl moiety, a reacted propargyl moiety, or a reacted maleimide moiety.

10. The barrier of claim 1, wherein the amphiphilic molecules are crosslinked by a product of a coupling reaction.

11. The barrier of claim 10, wherein the coupling reaction comprises a thiol-ene click reaction, a thiol-yne click reaction, a strain-promoted alkyne-azide cycloaddition, an amide coupling, a thiol/aza-Michael reaction, a [2+2] cycloaddition, a thio-Michael click reaction, a condensation reaction, a [2+2] photocycloaddition, a protein-ligand interaction, host-guest chemistry, a disulfide formation, an imine formation, or an enamine formation.

12. The barrier of claim 1, further comprising a nanopore within the barrier.

13. The barrier of claim 12, wherein the nanopore comprises α-hemolysin or MspA.

14. The barrier of claim 1, the barrier being suspended by a barrier support defining an aperture, the one or more layers being suspended across the aperture.

15. A barrier between first and second fluids, the barrier comprising:

at least one layer comprising a plurality of amphiphilic molecules, wherein the amphiphilic molecules comprise at least one hydrophobic block coupled to at least one hydrophilic block at an interface and further comprise reactive moieties to perform a crosslinking reaction with one another at the interface.

16. A method of forming a barrier between first and second fluids, the method comprising:

forming at least one layer comprising a plurality of amphiphilic molecules, wherein the amphiphilic molecules comprise at least one hydrophobic block coupled to at least one hydrophilic block at an interface and further comprise reactive moieties;

using crosslinking reactions of the reactive moieties to crosslink amphiphilic molecules of the plurality to one another at the interface.

* * * * *